United States Patent
Jia et al.

(10) Patent No.: US 11,787,784 B2
(45) Date of Patent: *Oct. 17, 2023

(54) SOLID FORMS OF AN HPK1 INHIBITOR

(71) Applicant: Incyte Corporation, Wilmington, DE (US)

(72) Inventors: Zhongjiang Jia, Kennett Square, PA (US); William Frietze, Kenneth Square, PA (US)

(73) Assignee: Incyte Corporation, Wilmington, DE (US)

( * ) Notice: Subject to any disclaimer, the term of this patent is extended or adjusted under 35 U.S.C. 154(b) by 46 days.

This patent is subject to a terminal disclaimer.

(21) Appl. No.: 17/358,991

(22) Filed: Jun. 25, 2021

(65) Prior Publication Data
US 2022/0162195 A1    May 26, 2022

Related U.S. Application Data

(63) Continuation of application No. 16/985,526, filed on Aug. 5, 2020, now Pat. No. 11,066,394.

(60) Provisional application No. 62/889,848, filed on Aug. 21, 2019, provisional application No. 62/883,350, filed on Aug. 6, 2019.

(51) Int. Cl.
*C07D 403/14* (2006.01)
*C07D 403/12* (2006.01)

(52) U.S. Cl.
CPC ......... *C07D 403/14* (2013.01); *C07D 403/12* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 5,250,534 A | 10/1993 | Bell et al. |
| 6,200,980 B1 | 3/2001 | Piazza et al. |
| 6,333,330 B1 | 12/2001 | Bunnage et al. |
| 6,458,951 B2 | 10/2002 | Bunnage et al. |
| 6,512,002 B2 | 1/2003 | Lee et al. |
| 6,670,366 B1 | 12/2003 | Bunnage et al. |
| 6,743,799 B2 | 6/2004 | Westbrook et al. |
| 6,756,373 B1 | 6/2004 | Allerton et al. |
| 6,770,645 B2 | 8/2004 | Denton et al. |
| 6,784,185 B2 | 8/2004 | Allerton et al. |
| 6,916,927 B2 | 7/2005 | Bunnage et al. |
| 7,105,532 B2 | 9/2006 | Rawlings |
| 7,166,293 B2 | 1/2007 | Teng et al. |
| 7,259,165 B2 | 8/2007 | Bernotas et al. |
| 7,345,178 B2 | 3/2008 | Nunes et al. |
| 7,429,609 B2 | 9/2008 | Ohi et al. |
| 7,576,087 B2 | 8/2009 | Bernotas et al. |
| 7,919,487 B2 | 4/2011 | Sun et al. |
| 7,968,719 B2 | 6/2011 | Zoller et al. |
| 8,106,190 B2 | 1/2012 | Kuramochi et al. |
| 8,450,335 B2 | 5/2013 | Singh et al. |
| 8,546,403 B2 | 10/2013 | Whitten et al. |
| 8,637,507 B2 | 1/2014 | Zhou et al. |
| 8,722,691 B2 | 3/2014 | He et al. |
| 8,987,273 B2 | 3/2015 | Rehwinkel et al. |
| 9,090,593 B2 | 7/2015 | Wang et al. |
| 9,260,425 B2 | 2/2016 | Do et al. |
| 9,284,319 B2 | 3/2016 | Eis et al. |
| 9,320,737 B2 | 4/2016 | Eis et al. |
| 9,718,818 B2 | 8/2017 | DeMong et al. |
| 9,730,929 B2 | 8/2017 | Eis et al. |
| 10,266,530 B2 | 4/2019 | Vechorkin et al. |
| 10,280,164 B2 | 5/2019 | Ye et al. |
| 10,435,405 B2 | 10/2019 | Vechorkin et al. |
| 10,722,495 B2 | 7/2020 | Vechorkin et al. |
| 10,745,388 B2 | 8/2020 | Vechorkin et al. |
| 10,752,635 B2 | 8/2020 | Sokolsky et al. |
| 10,800,761 B2 | 10/2020 | Vechorkin et al. |
| 10,899,755 B2 | 1/2021 | Hummel et al. |
| 10,934,288 B2 | 3/2021 | Vechorkin et al. |
| 11,014,929 B2 | 5/2021 | Vechorkin et al. |
| 11,066,394 B2 | 7/2021 | Jia et al. |
| 11,242,343 B2 | 2/2022 | Liu et al. |
| 11,299,473 B2 | 4/2022 | Hummel et al. |
| 11,406,624 B2 | 8/2022 | Sokolsky et al. |
| 11,492,354 B2 | 11/2022 | Sokolsky et al. |
| 11,542,265 B2 | 1/2023 | Vechorkin et al. |
| 2002/0013327 A1 | 1/2002 | Lee et al. |
| 2003/0162782 A1 | 8/2003 | Grossman et al. |

(Continued)

FOREIGN PATENT DOCUMENTS

| | | |
|---|---|---|
| CN | 101801981 | 8/2010 |
| CN | 101918371 | 12/2010 |

(Continued)

OTHER PUBLICATIONS

Alzabin et al., "Hematopoietic progenitor kinase 1 is a critical component of prostaglandin E2-mediated suppression of the antitumor immune response," Cancer Immunol Immunother, 2010, 59(3):419-429.
Alzabin et al., "Hematopoietic progenitor kinase 1 is a negative regulator of dendritic cell activation," J Immunol, 2009, 182(10):6187-6194.
Anonymous, "Crystalline ethyl 1-(4-methoxyphenyl)-6-(4-nitrophenyl)-7-oxo-,5,6,7-tetrahydro-1H-pyrazolo[3,4-c]pyridine-3-carboxylate," IP.com #IPCQM000233229D, Dec. 3, 2019, 4 pages.
Anonymous, "Crystalline APX," IP.com #IPCOM000233879, Dec. 25, 2013, 3 pages.

(Continued)

*Primary Examiner* — Brian J Davis
(74) *Attorney, Agent, or Firm* — Fish & Richardson P.C.

(57) ABSTRACT

The present invention relates to salt forms of the hematopoietic progenitor kinase 1 (HPK1) inhibitors N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide and N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide, including methods of preparation thereof, where the compounds are useful in the treatment of HPK1 mediated diseases such as cancer.

26 Claims, 30 Drawing Sheets

(56) References Cited

U.S. PATENT DOCUMENTS

| | | |
|---|---|---|
| 2003/0186996 A1 | 10/2003 | Teng et al. |
| 2004/0063730 A1 | 4/2004 | Eggenweiler et al. |
| 2004/0077681 A1 | 4/2004 | Rawlings et al. |
| 2004/0147546 A1 | 7/2004 | Tanaka et al. |
| 2004/0157866 A1 | 8/2004 | Takasugi et al. |
| 2004/0167030 A1 | 8/2004 | Bernotas et al. |
| 2004/0204417 A1 | 10/2004 | Perez et al. |
| 2005/0070557 A1 | 3/2005 | Fryburg et al. |
| 2005/0075795 A1 | 4/2005 | Pandit |
| 2005/0119278 A1 | 6/2005 | Teng et al. |
| 2005/0137226 A1 | 6/2005 | Ji et al. |
| 2005/0208582 A1 | 9/2005 | Ohi et al. |
| 2005/0261339 A1 | 11/2005 | Ohi et al. |
| 2006/0106032 A1 | 5/2006 | Kuo et al. |
| 2007/0087988 A1 | 4/2007 | Sawasdikosol et al. |
| 2007/0161673 A1 | 7/2007 | Barker et al. |
| 2007/0185152 A1 | 8/2007 | Yamashita et al. |
| 2007/0270412 A1 | 11/2007 | Bell et al. |
| 2008/0280891 A1 | 11/2008 | Kelly et al. |
| 2010/0035891 A1 | 2/2010 | Bunnage et al. |
| 2010/0087464 A1 | 4/2010 | Mi et al. |
| 2010/0216798 A1 | 8/2010 | Nakai et al. |
| 2012/0129852 A1 | 5/2012 | Duan et al. |
| 2012/0225869 A1 | 9/2012 | Liu et al. |
| 2012/0295884 A1 | 11/2012 | Altmann et al. |
| 2013/0039906 A1 | 2/2013 | Do et al. |
| 2013/0040949 A1 | 2/2013 | Gray et al. |
| 2013/0281433 A1 | 10/2013 | Babaoglu et al. |
| 2014/0225073 A1 | 8/2014 | Lee et al. |
| 2014/0249135 A1 | 9/2014 | Burger et al. |
| 2014/0288045 A1 | 9/2014 | Ren et al. |
| 2014/0288069 A1 | 9/2014 | Eis et al. |
| 2014/0350017 A1 | 11/2014 | Williams et al. |
| 2014/0364605 A1 | 12/2014 | Li et al. |
| 2015/0038485 A1 | 2/2015 | Eis et al. |
| 2015/0191462 A1 | 7/2015 | Hommel et al. |
| 2015/0239868 A1 | 8/2015 | Pais et al. |
| 2015/0239889 A1 | 8/2015 | Nakajima et al. |
| 2015/0243908 A1 | 8/2015 | Lee et al. |
| 2015/0274639 A1 | 10/2015 | Williams et al. |
| 2015/0328188 A1 | 11/2015 | Orlemans et al. |
| 2016/0013427 A1 | 1/2016 | Kim et al. |
| 2016/0046648 A1 | 2/2016 | Petrukhin et al. |
| 2016/0068529 A1 | 3/2016 | Kc et al. |
| 2016/0068547 A1 | 3/2016 | Kc et al. |
| 2016/0068548 A1 | 3/2016 | Kc et al. |
| 2016/0068551 A1 | 3/2016 | Kc et al. |
| 2016/0200722 A1 | 7/2016 | DeMong et al. |
| 2018/0072718 A1 | 3/2018 | Liu et al. |
| 2018/0072719 A1 | 3/2018 | Ye et al. |
| 2018/0072720 A1 | 3/2018 | Vechorkin et al. |
| 2018/0072741 A1 | 3/2018 | Vechorkin et al. |
| 2018/0228786 A1 | 8/2018 | Sokolsky |
| 2019/0076401 A1 | 3/2019 | Vechorkin et al. |
| 2019/0106419 A1 | 4/2019 | Vechorkin et al. |
| 2019/0256500 A1 | 8/2019 | Vechorkin et al. |
| 2019/0256520 A1 | 8/2019 | Sokolsky |
| 2019/0315717 A1 | 10/2019 | Hummel et al. |
| 2019/0315743 A1 | 10/2019 | Liu et al. |
| 2019/0343814 A1 | 11/2019 | Sokolsky |
| 2019/0382380 A1 | 12/2019 | Vechorkin et al. |
| 2020/0048241 A1 | 2/2020 | Hummel et al. |
| 2020/0087301 A1 | 3/2020 | Vechorkin et al. |
| 2020/0172545 A1 | 6/2020 | Vechorkin et al. |
| 2020/0283434 A1 | 9/2020 | Liu et al. |
| 2021/0002288 A1 | 1/2021 | Sokolsky |
| 2021/0040071 A1 | 2/2021 | Jia et al. |
| 2021/0094934 A1 | 4/2021 | Vechorkin et al. |
| 2021/0171518 A1 | 6/2021 | Hummel et al. |
| 2021/0371425 A1 | 12/2021 | Vechorkin et al. |
| 2021/0380581 A1 | 12/2021 | Vechorkin et al. |
| 2022/0227752 A1 | 7/2022 | Liu et al. |

FOREIGN PATENT DOCUMENTS

| | | |
|---|---|---|
| CN | 102206172 | 10/2011 |
| CN | 102503959 | 6/2012 |
| CN | 102516263 | 6/2012 |
| CN | 103570709 | 2/2014 |
| CN | 107922431 | 4/2018 |
| DE | 10 2004 054 666 | 5/2006 |
| EP | 2543372 | 1/2013 |
| EP | 2824099 | 1/2015 |
| IN | 187433 | 4/2002 |
| JP | H03287584 | 12/1991 |
| JP | 2000-038350 | 2/2000 |
| JP | 2007-055940 | 3/2007 |
| JP | 2010-111624 | 5/2010 |
| JP | 2010520228 | 6/2010 |
| JP | 2010533716 | 10/2010 |
| JP | 2011-246389 | 12/2011 |
| KR | 963644 | 2/1996 |
| KR | 10 2014 0019055 | 2/2014 |
| KR | 20180015255 | 2/2018 |
| MX | 9910322 | 7/2003 |
| MY | 146643 | 9/2012 |
| TW | 1771319 | 7/2022 |
| WO | WO 1989/008263 | 9/1989 |
| WO | WO 2000/043394 | 7/2000 |
| WO | WO 2001/019827 | 3/2001 |
| WO | WO 2001/019828 | 3/2001 |
| WO | WO 2001/021576 | 3/2001 |
| WO | WO 2001/046124 | 6/2001 |
| WO | WO 2002/000196 | 1/2002 |
| WO | WO 2002/016348 | 2/2002 |
| WO | WO 2002/019975 | 3/2002 |
| WO | WO 2002/050073 | 6/2002 |
| WO | WO 2002/090347 | 11/2002 |
| WO | WO 2003/037432 | 5/2003 |
| WO | WO 2003/049681 | 6/2003 |
| WO | WO 2004/072069 | 8/2004 |
| WO | WO 2004/096810 | 11/2004 |
| WO | WO 2004/108133 | 12/2004 |
| WO | WO 2005/004799 | 1/2005 |
| WO | WO 2005/011681 | 2/2005 |
| WO | WO 2005/028475 | 3/2005 |
| WO | WO 2005/051906 | 6/2005 |
| WO | WO 2005/066167 | 7/2005 |
| WO | WO 2005/073199 | 8/2005 |
| WO | WO 2005/073232 | 8/2005 |
| WO | WO 2003/101968 | 9/2005 |
| WO | WO 2005/085227 | 9/2005 |
| WO | WO 2005/085248 | 9/2005 |
| WO | WO 2005/085249 | 9/2005 |
| WO | WO 2006/013095 | 2/2006 |
| WO | WO 2006/028958 | 3/2006 |
| WO | WO 2006/038001 | 4/2006 |
| WO | WO 2006/045010 | 4/2006 |
| WO | WO 2006/050097 | 5/2006 |
| WO | WO 2006/053109 | 5/2006 |
| WO | WO 2006/053121 | 5/2006 |
| WO | WO 2006/053227 | 5/2006 |
| WO | WO 2006/074428 | 7/2006 |
| WO | WO 2006/105289 | 10/2006 |
| WO | WO 2006/128172 | 11/2006 |
| WO | WO 2007/019344 | 2/2007 |
| WO | WO 2007/019345 | 2/2007 |
| WO | WO 2007/019346 | 2/2007 |
| WO | WO 2007/019417 | 2/2007 |
| WO | WO 2007/020050 | 2/2007 |
| WO | WO 2007/023110 | 3/2007 |
| WO | WO 2007/023111 | 3/2007 |
| WO | WO 2007/023114 | 3/2007 |
| WO | WO 2007/030582 | 3/2007 |
| WO | WO 2007/056280 | 5/2007 |
| WO | WO 2007/063925 | 6/2007 |
| WO | WO 2007/065924 | 6/2007 |
| WO | WO 2007/080382 | 7/2007 |
| WO | WO 2007/093402 | 8/2007 |
| WO | WO 2007/112093 | 10/2007 |
| WO | WO 2007/114848 | 10/2007 |
| WO | WO 2007/137030 | 11/2007 |

(56) References Cited

FOREIGN PATENT DOCUMENTS

| | | |
|---|---|---|
| WO | WO 2008/008059 | 1/2008 |
| WO | WO 2008/008539 | 1/2008 |
| WO | WO 2008/012027 | 1/2008 |
| WO | WO 2008/045627 | 4/2008 |
| WO | WO 2008/070313 | 6/2008 |
| WO | WO 2008/089307 | 7/2008 |
| WO | WO 2008/089310 | 7/2008 |
| WO | WO 2008/113856 | 9/2008 |
| WO | WO 2009/019167 | 2/2009 |
| WO | WO 2009/024341 | 2/2009 |
| WO | WO 2009/032651 | 3/2009 |
| WO | WO 2009/038784 | 3/2009 |
| WO | WO 2009/058348 | 5/2009 |
| WO | WO 2009/100130 | 8/2009 |
| WO | WO 2009/139834 | 11/2009 |
| WO | WO 2009/152356 | 12/2009 |
| WO | WO 2010/029300 | 3/2010 |
| WO | WO 2010/035217 | 4/2010 |
| WO | WO 2010/035219 | 4/2010 |
| WO | WO 2010/035221 | 4/2010 |
| WO | WO 2010/046780 | 4/2010 |
| WO | WO 2010/080503 | 7/2010 |
| WO | WO 2010/104306 | 9/2010 |
| WO | WO 2010/107765 | 9/2010 |
| WO | WO 2010/107768 | 9/2010 |
| WO | WO 2010/111624 | 9/2010 |
| WO | WO 2010/118367 | 10/2010 |
| WO | WO 2011/019780 | 2/2011 |
| WO | WO 2011/031628 | 3/2011 |
| WO | WO 2011/050245 | 4/2011 |
| WO | WO 2011/051535 | 5/2011 |
| WO | WO 2011/062253 | 5/2011 |
| WO | WO 2011/078143 | 6/2011 |
| WO | WO 2011/082400 | 7/2011 |
| WO | WO 2011/082488 | 7/2011 |
| WO | WO 2011/107186 | 9/2011 |
| WO | WO 2011/133920 | 10/2011 |
| WO | WO 2011/139489 | 11/2011 |
| WO | WO 2011/141756 | 11/2011 |
| WO | WO 2011/147765 | 12/2011 |
| WO | WO 2011/153553 | 12/2011 |
| WO | WO 2011/157653 | 12/2011 |
| WO | WO 2011/158108 | 12/2011 |
| WO | WO 2012/048058 | 4/2012 |
| WO | WO 2012/049277 | 4/2012 |
| WO | WO 2012/078777 | 6/2012 |
| WO | WO 2012/080376 | 6/2012 |
| WO | WO 2012/109263 | 8/2012 |
| WO | WO 2012/130780 | 10/2012 |
| WO | WO 2012/141487 | 10/2012 |
| WO | WO 2012/143144 | 10/2012 |
| WO | WO 2012/158810 | 11/2012 |
| WO | WO 2012151567 | 11/2012 |
| WO | WO 2012/163959 | 12/2012 |
| WO | WO 2013/007708 | 1/2013 |
| WO | WO 2013/021276 | 2/2013 |
| WO | WO 2013/024002 | 2/2013 |
| WO | WO 2013/024011 | 2/2013 |
| WO | WO 2013/042137 | 3/2013 |
| WO | WO 2013/064445 | 5/2013 |
| WO | WO 2013/123215 | 8/2013 |
| WO | WO 2013/130890 | 9/2013 |
| WO | WO 2013/146942 | 10/2013 |
| WO | WO 2014/003405 | 1/2014 |
| WO | WO 2014/024125 | 2/2014 |
| WO | WO 2014/047616 | 3/2014 |
| WO | WO 2014/055955 | 4/2014 |
| WO | WO 2014/151616 | 9/2014 |
| WO | WO 2015/026683 | 2/2015 |
| WO | WO 2015/037965 | 3/2015 |
| WO | WO 2015/038503 | 3/2015 |
| WO | WO 2015/058163 | 4/2015 |
| WO | WO 2015/061247 | 4/2015 |
| WO | WO 2015/089327 | 6/2015 |
| WO | WO 2015/089479 | 6/2015 |
| WO | WO 2015/090235 | 6/2015 |
| WO | WO 2015/091426 | 6/2015 |
| WO | WO 2015/104662 | 7/2015 |
| WO | WO 2015/117718 | 8/2015 |
| WO | WO 2015/164956 | 11/2015 |
| WO | WO 2015/192939 | 12/2015 |
| WO | WO 2015/193506 | 12/2015 |
| WO | WO 2015/193846 | 12/2015 |
| WO | WO 2015/200682 | 12/2015 |
| WO | WO 2016/040180 | 3/2016 |
| WO | WO 2016/040181 | 3/2016 |
| WO | WO 2016/041618 | 3/2016 |
| WO | WO 2020151742 | 3/2016 |
| WO | WO 2016/057500 | 4/2016 |
| WO | WO 2016/083433 | 6/2016 |
| WO | WO 2016/090300 | 6/2016 |
| WO | WO 2016/124304 | 8/2016 |
| WO | WO 2016/144351 | 9/2016 |
| WO | WO 2016/144702 | 9/2016 |
| WO | WO 2016/164285 | 10/2016 |
| WO | WO 2016/174183 | 11/2016 |
| WO | WO 2016/205942 | 12/2016 |
| WO | WO 2017/009798 | 1/2017 |
| WO | WO 2017/009806 | 1/2017 |
| WO | WO 2017/023894 | 2/2017 |
| WO | WO 2017/023972 | 2/2017 |
| WO | WO 2017/027400 | 2/2017 |
| WO | WO 2017/045955 | 3/2017 |
| WO | WO 2017/058915 | 4/2017 |
| WO | WO 2017/108744 | 6/2017 |
| WO | WO 2017120429 | 7/2017 |
| WO | WO 2018019204 | 2/2018 |
| WO | WO 2018049152 | 3/2018 |
| WO | WO 2019/164846 | 8/2019 |
| WO | WO 2019/207463 | 2/2021 |
| WO | WO 2019/211451 | 2/2021 |
| WO | WO 2019/219517 | 3/2021 |
| ZA | 2003005330 | 7/2003 |

OTHER PUBLICATIONS

Antoine et al., "Efficient synthesis of novel disubstituted pyrido[3,4-b]pyrazines for the design of protein kinase inhibitors," Med Chem Common., 2016, 6:224-229.

Antunes et al., "In silico prediction of novel phosphodiesterase type-5 inhibitors derived from Sildenafil, Vardenafil and Tadalafil," Bioorg Med Chem., Aug. 15, 2008, 16(16):7599-7606.

Atzrodt et al., "The Renaissance of H/D Exchange," Angew. Chem. Int. Ed., 2007, 7744-7765.

Australian Office Action in Australian Application No. 2017322427, dated Dec. 16, 2020, 5 pages.

Bae et al., "Cancer Targeted Drug Delivery," Springer: New York, 2013, p. v.

Ballell et al., "Fueling Open-Source Drug Discovery: 177 Small-Molecule Leads against Tuberculosis," ChemMedChem., 2013, 8(2):313-321.

Balog et al., "The synthesis and evaluation of [2.2.1]—bicycloazahydantoins as androgen receptor antagonists," Bioorg. Med. Chem. Lett., Dec. 20, 2004, 14(24):6107-6111.

Batliwalla et al., "Microarray analyses of peripheral blood cells identifies unique gene expression signature in psoriatic arthritis," Mol Med, 2005, 11(1-12):21-29.

Benz, "The Jeremiah Metzger Lecture Cancer in the Twenty-First Century: An Inside View from an Outsider," Trans Am Clin Climatol Assoc., 2017, 128:275-297.

Berge et al., "Pharmaceutical Salts," J. Pharm. Sci., 1977, 66(1):1-19.

Blom et al., "Optimizing Preparative LC-MS Configurations and Methods for Parallel Synthesis Purification," J. Combi. Chem., 2003, 5:670.

Blom et al., "Preparative LC-MS Purification: Improved Compound Specific Method Optimization," J. Combi. Chem., 2004, 6:874-883.

Blom et al., "Two-Pump at Column Dilution Configuration for Preparative LC-MS," J. Combi. Chem., 2002, 4: 295.

(56) References Cited

OTHER PUBLICATIONS

Boomer et al., "Functional Interactions of HPK1 With Adaptor Proteins" Journal of Cellular Biochemistry, 2005, 95:34-44.

Brioche et al., "Chiral Phosphoric Acid-Catalyzed Enantioselective Three- Component Aza-Diels—Alder Reactions of Aminopyrroles and Aminopyrazoles," Advanced Synthesis & Catalysis, 2014, 356(8):1719-1724.

Chessari et al., "Fragment-Based Drug Discovery Targeting Inhibitor of Apoptosis Proteins: Discovery of a Non-Alanine Lead Series with Dual Activity Against cIAP1 and XIAP," J. Med. Chem., Jul. 18, 2015, 58(16):6574-6588.

Chilean Office Action in Chilean Application No. 2146-2020, dated Oct. 10, 2021, 19 pages.

Chinchilla and Najera, "Recent advances in Sonogashira reactions," Chem. Soc. Rev., 2011, 40: 5084-5121.

Chinese Office Action in Chinese Application No. 201780068722.2, dated Jul. 15, 2021, 13 pages.

Cheung et al., "A Parallel Synthesis Approach to the Identification of Novel Diheteroarylamide-Based Compounds Blocking HIV Replication: Potential Inhibitors of HIV-1 Pre-mRNA Alternative Splicing," J Med Chem., Mar. 10, 2016, 59(5):1869-1879.

Choi et al., "In vitro metabolism of a novel phosphodiesterase-5 inhibitor DA-8159 in rat liver preparations using liquid chromatography/electrospray mass spectrometry," Biomed Chromatogr., Sep. 2002, 16(6):395-399.

Cordovilla et al., "The Stille Reaction, 38 Years Later," ACS Catalysis, 2015, 5: 3040-3053.

Devegowda et al., "Novel 6-N-arylcarboxamidopyrazolo[4,3-d]pyrimidin-7-one derivatives as potential anti-cancer agents," Bioorg Med Chem Lett., Mar. 1, 2010, 20(5):1630-1633.

Di Bartolo et al., "A novel pathway down-modulating T cell activation involves HPK-1-dependent recruitment of 14-3-3 proteins on SLP-76," J. Exp. Med., Mar. 2007, 204(3): 681-691.

Dolgin, "Lung Cancer Outlook," Nature, Nov. 19, 2020, 587:S16-S17.

Dong et al., "Pharmacophore identification, virtual screening and biological evaluation of prenylated flavonoids derivatives as PKB/Akt1 inhibitors," Eur J Med Chem., Dec. 2011, 46(12):5949-5958.

Dong et al., "QSAR study of Akt/protein kinase B (PKB) inhibitors using support vector machine," Eur J Med Chem., Oct. 2009, 44(10):4090-4097.

Dornow et al., "Syntheses of nitrogen-containing heterocycles. XXXVIII. Preparation and reaction of several substituted 3-nitropyridines," Chemische Berichte, 1966, 99(1):244-253 (Machine Translation).

Dumestre-Toulet et al., "Last performance with VIAGRA: post-mortem identification of sildenafil and its metabolites in biological specimens including hair sample," Forensic Sci Int., Mar. 28, 2002, 126(1):71-76.

El-Aziz et al., "Synthesis and in vitro anti-breast cancer activity of some novel 1,4-dihydropyridine derivatives," Int J of Pharm Pharma Sci., 2013, 5(Suppl. 3):183-189.

El Sayed et al., "New route for the preparation of pyrazolo[4,3-c]pyridines," Bulletin of the Chemical Society of Japan (1973), 46(6), 1801-1803.

Edmondson et al., "Aminopiperidine-fused imidazoles as dipeptidyl peptidase—IV inhibitors," Bioorg Med Chem Lett., Aug. 2009, 19(15):4097-4101.

Elgemeie et al., "A new general method for substituted 4-alkylthio-N-arylsulfonylamino-2-pyridones: Reaction of ketene-S,S-acetals with arylsulfonylhydrazides," Phosphorus, Sulfur and Silicon and the Related Elements, 2001, 170:171-179.

Elgemeie et al., "Novel N-Substituted Amino-4-methylsulfanyl-2-pyridones and Deazapurine Analogues from Ketene Dithioacetals," J Chem Res., 1998, 3:164-165.

Elgemeie et al., "Novel synthesis of N-aroylaminated pyridones via reaction of ketene dithioacetals with cyanoaceto-N-aroylhydrazides," Synth Comm., 2003, 33(2):253-258.

Elgemeie et al., "Novel Nucleoside Analogues: First Synthesis of Pyridine-4-Thioglycosides and Their Cytotoxic Evaluation," Nucleosides, Nucleotides and Nucleic Acids, Jun. 27, 2015, 34:659-673.

Elgemeie et al., "Synthesis of Novel Derivatives of 4-Methylthio-N-Aryl-2-Pyridone and Deazapurine Analogues: The Reaction of Ketene Dithioacetals with Substituted Acetanilides," Phosphorus, Sulfur and Silicon, 2000, 164:189-197.

Erian, "2-Aryl-1,1-dicyano-3-phenylsulfonylpropenes in heterocyclic synthesis. A synthetic strategy towards heterocyclic sulfone," Monatshefte fuer Chemie, Oct. 1998, 129(10):1049-1056.

Eurasian Office Action in Eurasian Application No. 201990665, dated Feb. 17, 2020, 5 pages.

Eurasian Office Action in Eurasian Application No. 202091983, dated Nov. 29, 2021, 4 pages.

Tavassoli and Devilee, "Pathology and Genetics: Tumours of the Breast and Female Genital Organs," World Health Organization Classification of Tumours, 2003 [retrieved Nov. 4, 2016], retrieved from URL <http://www.iarc.fr/en/publications/pdfs-online/pat-gen/bb4/BB4.pdf>, pp. 1-112.

Figueiredo et al., "A chemometric study of phosphodiesterase 5 inhibitors," J Mol Graph Model., Jan. 2006, 24(4):227-232.

Gao, "Slidenafil" Handbook of Metabolic Pathways of Xenobiotics, 2014, 5:2151-2154.

Garson et al., "Models of ovarian cancer—Are we there yet?" Molecular and Cellular Endocrinology, Jul. 2005, 239(1-2):15-26.

Gerratana et al., "Do platinum salts fit all triple negative breast cancers?" Cancer Treatment Reviews, Jul. 2016, 48:34-41.

Goodarzi et al., "Feature Selection and Linear/Nonlinear Regression Methods for the Accurate Prediction of Glycogen Synthase Kinase-3β Inhibitory Activities," J. Chem. Inf. Model, 2009, 49(4):824-832.

Haas et al., "Recent Developments in Negishi Cross-Coupling Reactions," ACS Catalysis, 2016, 6: 1540-1552.

Haning et al., "Comparison of different heterocyclic scaffolds as substrate analog PDE5 inhibitors," Sep. 1, 2005, 15(17):3900-3907.

Hanson, "Diterpenoids of Terrestrial Origin", National Product Reports, 2016, 33:1227-1238.

Hayat, "Autophagy: Cancer, other Pathologies, Inflammation, Immunity, Infection, and Aging," Academic Press: San Diego, 2015, p. xxi.

He et al., "Predicting the Genotoxicity of Polycyclic Aromatic Compounds from Molecular Structure with Different Classifiers," Chemical Research in Toxicology (2003), 16(12):1567-1580.

Hu et al., "Discovery of 3,5-substituted 6-azaindazoles as potent pan-Pim inhibitors," Bioorg Med Chem Lett., 2015, 25(22):5258-5264.

Hu et al., "Human HPK1, a novel human hematopoietic progenitor kinase that activates the JNK/SAPK kinase cascade," Genes Dev, 1996, 10(18): p. 2251-2264.

Hudis et al., "Triple-Negative Breast Cancer: An Unmet Medical Need," The Oncologist, 2011, 16(suppl 1):1-11.

Ho et al., "Discovery of 4-phenyl-2-phenylaminopyridine based TNIK inhibitors," Boorg Med Chem Lett, 2013, 23(2):569-573.

Howard et al., "Identification of potent phosphodiesterase inhibitors that demonstrate cyclic nucleotide-dependent functions in apicomplexan parasites," ACS Chem Biol., Apr. 17, 2015, 10(4):1145-1154.

Howington et al., "Treatment of Stage I and II Non-small Cell Lung Cancer Diagnosis and Management of Lung Cancer, 3rd ed: American College of Chest Physicians Evidence-Based Clinical Practice Guidelines," CHEST, May 2013, 143(5)(Suppl):e278S-e313S.

Ikegami et al., "The expression of prostaglandin E receptors EP2 and EP4 and their different regulation by lipopolysaccharide in C3H/HeN peritoneal macrophages," J. Immunol., Apr. 2001, 166(7): 4689-4696.

Indian Oral Hearing in Indian Application No. 201917010977, dated Aug. 13, 2021, 2 pages.

Indian Oral Hearing in Indian Application No. 201917010977, dated Sep. 16, 2021, 2 pages.

Indian Office Action in Indian Application No. 201917010977, dated Nov. 27, 2020, 5 pages.

(56) References Cited

OTHER PUBLICATIONS

International Search Report and Written Opinion in International Application No. PCT/US2017/048880, dated Nov. 2, 2017, 15 pages.
International Search Report and Written Opinion in International Application No. PCT/US2017/050669, dated Nov. 6, 2017, 16 pages.
International Search Report and Written Opinion in International Application No. PCT/US2017/050727, dated Nov. 2, 2017, 16 pages.
International Search Report and Written Opinion in International Application No. PCT/US2017/050737, dated Nov. 2, 2017, 16 pages.
International Search Report and Written Opinion in International Application No. PCT/US2017/050757, dated Nov. 10, 2017, 20 pages.
International Search Report and Written Opinion in International Application No. PCT/US2018/018205, dated Apr. 30, 2018, 16 pages.
International Search Report and Written Opinion in International Application No. PCT/US2018/049908, dated Nov. 7, 2018, 15 pages.
International Search Report and Written Opinion in International Application No. PCT/US2019/018609, dated May 13, 2019, 12 pages.
International Search Report and Written Opinion in International Application No. PCT/US2019/018608, dated Apr. 16, 2019, 14 pages.
International Search Report and Written Opinion in International Application No. PCT/2020/044919, Oct. 2, 2020, 14 pages.
International Preliminary Report on Patentability in International Application No. PCT/US2017/050669, dated Mar. 12, 2019, 8 pages.
International Preliminary Report on Patentability in International Application No. PCT/US2017/050737, dated Mar. 12, 2019, 8 pages.
International Preliminary Report on Patentability in International Application No. PCT/US2017/050727, dated Mar. 12, 2019, 8 pages.
International Preliminary Report on Patentability in International Application No. PCT/US2017/050757, dated Mar. 12, 2019, 10 pages.
International Preliminary Report on Patentability in International Application No. PCT/US2018/018205, dated Aug. 20, 2019, 10 pages.
International Preliminary Report on Patentability in International Application No. PCT/US2018/049908, dated Mar. 10, 2020, 8 pages.
International Preliminary Report on Patentability in International Application No. PCT/US2019/018609, dated Aug. 27, 2020, 7 pages.
International Preliminary Report on Patentability in International Application No. PCT/US2019/018608, dated Aug. 27, 2020, 8 pages.
Ivon et al., "Synthesis of a 2,5-Diazabicyclo[2.2.1]heptane-Derived α,β—Diamino Acid," Synthesis, 2015, 47(8):1123-1130.
Japanese Office Action in Japanese Application No. 2019-513288, dated Jun. 22, 2021, 9 pages.
Jett et al., "Treatment of Small Cell Lung Cancer Diagnosis and Management of Lung Cancer, 3rd ed: American College of Chest Physicians Evidence-Based Clinical Practice Guidelines," CHEST, May 2013, 143(5)(Suppl):e400S-e419S.
Johnson et al., "Relationships between drug activity in NCI preclinical in vitro and in vivo models and early clinical trials." British Journal of Cancer, 2001, 84(10):1424-1431.
Karaman "Analyzing the efficiency in intramolecular amide hydrolysis of Kirby's N-alkylmaleamic acids—A computational approach," Computational and Theoretical Chemistry, 2011, 974(1-3):133-142.
Katritzky et al., "QSAR modeling of the inhibition of Glycogen Synthase Kinase-3," Bioorganic & Medicinal Chemistry, 2006, 14(14):4987-5002.
Kerekes et al., "Aurora kinase inhibitors based on the imidazo[1,2-a]pyrazine core: fluorine and deuterium incorporation improve oral absorption and exposure," J. Med. Chem., Jan. 2011, 54(1): 201-210.
Kiefer et al., "HPK1, a hematopoietic protein kinase activating the SAPK/JNK pathway," EMBO. J., Dec. 1996, 15(24): 7013-7025.
Kim et al., "Reliable screening and confirmation of 156 multi-class illegal adulterants in dietary supplements based on extracted common ion chromatograms by ultra-high-performance liquid chromatography—quadrupole/time of flight-mass spectrometry," J Chromatogr A., Mar. 31, 2017, 1491:43-56.
Kotha et al., "Recent applications of the Suzuki—Miyaura cross-coupling reaction in organic synthesis," Tetrahedron, 2002, 58: 9633-9695.
Kumar et al., "3-(1H-Indol-2-yl)-1H-pyrazolo[4,3-b]pyridines as Wnt pathway modulators and their preparation," retrieved from STN Database Accession No. 2017: 232331, Feb. 9, 2017, Chemical Abstracts Service, Columbus, Ohio, US, XP002775032.
Kumar et al., "3-(1H-Indol-2-yl)-1H-pyrazolo[4,3-b]pyridines as Wnt pathway modulators and their preparation," retrieved from STN Database Accession No. 2017: 232415, Feb. 9, 2017, Chemical Abstracts Service, Columbus, Ohio, US, XP002775031.
Kumar et al., "3-(1H-Indol-2-yl)-1H-pyrazolo[4,3-b]pyridines as Wnt pathway modulators and their preparation," retrieved from STN Database Accession No. 2017: 232564, Feb. 9, 2017, Chemical Abstracts Service, Columbus, Ohio, US, XP002775030.
Kumar et al., "3-(1H-Indol-2-yl)-1H-pyrazolo[4,3-b]pyridines as Wnt pathway modulators and their preparation," retrieved from STN Database Accession No. 2017: 233013, Feb. 9, 2017, Chemical Abstracts Service, Columbus, Ohio, US, XP002775029.
Kumar et al., "3-(1H-Indol-2-yl)-1H-pyrazolo[4,3-b]pyridines as Wnt pathway modulators and their preparation," retrieved from STN Database Accession No. 2017: 233418, Feb. 9, 2017, Chemical Abstracts Service, Columbus, Ohio, US, XP002775028.
Kumar et al., "3-(1H-Indol-2-yl)-1H-pyrazolo[4,3-b]pyridines as Wnt pathway modulators and their preparation," retrieved from STN Database Accession No. 2017: 233427, Feb. 9, 2017, Chemical Abstracts Service, Columbus, Ohio, US, XP002775027.
Kumar et al., "3-(1H-Indol-2-yl)-1H-pyrazolo[4,3-b]pyridines as Wnt pathway modulators and their preparation," retrieved from STN Database Accession No. 2017: 233436, Feb. 9, 2017, Chemical Abstracts Service, Columbus, Ohio, US, XP002775026.
Lebel et al., "A rapid, quantitative liquid chromatography-mass spectrometry screening method for 71 active and 11 natural erectile dysfunction ingredients present in potentially adulterated or counterfeit products," J Chromatogr A., May 23, 2014, 1343:143-151.
Ledford, "US cancer institute overhauls cell lines," Nature, Feb. 25, 2016, 530(7591):391.
Lee et al., "Comparative metabolism of sildenafil in liver microsomes of different species by using LC/MS-based multivariate analysis," J of Chromato., Oct. 15, 2011, 879(28):3005-3011.
Li et al., "Metabolism of aildenafil in vivo in rats and in vitro in mouse, rat, dog, and human liver microsomes," Drug Test Anal., Jun. 2014., 6(6):552-562.
Li et al., "A highly effective one-pot synthesis of quinolines from o-nitroarylcarbaldehydes," Organic & Biomolecular Chemistry, 2007, 5(1):61-64.
Li et al., "One-pot Friedlander quinoline synthesis: scope and limitations," Synthesis, 2010, 10:1678-1686.
Lim et al., "Discovery of 1-(1 H-Pyrazolo [4,3-c]pyridin-6-yl)urea Inhibitors of Extracellular Signal-Regulated Kinase (ERK) for the Treatment of Cancers," Journal of Medicinal Chemistry, Jul. 2016, 59(13): 6501-6511.
Lin et al., "2, 3, 5-Trisbustituted pyridines as selective AKT inhibitors. Part II: Improved drug-like properties and kinase selectivity from azaindazoles," Bioorganic & Medicinal Chemistry Letters, 2010, 20: 679-683.
Lin et al., "Tetrasubstituted pyridines as potent and selective AKT inhibitors: Reduced CYP450 and hERG inhibition of aminopyridines," Bioorg Med Chem Lett. Jan. 15, 2010;20(2):684-688.

(56) References Cited

OTHER PUBLICATIONS

Liou et al., "HPK1 is activated by lymphocyte antigen receptors and negatively regulates AP-1," Immunity, Apr. 2000, 12(4): 399-408.
Liu et al., "Synthesis and SAR of 1,9-dihydro-9-hydroxypyrazolo[3,4-b]quinolin-4-ones as novel, selective c-Jun N-terminal kinase inhibitors," Bioorg Med Chem Lett., May 15, 2006, 16(10):2590-2594.
Maley and Greaves, "Frontiers in Cancer Research," Springer: New York, 2016, pp. 18-19.
McMahon "VEGF Receptor Signaling in Tumor Angiogenesis," The Oncologist, 2000, 5(suppl 1):3-10.
Michelotti et al., "Two Classes of p38a MAP kinase inhibitors having a common core but exhibiting devergent binding modes," 2005, 15:5274-5279.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorg Med Chem Lett., Jan. 1, 2007, 17(1):250-254.
Morissette et al., "High-throughput crystallization: polymorphs, salts, co-crystals and solvates of pharmaceutical solids," Adv Drug Deliv Rev., Feb. 23, 2004, 56(3):275-300.
Muddassar et al., "Elucidation of binding mode and three dimensional quantitative structure—activity relationship studies of a novel series of protein kinase B/Akt inhibitors," J Mol Model., Feb. 2009, 15(2):183-192.
Mulvihill et al., "Novel 2-phenylquinolin-7-yl-derived imidazo[1,5-a]pyrazines as potent insulin-like growth factor-I receptor (IGF-IR) inhibitors," Bioorg Med Chem Lett, Feb. 2008, 16(3): 1359-1375.
Ocana et al., "Preclinical development of molecular targeted agents for cancer," Nat Rev Olin Oncol., Dec. 2011, 8(4):200-209.
Patel et al., "Selectivity criterion for pyrazolo[3,4-b]pyrid[az]ine derivatives as GSK-3 inhibitors: CoMFA and molecular docking studies," European Journal of Medicinal Chemistry, 2008, 43: 949-957.
Petursson et al., "Protecting Groups in Carbohydrate Chemistry," J. Chem. Educ., 1997, 74(11), 1297.
Piersanti et al., "Synthesis of Benzo[1,2-d;3,4-d']diimidazole and 1H-Pyrazolo[4,3-b]pyridine as Putative A2A Receptor Antagonists," Organic a& Biomolecular Chemistry, Jul. 13, 2007, 5:2567-2571.
Pinedo et al., "Translational Research: The Role of VEGF in Tumor Angiogenesis," The Oncologist, 2000, 5(suppl 1):1-2.
Pitt et al., "Heteroaromatic rings of the future," J Med Chem., May 14, 2009, 52(9):2952-2963.
Pozharskii et al., Heterocycles in Life and Society Wiley, 1997, pp. 1-6.
Remington's Pharmaceutical Sciences, 17th Ed., (Mack Publishing Company, Easton, 1985), p. 1418.
Sale et al., "Models of ovarian cancer metastasis: Murine models" Drug Discovery Today: Disease Models, 2006, 3:150-154.
Sanz-Garcia et al., "Current and advancing treatments for metastatic colorectal cancer," Expert Opinion on Biological Therapy, 2016, 16(1):93-110.
Sawasdikosol and Burakoff, "A perspective on HPK1 as a novel immuno-oncology drug target" eLife, 2020, 9:e55122.
Sawasdikosol et al., "HPK1 as a novel target for cancer immunotherapy," Immunologic Research, Apr. 4, 2012, 54(1-3): 262-265.
Sawasdikosol et al., "Hematopoietic progenitor kinase 1 (HPK1) influences regulatory T cell functions," The Journal of Immunology, 2012, 188(supplement 1):163, English Abstract.
Schober et al., "New Advances in the Treatment of Metastatic Pancreatic Cancer," Digestion, 2015, 92:175-184.
Sharma et al., "Cell line-based platforms to evaluate the therapeutic efficacy of candidate anticancer agents" Nature Reviews Cancer, Apr. 2010, 10:241-253.
Shaughnessy et al., "Copper-Catalyzed Amination of Aryl and Alkenyl Electrophiles," Organic Reactions, Chapter 1, 2014, 85: 1-668.
Shou et al., "Simple means to alleviate sensitivity loss by trifluoroacetic acid (TFA) mobile phases in the hydrophilic interaction chromatography—electrospray tandem mass spectrometric (HILIC-ESI/MS/MS) bioanalysis of basic compounds," J Chromatogr B Analyt Technol Biomed Life Sci., Oct. 25, 2005, 825:186-192.
Shui et al., "Hematopoietic progenitor kinase 1 negatively regulates T cell receptor signaling and T cell-mediated immune responses," Nat. Immunol., Jan. 2007, 8(1): 84-91.
Smyth et al., "Synthesis and reactivity of 3-amino-1H-pyrazolo[4,3-c]pyridin-4(5H)-ones: development of a novel kinase-focussed library," Tetrahedron, Apr. 2010, 66(15): 2843-2854.
Socinski et al., "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.
Subramanyam et al., "6-(4-Pyridinyl)-1H-1,2,3-triazolo[4,5-d]—pyrimidin-4(5H)-one: A Structurally Novel Competitive AMPA Receptor Antagonist," J Med Chem., 1995, 38(4):587-589.
Surry and Buchwald, "Dialkylbiaryl Phosphines in Pd-Catalyzed Amination: A User's Guide," Chem. Sci., 2011, 2(1): 27-50.
Taha et al., "Pharmacophore Modeling, Quantitative Structure-Activity Relationship Analysis, and in Silico Screening Reveal Potent Glycogen Synthase Kinase-3β Inhibitory Activities for Cimetidine, Hydroxychloroquine, and Gemifloxacin," J. Med. Chem., 2008, 51(7):2062-2077.
Taiwan Office Action in Taiwan Application No. 106130806, dated Aug. 3, 2021, 10 pages.
Terrett et al., "Sildenafil (VIAGRATM), a potent and selective inhibitor of type 5 cGMP phosphodiesterase with utility for the treatment of male erectile dysfunction," Bioorg & Med Chem Lett., Aug. 6, 1996, 6(15):1819-1824.
Thiriet, "Intracellular Signaling Mediators in the Circulatory and Ventilatory Systems," Springer New York, 2013, pp. 180-182.
Ukraine Office Action in Ukraine Application No. a201903484, dated Apr. 19, 2021, 7 pages.
Vaclavik et al., "Single-Laboratory Validation Study of a Method for Screening and Identification of Phosphodiesterase Type 5 Inhibitors in Dietary Ingredients and Supplements Using Liquid Chromatography/Quadrupole—Orbital Ion Trap Mass Spectrometry: First Action 2015.12," J AOAC Int., Jan.-Feb. 2016, 99(11):55-72.
Vymetalova et al., "5-Substituted 3-isopropyl-7-[4-(2-pyridyl)benzyl]amino-1(2)H-pyrazolo[4,3-d]pyrimidines with antiproliferative activity as potent and selective inhibitors of cyclin-dependent kinases," Eur J Med Chem., Mar. 3, 2016, 110:291-301.
Waddell et al., "Benzothiazolylthio Carbapenems: Potent Anti-MRSA Agents," Biorg & Med Chem Lett., 1995, 5(13):1427-1432.
Wang et al., "Activation of the hematopoietic progenitor kinase-1 (HPK1)—dependent, stress-activated c-Jun N-terminal kinase (JNK) pathway by transforming growth factor beta (TGF-beta)—activated kinase (TAK1), a kinase mediator of TGF beta signal transduction," J. Biol. Chem., Sep. 1997, 272(36): 22771-22775.
Wang et al., "Down-regulation of B cell receptor signaling by hematopoietic progenitor kinase 1 (HPK-1)—mediated phosphorylation and ubiquitination of activated B cell linker protein (BLNK)," J. Biol. Chem., Mar. 2012, 297(14): 11037-11048.
Wang et al., "Fragment-based identification and optimization of a class of potent pyrrolo[2,1-f][1,2,4]triazine MAP4K4 inhibitors," Boorg Med Chem Lett., 2014, 24(18):4546-4552.
Wang et al., "HPK1 positive expression associated with longer overall survival in patients with estrogen receptor-positive invasive ductal carcinoma—not otherwise specified," Mol Med Rep., Oct. 2017, 16(4):4634-4642.
Wang et al., "Synthesis and evaluation of human phosphodiesterases (PDE) 5 inhibitor analogs as trypanosomal PDE inhibitors. Part 1. Sildenafil analogs," Bioorg Med Chem Lett., Apr. 1, 2012, 22(7):2579-2581.
Weinmann et al., "Identification of lorazepam and sildenafil as examples for the application of LC/ionspray-MS and MS-MS with mass spectra library searching in forensic toxicology," Forensic Sci Int., Sep. 11, 2000, 113(1-3):339-344.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1577-1580.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1581-1584.

(56) References Cited

OTHER PUBLICATIONS

Wislicenus "Adolph Strecker's Short Textbook of Organic Chemistry," 1881, Spottiswood, London, pp. 38-39.
Xu et al., "Design, synthesis and biological evaluation of euterated nintedanib for improving pharmacokinetic properties," J. Labelled Comp. Radiopharm., Jun. 2015, 58(7): 308-312.
Yang et al., "Highly efficient synthesis of fused bicyclic 2,3-diarylpyrimidin-4(3H)—ones via Lewis acid assisted cyclization reaction," Tetrahedron Letters, Mar. 10, 2008, 49(11):1725-1728.
Yeo et al., "New metabolites of hongdenafil, homosildenafil and hydroxyhomosildenafil," J Pharm Biomed Anal., Feb. 5, 2018, 149:586-590.
Zhang et al., "Anti-angiogenic effects of novel cyclin-dependent kinase inhibitors with a pyrazolo[4,3-d]pyrimidine scaffold," Br J Pharmacol., Sep. 2016, 173(17):2645-2656.
Zhou et al., "Hematopoietic progenitor kinase 1 is a component of transforming growth factor beta-induced c-Jun N-terminal kinase signaling cascade," J. Biol. Chem., May 1999, 274(19): 13133-13138.
Zhu et al., "Design and Synthesis of Pyridine—pyrazolopyridine based inhibitors of protein kinase B/Akt," Bioorganic and Medicinal Chemistry, Jan. 17, 2007, 15: 2441-2452.
Zhu et al., "Characterization of TPN729 metabolites in humans using ultra-performance liquid chromatography/quadrupole time-of-flight mass spectrometry," J Pharm Biomed Anal., Jan. 5, 2016, 117:217-226.
Zhu et al., "Syntheses of potent, selective, and orally bioavailable indazole-pyridine series of protein kinase B/Akt inhibitors with reduced hypotension," J Med Chem., Jun. 28, 2007, 50(13):2990-3003.
Literature and Patent Chemical Structure Search, Science IP, The CAS Search Service, Jul. 1, 2016, 441 pages.
Literature and Patent Chemical Structure Search, Science IP, The CAS Search Service, Jun. 30, 2016, 200 pages.
Structure 4: Substance Search Patent and Non-Patent Databases, Science IP, The CAS Search Service, Jun. 8, 2016, 820 pages.
Structure 3: Substance Search Patent and Non-Patent Databases, Science IP, The CAS Search Service, Jun. 7, 2016, 512 pages.
Structure 2: Substance Search Patent and Non-Patent Databases, Science IP, The CAS Search Service, Jun. 7, 2016, 833 pages.
Structure 1: Substance Search Patent and Non-Patent Databases, Science IP, The CAS Search Service, Jun. 6, 2016, 583 pages.
STN Search Report dated Aug. 17, 2016, 157 pages.
STN Search Report dated Aug. 25, 2016, 25 pages.
STN Search Report dated Aug. 30, 2016, 31 pages.
STN Search Report dated Aug. 31, 2016, 32 pages.
STN Search Report dated Jan. 27, 2017, 94 pages.
STN Search Report dated Jan. 22, 2018, 9 pages.
STN Search Report dated Sep. 5, 2017, 26 pages.
STN Search Report dated Sep. 5, 2017, 5 pages.
STN Search Report dated Jan. 23, 2018, 26 pages.
STN Search Report dated Apr. 25, 2018, 19 pages.
STN Search Report dated Apr. 9, 2018, 7 pages.
STN Search Report dated May 9, 2018, 16 pages.
Indian Office Action in Indian Application No. 202017040632, dated Mar. 7, 2022, 7 pages.
International Preliminary Report on Patentability in International Application No. PCT/US2020/044919, dated Feb. 8, 2022, 9 pages.
Caira, "Crystalline polymorphism of organic compounds," Topics in current chemistry, Jan. 1998, 198:163-208.
Chinese Office Action in Chinese Application No. 201980020899.4, dated Dec. 22, 2022, 11 pages (with English translation).
Colombian Office Action in Colombian Application No. NC2020/0011530, dated Oct. 26, 2022, 19 pages (with English translation).
Eurasian Office Action in Eurasian Application No. 202290492, dated Jan. 9, 2023, 9 pages (with English translation).
Extended European Search Report in European Application No. 22177485.4, dated Dec. 19, 2022, 8 pages.
Japanese Office Action in Japanese Application No. 2020-566534, dated Jan. 31, 2023, 6 pages (with English translation).
Taiwanese Office Action in Taiwanese Application No. 111124255, dated Jan. 31, 2023, 11 pages (with English translation).
Zhang et al., "Interactions between hematopoietic progenitor kinase 1 and its adaptor proteins (Review)," Molecular Medicine Reports, Sep. 2017, 16:6472-6482.

SOLID FORMS OF AN HPK1 INHIBITOR

FIELD OF THE INVENTION

The present invention relates to salt forms of the hematopoietic progenitor kinase 1 (HPK1) inhibitors N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide and N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide, including methods of preparation thereof, wherein the compounds are useful in the treatment of HPK1 mediated diseases such as cancer.

BACKGROUND OF THE INVENTION

Hematopoietic progenitor kinase 1 (HPK1) originally cloned from hematopoietic progenitor cells is a member of MAP kinase kinase kinase kinases (MAP4Ks) family, which includes MAP4K1/HPK1, MAP4K2/GCK, MAP4K3/GLK, MAP4K4/HGK, MAP4K5/KHS, and MAP4K6/MINK (Hu, M. C., et al., Genes Dev, 1996. 10(18): p. 2251-64). HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-β3R) (Wang, W., et al., J Biol Chem, 1997. 272(36): p. 22771-5; Zhou, G., et al., J Biol Chem, 1999. 274(19): p. 13133-8), or $G_s$-coupled $PGE_2$ receptors (EP2 and EP4) (Ikegami, R., et al., J Immunol, 2001. 166(7): p. 4689-96). As such, HPK1 regulates diverse functions of various immune cells.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48). HPK1 knockout mice were more susceptible to the induction of experimental autoimmune encephalomyelitis (EAE) (Shui, J. W., et al., Nat Immunol, 2007. 8(1): p. 84-91). In human, HPK1 was downregulated in peripheral blood mononuclear cells of psoriatic arthritis patients or T cells of systemic lupus erythematosus (SLE) patients (Batliwalla, F. M., et al., Mol Med, 2005. 11(1-12): p. 21-9). Those observations suggested that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice (see US 2007/0087988). In addition, it was shown that adoptive transfer of HPK1 deficient T cells was more effective in controlling tumor growth and metastasis than wild-type T cells (Alzabin, S., et al., Cancer Immunol Immunother, 2010. 59(3): p. 419-29). Similarly, BMDCs from HPK1 knockout mice were more efficient to mount a T cell response to eradicate Lewis lung carcinoma as compared to wild-type BMDCs (Alzabin, S., et al., J Immunol, 2009. 182(10): p. 6187-94). These data, in conjunction with the restricted expression of HPK1 in hematopoietic cells and lack of effect on the normal development of immune cells, suggest that HPK1 is a drug target for enhancing antitumor immunity.

Inhibitors of HPK1 are currently being developed for the treatment of cancer. For example, the molecules N-(2-((2S,4S)-4-amino-2-(hydroxymethyl)pyrrolidin-1-yl)-5-fluorophenyl)-2-(2-fluoro-6-methoxyphenyl)pyrimidine-4-carboxamide and N-(2-((2S,4S)-4-amino-2-(hydroxymethyl)pyrrolidin-1-yl)-4-(4-cyanopyridin-3-yl)phenyl)-2-(2-fluoro-6-methoxyphenyl)pyrimidine-4-carboxamide, and other small molecule inhibitors of HPK1 are reported in e.g., U.S. patent application Ser. No. 16/278,865 (published as US Patent Publication No. 2019/0382380). Accordingly, there is a need for new solid forms and salts of HPK1-inhibiting molecules for preparing pharmaceutically useful formulations and dosage forms with suitable properties related to, for example, facilitating the manufacture of safe, effective, and high quality drug products.

SUMMARY OF THE INVENTION

The present invention is directed to solid forms of N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide (Compound 1) and salts thereof.

The present invention is further directed to salts of Compound 1. The present invention is further directed to the phosphoric acid salt of Compound 1, the hydrochloric acid salt of Compound 1, the L-(+)-tartaric acid salt of Compound 1, the malic acid salt of Compound 1, the camphorsulfonic acid salt of Compound 1, the mandelic acid salt of Compound 1, and the citric acid salt of Compound 1.

The present invention is directed to solid forms of N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide (Compound 2) and salts thereof.

The present invention is further directed to salts of Compound 2. The present invention is further directed to the phosphoric acid salt of Compound 2 and the hydrochloric acid salt of Compound 2.

The present invention is further directed to crystalline forms of the salts described herein. The present invention is further directed to pharmaceutical compositions comprising a salt or crystalline form described herein, and at least one pharmaceutically acceptable carrier.

The present invention is further directed to therapeutic methods of using the salts and solid forms described herein. The present disclosure also provides uses of the salts and solid forms described herein in the manufacture of a medicament for use in therapy. The present disclosure also provides the salts and solid forms described herein for use in therapy.

The present invention is further directed to processes for preparing the salts and solid forms described herein.

DETAILED DESCRIPTION

Figure 1:
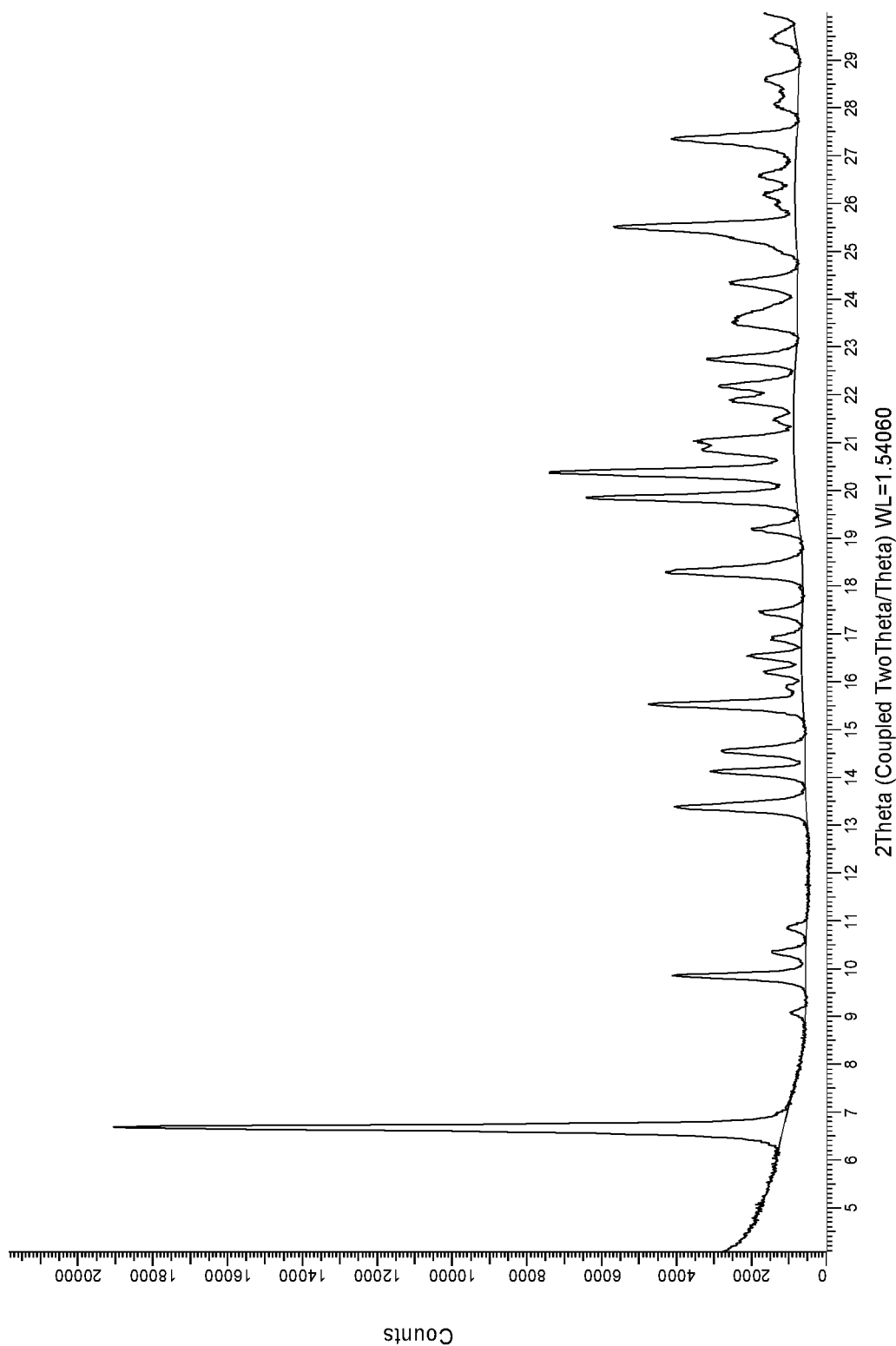
FIG. 1 shows an XRPD pattern of Compound 1 Form I.

The present invention is directed to, inter alia, solid forms of N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide (Compound 1) and salts thereof, the structure of which is shown below.

Compound 1

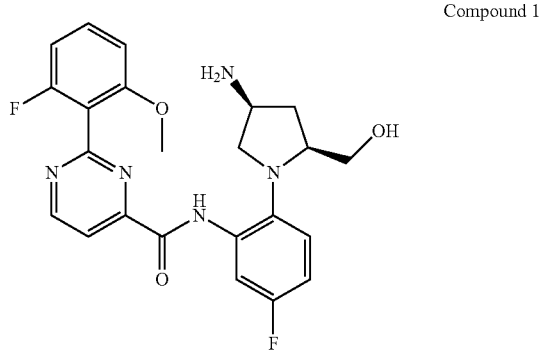 [SMILES: COc1cccc(F)c1-c1nccc(C(=O)Nc2cc(F)ccc2N2C[C@@H](N)C[C@H]2CO)n1]

Compound 1 is described in U.S. patent application Ser. No. 16/278,865 (published as US Patent Publication No. 2019/0382380), the entirety of which is incorporated herein by reference.

Compound 1 and its salts can be isolated as one or more solid forms. The solid forms (e.g., crystalline forms) described herein have many advantages, for example they have desirable properties, such as ease of handling, ease of processing, storage stability, and ease of purification. Moreover, the crystalline forms can be useful for improving the performance characteristics of a pharmaceutical product such as dissolution profile, shelf-life and bioavailability. For example, the citric acid salt of Compound 1 is advantageous because it is highly crystalline, isolable as a single polymorph, non-hygroscopic, stable in aqueous formulations, and can be made reproducibly.

In some embodiments, the salt of Compound 1 is an acid salt of Compound 1. In some embodiments, the acid is selected from phosphoric acid, hydrochloric acid, L-(+)-tartaric acid, malic acid, camphorsulfonic acid, mandelic acid, and citric acid.

In some embodiments, the salt of the invention is a phosphoric acid salt of Compound 1. The phosphoric acid salt form of Compound 1 is referred to herein as "Compound 1 phosphate salt," "Compound 1 phosphoric acid salt form," "Compound 1 phosphoric acid," or "Compound 1 phosphate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide phosphate.

In some embodiments, the salt of the invention is a hydrochloric acid salt of Compound 1. The hydrochloric acid salt form of Compound 1 is referred to herein as "Compound 1 hydrochloride salt," "Compound 1 hydrochloric acid salt form," "Compound 1 hydrochloric acid," or "Compound 1 hydrochloride." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide hydrochloride.

In some embodiments, the salt of the invention is a L-(+)-tartaric acid salt of Compound 1. The L-(+)-tartaric acid salt form of Compound 1 is referred to herein as "Compound 1 L-tartrate salt," "Compound 1 L-(+)-tartaric acid salt form," "Compound 1 L-(+)-tartaric acid," or "Compound 1 L-tartrate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide L-tartrate.

In some embodiments, the salt of the invention is a malic acid salt (e.g., L-(−)-malic acid salt) of Compound 1. The malic acid salt form of Compound 1 is referred to herein as "Compound 1 malate salt," "Compound 1 L-malate salt," "Compound 1 malic acid salt form," "Compound 1 malic acid," "Compound 1 malate," or "Compound 1 L-malate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide malate.

In some embodiments, the salt of the invention is a camphorsulfonic acid salt of Compound 1. The camphorsulfonic acid salt form of Compound 1 is referred to herein as "Compound 1 camsylate salt," "Compound 1 camphorsulfonic acid salt form," "Compound 1 (1S)-(+)-10-camphorsulfonic acid," "Compound 1 camphorsulfonic acid," or "Compound 1 camsylate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide camsylate.

In some embodiments, the salt of the invention is a mandelic acid salt of Compound 1. The mandelic acid salt form of Compound 1 is referred to herein as "Compound 1 mandelate salt," "Compound 1 mandelic acid salt form," "Compound 1 mandelic acid," "Compound 1 (S)-(+)-mandelic acid," "Compound 1 mandelate," or "Compound 1 (S)-(+)-mandelate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide mandelate.

In some embodiments, the salt of the invention is a citric acid salt of Compound 1. The citric acid salt form of Compound 1 is referred to herein as "Compound 1 citrate salt," "Compound 1 citric acid salt form," "Compound 1 citric acid," or "Compound 1 citrate." An alternative name for the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide citrate.

The present invention is directed to, inter alia, solid forms of N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide (Compound 2) and salts thereof, the structure of which is shown below.

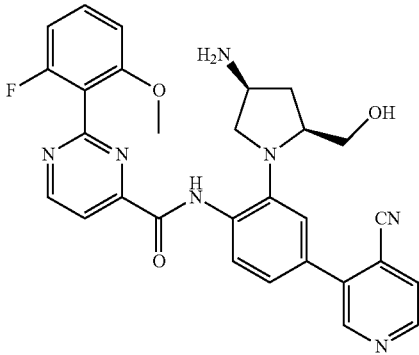

Compound 2

Compound 2 is described in U.S. patent application Ser. No. 16/278,865 (published as US Patent Publication No. 2019/0382380), the entirety of which is incorporated herein by reference.

Compound 2 and its salts can be isolated as one or more solid forms. The solid forms (e.g., crystalline forms) described herein have many advantages, for example they have desirable properties, such as ease of handling, ease of processing, storage stability, and ease of purification. Moreover, the crystalline forms can be useful for improving the performance characteristics of a pharmaceutical product such as dissolution profile, shelf-life and bioavailability. For example, the phosphoric acid salt of Compound 2 (e.g., the dihydrate phosphoric acid salt of Compound 2) is advantageous because it is highly crystalline, isolable as a single polymorph, non-hygroscopic, stable in aqueous formulations, and can be made reproducibly.

In some embodiments, the salt of Compound 2 is an acid salt of Compound 2. In some embodiments, the acid is selected from phosphoric acid and hydrochloric acid.

In some embodiments, the salt of the invention is a phosphoric acid salt of Compound 2. The phosphoric acid salt form of Compound 2 is referred to herein as "Compound 2 phosphate salt," "Compound 2 phosphoric acid salt form," "Compound 2 phosphoric acid," or "Compound 2 phosphate." An alternative name for the salt is N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide phosphate.

In some embodiments, the salt of the invention is a hydrochloric acid salt of Compound 2. The hydrochloric acid salt form of Compound 2 is referred to herein as "Compound 2 hydrochloride salt," "Compound 2 hydrochloric acid salt form," "Compound 2 hydrochloric acid," or "Compound 2 hydrochloride." An alternative name for the salt is N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide hydrochloride.

The salts of the invention can be isolated as one or more solid forms. As used herein, the phrase "solid form" refers to a salt of the invention in either an amorphous state or a crystalline state ("crystalline form" or "crystalline solid"), whereby a salt of the invention in a crystalline state may optionally include solvent or water within the crystalline lattice, for example, to form a solvated or hydrated crystalline form. In some embodiments, the salt of the present invention is in a crystalline state as described herein. The term "hydrated," as used herein, is meant to refer to a crystalline form that includes one or more water molecules in the crystalline lattice. Example "hydrated" crystalline forms include hemihydrates, monohydrates, dihydrates, and the like. Other hydrated forms such as channel hydrates and the like are also included within the meaning of the term.

In some embodiments, salts of the invention can be prepared by any suitable method for the preparation of acid addition salts. For example, the free base of a compound (e.g., Compound 1 or Compound 2) can be combined with the desired acid in a solvent or in a melt. Alternatively, an acid addition salt of a compound can be converted to a different acid addition salt by anion exchange. Salts of the invention which are prepared in a solvent system can be isolated by precipitation from the solvent. Precipitation and/or crystallization can be induced, for example, by evaporation, reduction of temperature, addition of anti-solvent, or combinations thereof.

In some embodiments, the salts of the invention are crystalline, including crystalline forms which are anhydrous, hydrated, non-solvated, or solvated. Example hydrates include hemihydrates, monohydrates, dihydrates, and the like. In some embodiments, the crystalline salts are anhydrous and non-solvated. By "anhydrous" is meant that the crystalline salt contains no bound water in the crystal lattice structure, i.e., the compound does not form a crystalline hydrate.

In some embodiments, the salts of the invention are substantially isolated. By "substantially isolated" is meant that the salt is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the salt.

The salt forms of the invention were found to be highly crystalline, a desirable property which can facilitate, for example, purification of the drug such as by crystallization and recrystallization as necessary. Further, a crystalline form tends to be more stable and can be easier to mill or micronize when formulating a drug. Crystalline salts also tend have excellent properties with respect to solubility and can be more suitable to be manufactured reproducibly in a clear acid/base ratio, facilitating the preparation of liquid formulations for oral as well as for intravenous applications.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystals. As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

As used herein, the term "substantially crystalline," means a majority of the weight of a sample or preparation of a salt (or hydrate or solvate thereof) of the invention is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±3° C. Accordingly, a crystalline form reported herein having a DSC thermogram "substantially" as shown in any of the Figures is understood to accommodate such variation.

The salts and compounds disclosed herein can include all isotopes of atoms occurring within them. Isotopes include those atoms having the same atomic number but different mass numbers. For example, isotopes of hydrogen include tritium and deuterium. Salts and compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}C$ NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.2 degrees 2-theta.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "melting point" refers to an endothermic event or endothermal event observed in e.g., a DSC experiment. An endothermic event is a process or reaction in which a sample absorbs energy from its surrounding in the form of e.g., heat as in a DSC experiment. An exothermic event is a process or reaction in which a sample releases energy. The process of heat absorption and release can be detected by DSC. In some embodiments, the term "melting point" is used to describe the major endothermic event revealed on a particular DSC thermogram.

The term "room temperature" as used herein, is understood in the art, and refers generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

Solid Forms of Compound 1

Compound 1 Form I

Provided herein is a solid form of Compound 1 which is crystalline, referred to as Form I, which is described below in the Examples.

Provided herein are also processes for preparing Form I of Compound 1 comprising recrystallizing Compound 1 in a solvent. In some embodiments, the solvent is a polar solvent. In some embodiments, the solvent is $C_{1-6}$ alkyl alcohol solvent. In some embodiments, the solvent is isopropyl alcohol.

In some embodiments, Form I has at least one characteristic XRPD peak selected from about 6.7, about 9.9, about 13.4, and about 15.5 degrees 2-theta. In some embodiments, Form I has at least two characteristic XRPD peaks selected from about 6.7, about 9.9, about 13.4, and about 15.5 degrees 2-theta. In some embodiments, Form I has at least three characteristic XRPD peaks selected from about 6.7, about 9.9, about 13.4, and about 15.5 degrees 2-theta. In some embodiments, Form I has a XRPD peak at about 6.7 degrees 2-theta. In some embodiments, Form I has a XRPD peak at about 9.9 degrees 2-theta. In some embodiments, Form I has a XRPD peak at about 13.4 degrees 2-theta. In some embodiments, Form I has a XRPD peak at about 15.5 degrees 2-theta.

In some embodiments, Form I has at least one characteristic XRPD peak selected from about 6.7, about 9.9, about 13.4, about 14.1, about 15.5, about 18.3, about 19.9, and about 20.4 degrees 2-theta. In some embodiments, Form I has at least two characteristic XRPD peaks selected from about 6.7, about 9.9, about 13.4, about 14.1, about 15.5, about 18.3, about 19.9, and about 20.4 degrees 2-theta. In some embodiments, Form I has at least three characteristic XRPD peaks selected from about 6.7, about 9.9, about 13.4, about 14.1, about 15.5, about 18.3, about 19.9, and about 20.4 degrees 2-theta.

In some embodiments, Form I has at least one characteristic XRPD peak selected from about 6.7, about 9.9, about 13.4, about 14.1, about 14.6, about 15.5, about 18.3, about 19.9, about 20.4, about 21.0, about 22.8, and about 25.5 degrees 2-theta. In some embodiments, Form I has at least two characteristic XRPD peaks selected from about 6.7, about 9.9, about 13.4, about 14.1, about 14.6, about 15.5, about 18.3, about 19.9, about 20.4, about 21.0, about 22.8, and about 25.5 degrees 2-theta. In some embodiments, Form I has at least three characteristic XRPD peaks selected from about 6.7, about 9.9, about 13.4, about 14.1, about 14.6, about 15.5, about 18.3, about 19.9, about 20.4, about 21.0, about 22.8, and about 25.5 degrees 2-theta.

In some embodiments, Form I has an XRPD pattern with characteristic peaks as substantially shown in FIG. 1.

Figure 2:
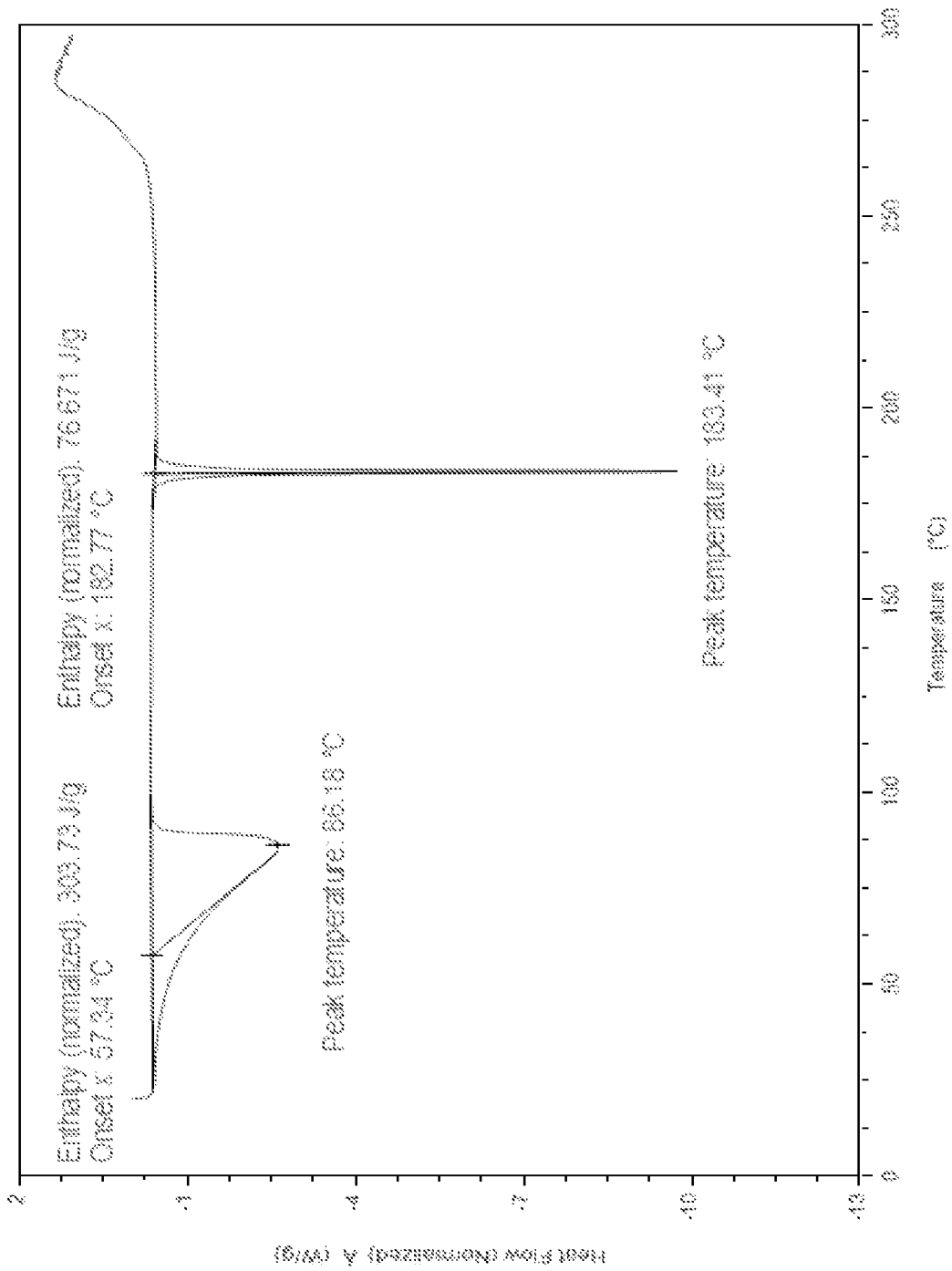
FIG. 2 shows a DSC thermogram of Compound 1 Form I.
Figure 3:
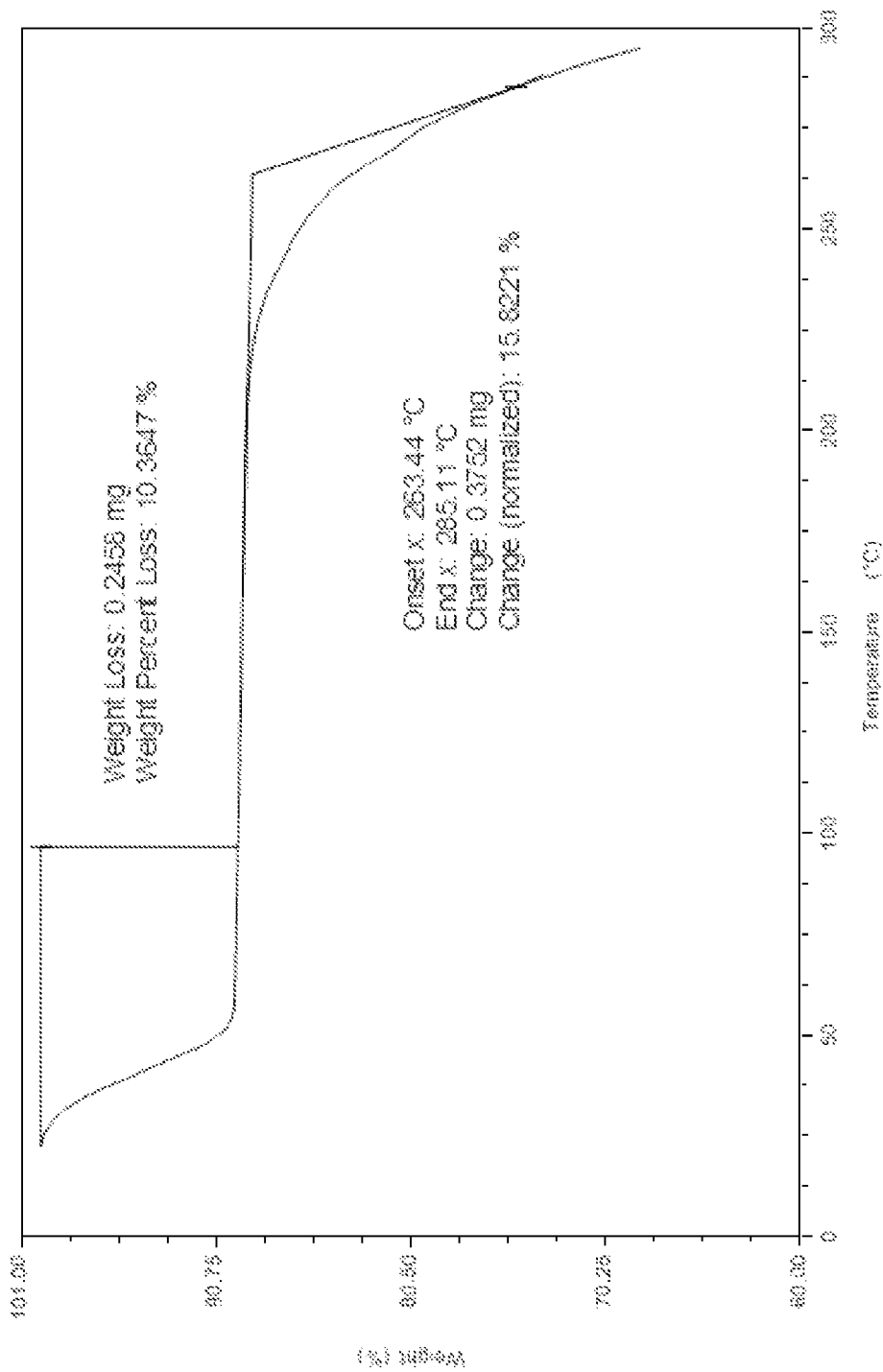
FIG. 3 shows a TGA thermogram of Compound 1 Form I.

In some embodiments, Form I exhibits a DSC thermogram having endotherm peaks at temperatures of about 86° C. and about 183° C. In some embodiments, Form I exhibits a DSC thermogram having an endotherm peak at a temperature of about 86° C. In some embodiments, Form I exhibits a DSC thermogram having an endotherm peak at a temperature of about 183° C. In some embodiments, Form I has a DSC thermogram substantially as depicted in FIG. 2. In some embodiments, Form I has a TGA thermogram substantially as depicted in FIG. 3.

In some embodiments, Form I has at least one characteristic XRPD peak selected from about 6.7, about 9.9, about 13.4, and about 15.5 degrees 2-theta; and Form I exhibits a DSC thermogram having endotherm peaks at temperatures of about 86° C. and about 183° C. In some embodiments, Form I has at least one characteristic XRPD peak selected from about 6.7, about 9.9, about 13.4, and about 15.5 degrees 2-theta; and Form I exhibits a DSC thermogram having an endotherm peak at a temperatures of about 86° C. In some embodiments, Form I has at least one characteristic XRPD peak selected from about 6.7, about 9.9, about 13.4, and about 15.5 degrees 2-theta; and Form I exhibits a DSC thermogram having an endotherm peak at a temperatures of about 183° C.

In some embodiments, Form I can be isolated with a purity of at least about 80%, about 85%, about 90%, about 95%, about 96%, about 97%, about 98%, or about 99%. In some embodiments, Form I can be isolated with a purity greater than about 99%.

Phosphoric Acid Salts

The phosphoric acid salt of Compound 1 can be prepared by any suitable method for preparation of phosphoric acid addition salts. For example, Compound 1 can be combined with phosphoric acid (e.g., about 1.0 molar eq or more) in a solvent and the resulting salt can be isolated by filtering the salt from solution. In certain embodiments, Compound 1 is combined with about 1 to about 2 molar equivalents of phosphoric acid. In certain embodiments, Compound 1 is combined with about 1 to about 1.5 molar equivalents of phosphoric acid. In certain embodiments, Compound 1 is combined with about 1.05 molar equivalents of phosphoric acid. In some embodiments, the solvent is a polar solvent. In some embodiments, the solvent is a $C_{1-6}$ alkyl alcohol. In some embodiments, the solvent is methanol.

The phosphoric acid salt of Compound 1 can be crystallized to provide a crystalline solid form. In some embodiments, the crystallization of the phosphoric acid salt of Compound 1 comprises precipitating the phosphoric acid salt of Compound 1 from a crystallizing solvent. In some embodiments, the crystallizing solvent is a polar solvent. In some embodiments, the crystallizing solvent is water.

In some embodiments, the phosphoric acid salt of Compound 1 has at least one characteristic XRPD peak selected from about 6.4, about 7.0, about 11.2, and about 12.5 degrees 2-theta. In some embodiments, the phosphoric acid salt of Compound 1 has at least two characteristic XRPD peaks selected from about 6.4, about 7.0, about 11.2, and about 12.5 degrees 2-theta. In some embodiments, the phosphoric acid salt of Compound 1 has at least three characteristic XRPD peaks selected from about 6.4, about 7.0, about 11.2, and about 12.5 degrees 2-theta. In some embodiments, the phosphoric acid salt of Compound 1 has a characteristic XRPD peak at about 6.4 degrees 2-theta. In some embodiments, the phosphoric acid salt of Compound 1 has a characteristic XRPD peak at about 7.0 degrees 2-theta. In some embodiments, the phosphoric acid salt of Compound 1 has a characteristic XRPD peak at about 11.2 degrees 2-theta. In some embodiments, the phosphoric acid salt of Compound 1 has a characteristic XRPD peak at about 12.5 degrees 2-theta.

In some embodiments, the phosphoric acid salt of Compound 1 has at least one characteristic XRPD peak selected from about 6.3, about 6.4, about 7.0, about 8.9, about 11.2, about 12.5, about 19.9, and about 22.9 degrees 2-theta. In some embodiments, the phosphoric acid salt of Compound 1 has at least two characteristic XRPD peaks selected from about 6.3, about 6.4, about 7.0, about 8.9, about 11.2, about 12.5, about 19.9, and about 22.9 degrees 2-theta. In some embodiments, the phosphoric acid salt of Compound 1 has at least three characteristic XRPD peaks selected from about 6.3, about 6.4, about 7.0, about 8.9, about 11.2, about 12.5, about 19.9, and about 22.9 degrees 2-theta.

In some embodiments, the phosphoric acid salt of Compound 1 has at least one characteristic XRPD peak selected from about 6.3, about 6.4, about 7.0, about 8.9, about 11.2, about 12.5, about 15.8, about 17.0, about 18.0, about 19.9, about 22.9, about 24.5, and about 25.2 degrees 2-theta. In some embodiments, the phosphoric acid salt of Compound 1 has at least two characteristic XRPD peaks selected from about 6.3, about 6.4, about 7.0, about 8.9, about 11.2, about 12.5, about 15.8, about 17.0, about 18.0, about 19.9, about 22.9, about 24.5, and about 25.2 degrees 2-theta. In some embodiments, the phosphoric acid salt of Compound 1 has at least three characteristic XRPD peaks selected from about 6.3, about 6.4, about 7.0, about 8.9, about 11.2, about 12.5, about 15.8, about 17.0, about 18.0, about 19.9, about 22.9, about 24.5, and about 25.2 degrees 2-theta.

Figure 4:
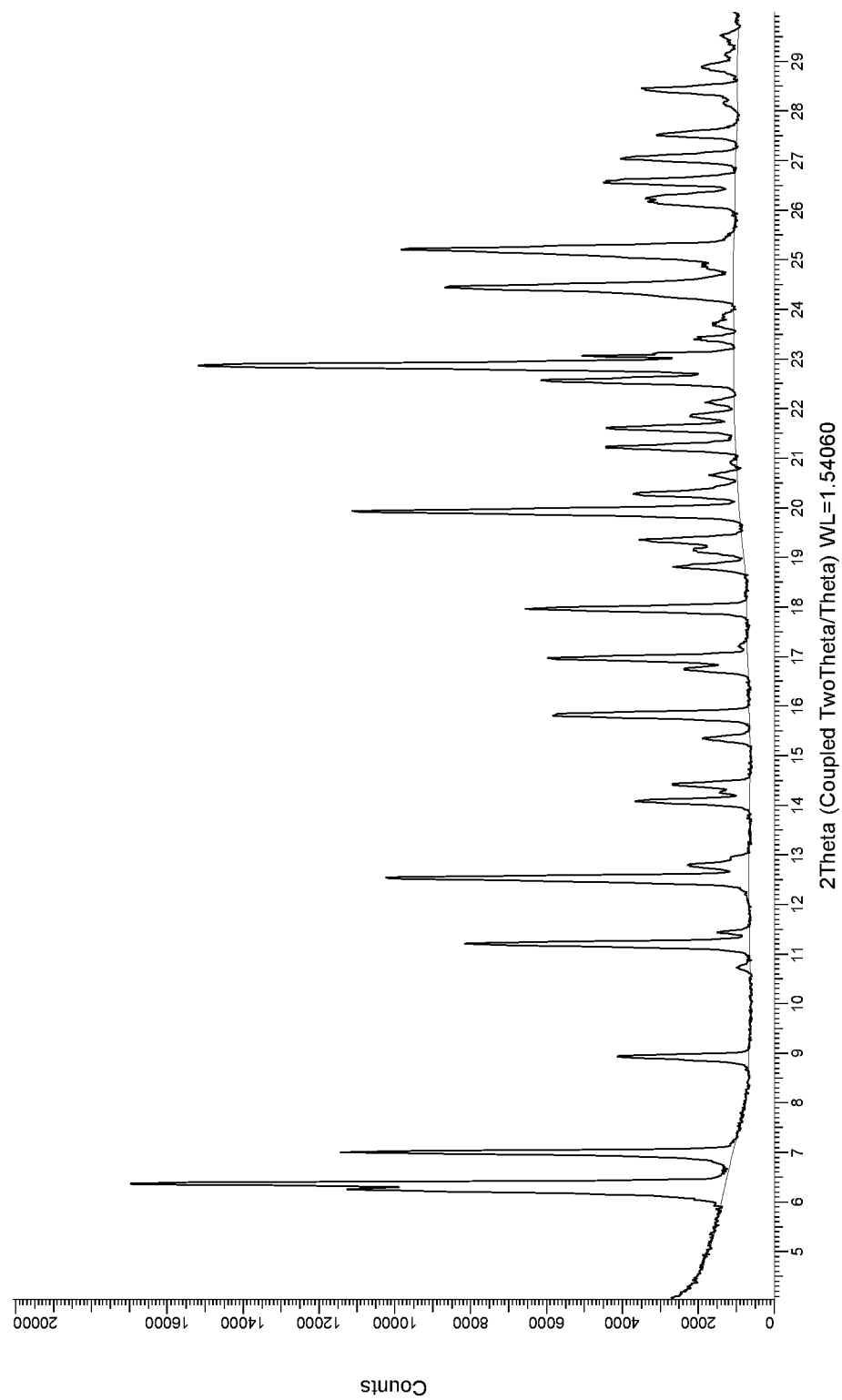
FIG. 4 shows an XRPD pattern of Compound 1 phosphate.

In some embodiments, the phosphoric acid salt of Compound 1 has an XRPD pattern with characteristic peaks as substantially shown in FIG. 4.

Figure 5:
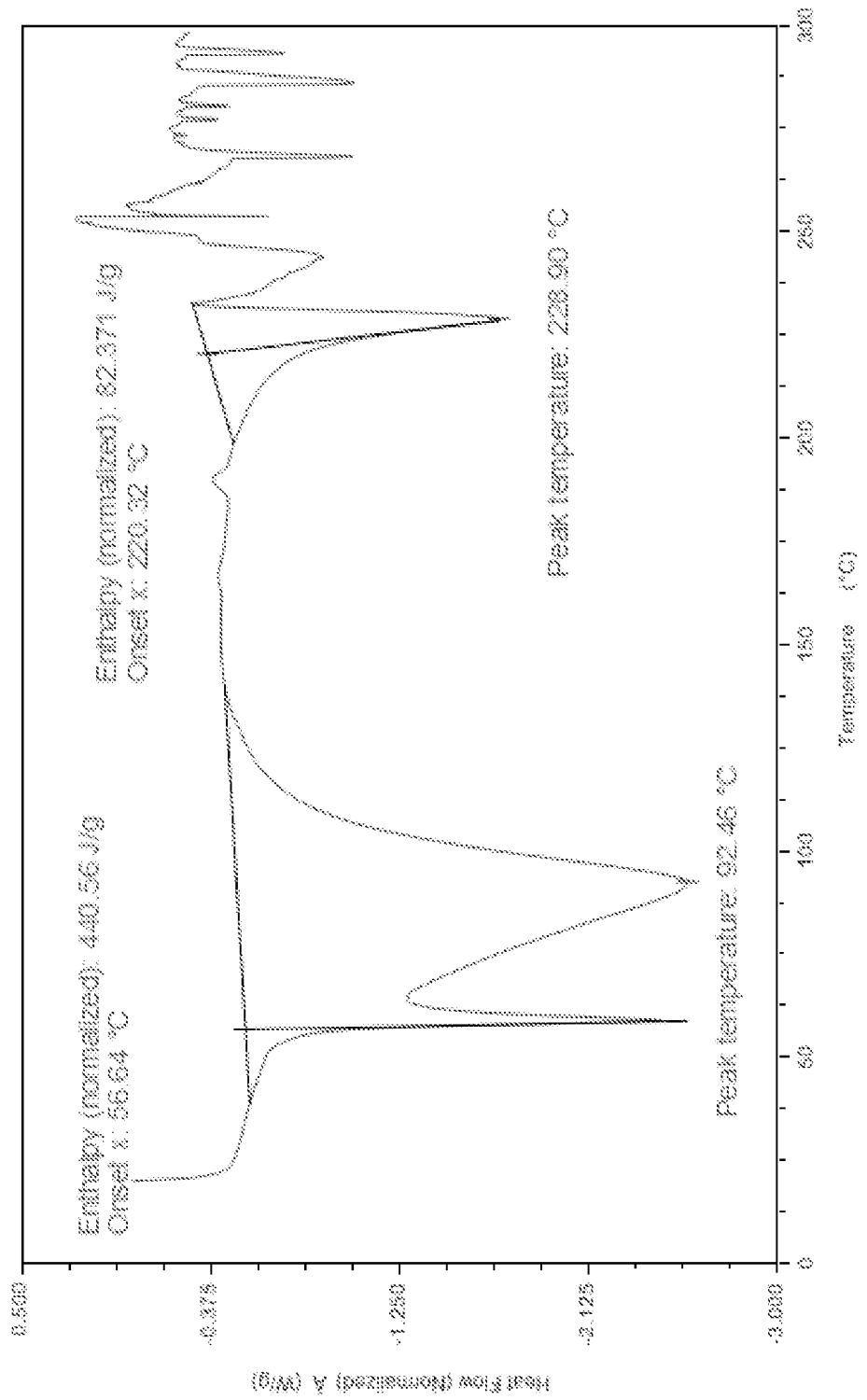
FIG. 5 shows a DSC thermogram of Compound 1 phosphate.
Figure 6:
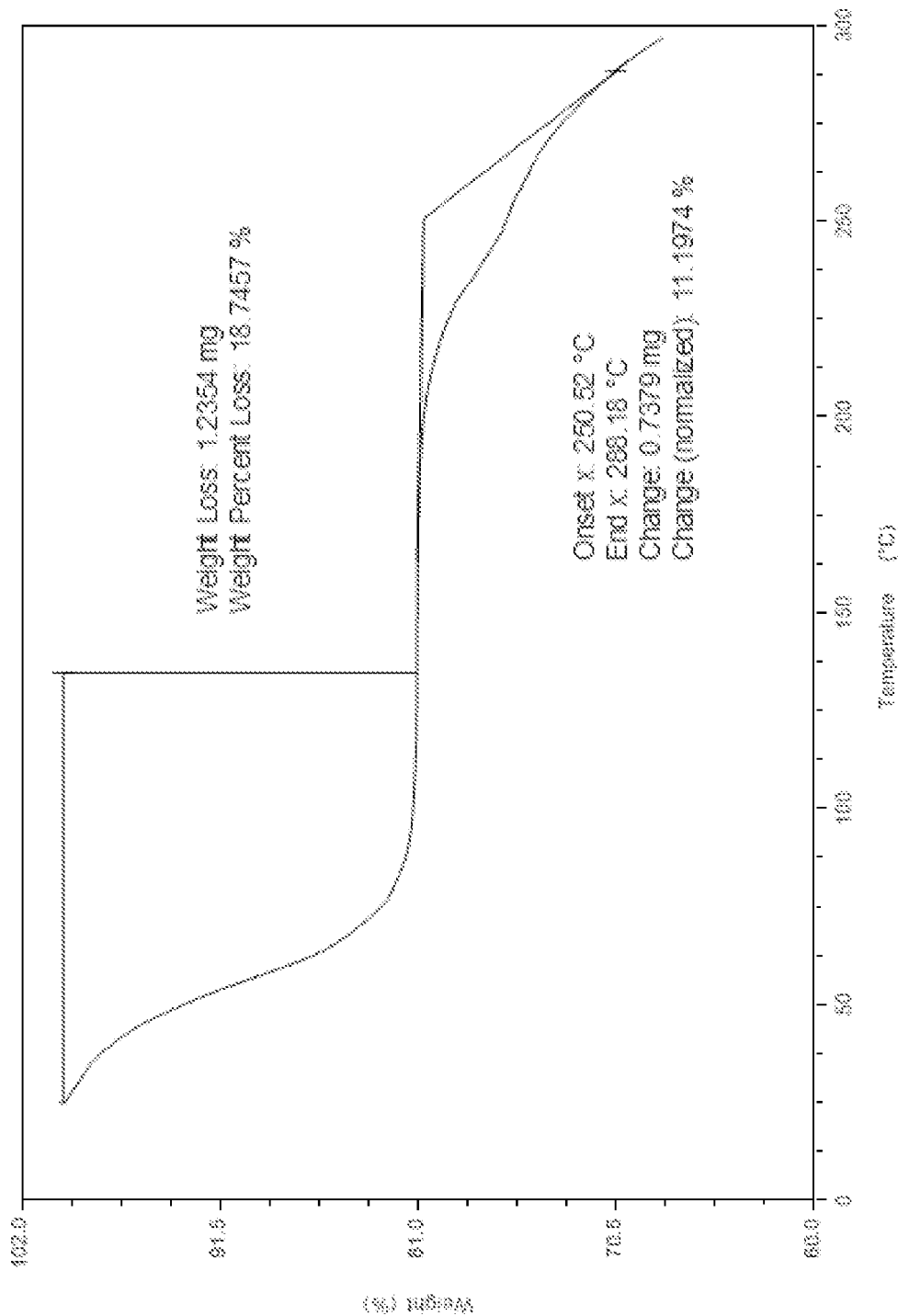
FIG. 6 shows a TGA thermogram of Compound 1 phosphate.

In some embodiments, the phosphoric acid salt of Compound 1 exhibits a DSC thermogram having endothermic peaks at temperatures of about 92° C. and about 229° C. In some embodiments, the phosphoric acid salt of Compound 1 exhibits a DSC thermogram having an endothermic peak at a temperature of about 92° C. In some embodiments, the phosphoric acid salt of Compound 1 exhibits a DSC thermogram having an endothermic peak at a temperature of about 229° C. In some embodiments, the phosphoric acid salt of Compound 1 has a DSC thermogram substantially as depicted in FIG. 5. In some embodiments, the phosphoric acid salt of Compound 1 has a TGA thermogram substantially as depicted in FIG. 6.

In some embodiments, the phosphoric acid salt of Compound 1 has at least one characteristic XRPD peak selected from about 6.4, about 7.0, about 11.2, and about 12.5 degrees 2-theta; and the phosphoric acid salt exhibits a DSC thermogram having endothermic peaks at temperatures of about 92° C. and about 229° C. In some embodiments, the phosphoric acid salt of Compound 1 has at least one characteristic XRPD peak selected from about 6.4, about 7.0, about 11.2, and about 12.5 degrees 2-theta; and the phosphoric acid salt exhibits a DSC thermogram having an endothermic peak at a temperature of about 92° C. In some embodiments, the phosphoric acid salt of Compound 1 has at least one characteristic XRPD peak selected from about 6.4, about 7.0, about 11.2, and about 12.5 degrees 2-theta; and the phosphoric acid salt exhibits a DSC thermogram having an endothermic peak at a temperature of about 229° C.

In some embodiments, the phosphoric acid salt of Compound 1 is substantially crystalline. In some embodiments, the salt is crystalline.

Hydrochloric Acid Salts

The hydrochloric acid salt of Compound 1 can be prepared by any suitable method for preparation of hydrochloric acid addition salts. For example, Compound 1 can be combined with hydrochloric acid (e.g., about 1.0 molar eq or more) in a solvent and the resulting salt can be isolated by filtering the salt from solution. In certain embodiments, Compound 1 is combined with about 1 to about 2 molar equivalents of hydrochloric acid. In certain embodiments, Compound 1 is combined with about 1 to about 1.5 molar equivalents of hydrochloric acid. In certain embodiments, Compound 1 is combined with about 1.05 molar equivalents of hydrochloric acid. In some embodiments, the solvent is a polar solvent. In some embodiments, the solvent is a $C_{1-6}$ alkyl alcohol. In some embodiments, the solvent is methanol.

The hydrochloric acid salt of Compound 1 can be crystallized to provide a crystalline solid form. In some embodiments, the crystallization of the hydrochloric acid salt of Compound 1 comprises precipitating the hydrochloric acid salt of Compound 1 from a crystallizing solvent. In some embodiments, the crystallizing solvent is a polar solvent. In some embodiments, the crystallizing solvent is water.

In some embodiments, the hydrochloric acid salt of Compound 1 has at least one characteristic XRPD peak selected from about 6.7, about 9.1, about 13.5, and about 15.5 degrees 2-theta. In some embodiments, the hydrochloric acid salt of Compound 1 has at least two characteristic XRPD peaks selected from about 6.7, about 9.1, about 13.5, and about 15.5 degrees 2-theta. In some embodiments, the hydrochloric acid salt of Compound 1 has at least three characteristic XRPD peaks selected from about 6.7, about 9.1, about 13.5, and about 15.5 degrees 2-theta. In some embodiments, the hydrochloric acid salt of Compound 1 has a characteristic XRPD peak at about 6.7 degrees 2-theta. In some embodiments, the hydrochloric acid salt of Compound 1 has a characteristic XRPD peak at about 9.1 degrees 2-theta. In some embodiments, the hydrochloric acid salt of Compound 1 has a characteristic XRPD peak at about 13.5 degrees 2-theta. In some embodiments, the hydrochloric acid salt of Compound 1 has a characteristic XRPD peak at about 15.5 degrees 2-theta.

In some embodiments, the hydrochloric acid salt of Compound 1 has at least one characteristic XRPD peak selected from about 6.7, about 9.1, about 11.0, about 12.7, about 13.5, about 15.5, about 17.1, and about 23.4 degrees 2-theta. In some embodiments, the hydrochloric acid salt of Compound 1 has at least two characteristic XRPD peaks selected from about 6.7, about 9.1, about 11.0, about 12.7, about 13.5, about 15.5, about 17.1, and about 23.4 degrees 2-theta. In some embodiments, the hydrochloric acid salt of Compound 1 has at least three characteristic XRPD peaks selected from about 6.7, about 9.1, about 11.0, about 12.7, about 13.5, about 15.5, about 17.1, and about 23.4 degrees 2-theta.

In some embodiments, the hydrochloric acid salt of Compound 1 has at least one characteristic XRPD peak selected from about 4.5, about 6.0, about 6.7, about 9.1, about 10.6, about 11.0, about 12.7, about 13.5, about 15.5, about 17.1, about 18.2, about 21.2, about 22.7, and about 23.4 degrees 2-theta. In some embodiments, the hydrochloric acid salt of Compound 1 has at least two characteristic XRPD peaks selected from about 4.5, about 6.0, about 6.7, about 9.1, about 10.6, about 11.0, about 12.7, about 13.5, about 15.5, about 17.1, about 18.2, about 21.2, about 22.7, and about 23.4 degrees 2-theta. In some embodiments, the hydrochloric acid salt of Compound 1 has at least three characteristic XRPD peaks selected from about 4.5, about 6.0, about 6.7, about 9.1, about 10.6, about 11.0, about 12.7, about 13.5, about 15.5, about 17.1, about 18.2, about 21.2, about 22.7, and about 23.4 degrees 2-theta.

Figure 7:
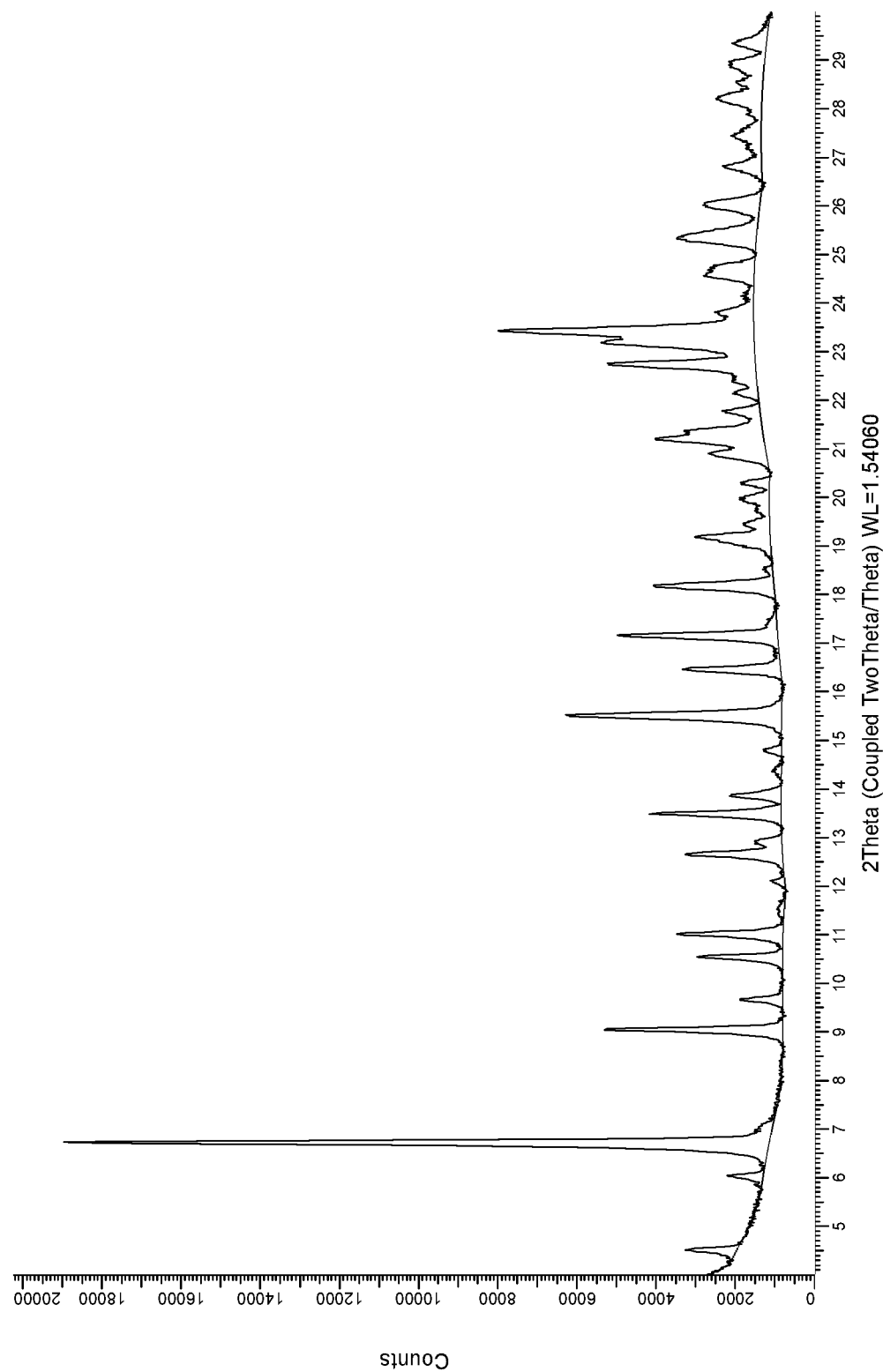
FIG. 7 shows an XRPD pattern of Compound 1 hydrochloride.

In some embodiments, the hydrochloric acid salt of Compound 1 has an XRPD pattern with characteristic peaks as substantially shown in FIG. 7.

Figure 8:
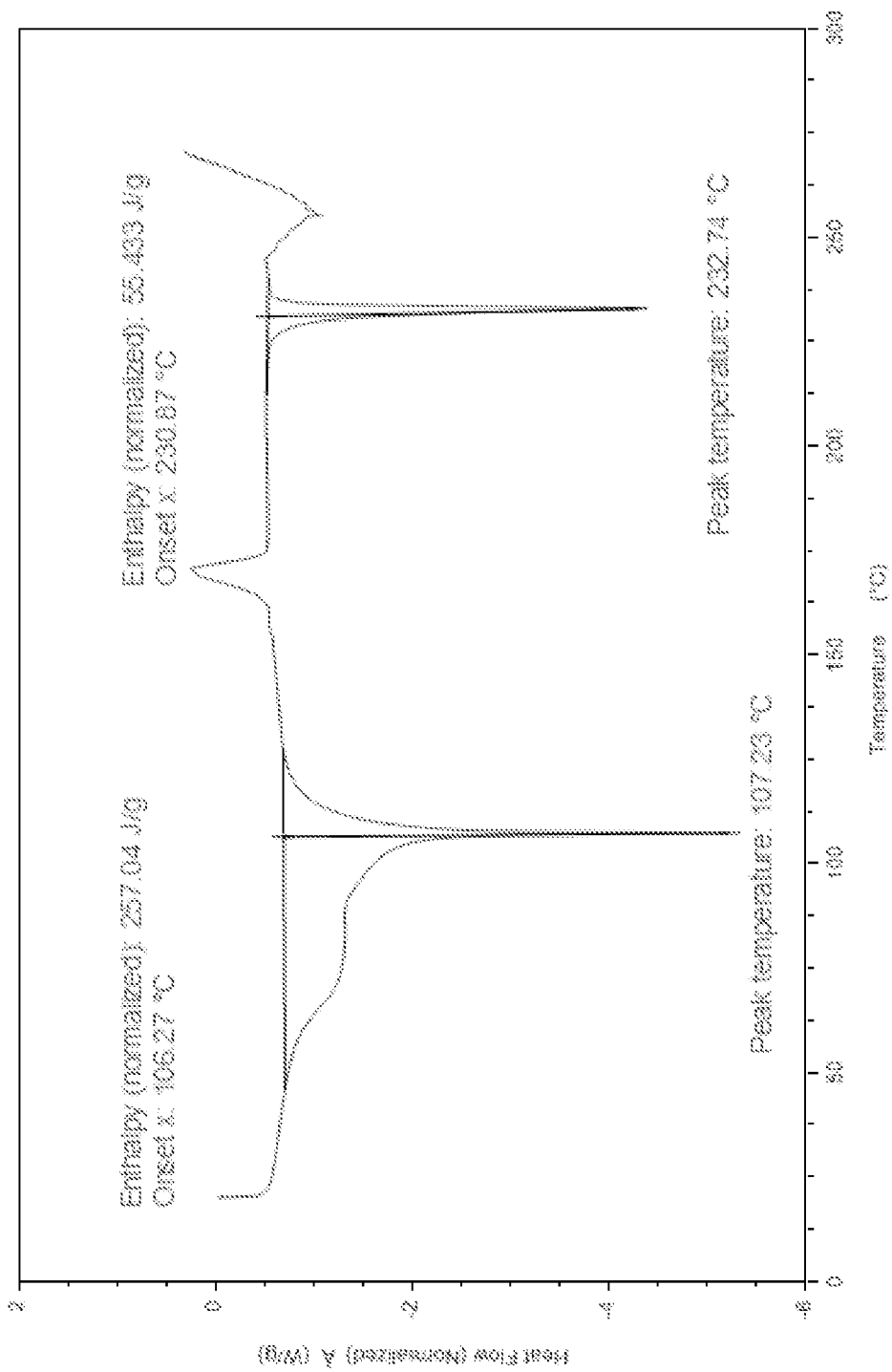
FIG. 8 shows a DSC thermogram of Compound 1 hydrochloride.
Figure 9:
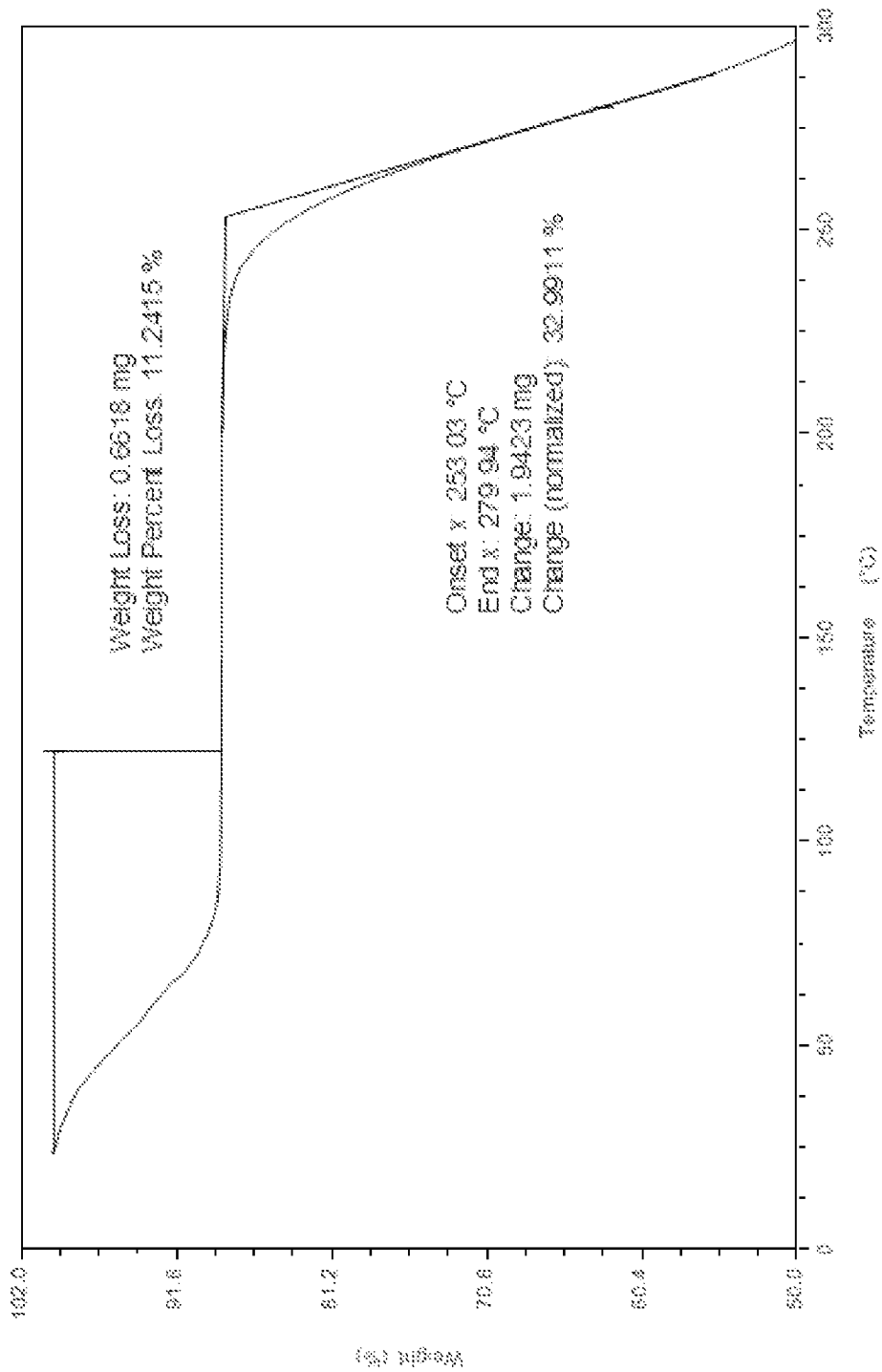
FIG. 9 shows a TGA thermogram of Compound 1 hydrochloride.

In some embodiments, the hydrochloric acid salt of Compound 1 exhibits a DSC thermogram having endothermic peaks at temperatures of about 107° C. and about 233° C. In some embodiments, the hydrochloric acid salt of Compound 1 exhibits a DSC thermogram having an endothermic peak at a temperature of about 107° C. In some embodiments, the hydrochloric acid salt of Compound 1 exhibits a DSC thermogram having an endothermic peak at a temperature of about 233° C. In some embodiments, the hydrochloric acid salt of Compound 1 has a DSC thermogram substantially as depicted in FIG. 8. In some embodiments, the hydrochloric acid salt h of Compound 1 as a TGA thermogram substantially as depicted in FIG. 9.

In some embodiments, the hydrochloric acid salt of Compound 1 has at least one characteristic XRPD peak selected from about 6.7, about 9.1, about 13.5, and about 15.5 degrees 2-theta; and the hydrochloric acid salt exhibits a DSC thermogram having endothermic peaks at temperatures of about 107° C. and about 233° C. In some embodiments, the hydrochloric acid salt of Compound 1 has at least one characteristic XRPD peak selected from about 6.7, about 9.1, about 13.5, and about 15.5 degrees 2-theta; and the hydrochloric acid salt exhibits a DSC thermogram having an endothermic peak at a temperature of about 107° C. In some embodiments, the hydrochloric acid salt of Compound 1 has at least one characteristic XRPD peak selected from about 6.7, about 9.1, about 13.5, and about 15.5 degrees 2-theta; and the hydrochloric acid salt exhibits a DSC thermogram having an endothermic peak at a temperature of about 233° C.

In some embodiments, the hydrochloric acid salt of Compound 1 is substantially crystalline. In some embodiments, the salt is crystalline.

L-(+)-Tartaric Acid Salts

The L-(+)-tartaric acid salt of Compound 1 can be prepared by any suitable method for preparation of L-(+)-tartaric acid addition salts. For example, Compound 1 can be combined with L-(+)-tartaric acid (e.g., about 1.0 molar eq or more) in a solvent and the resulting salt can be isolated by filtering the salt from solution. In certain embodiments, Compound 1 is combined with about 1 to about 2 molar equivalents of L-(+)-tartaric acid. In certain embodiments, Compound 1 is combined with about 1 to about 1.5 molar equivalents of L-(+)-tartaric acid. In certain embodiments, Compound 1 is combined with about 1.15 molar equivalents of L-(+)-tartaric acid. In some embodiments, the solvent is a polar solvent. In some embodiments, the solvent is a $C_{1-6}$ alkyl alcohol. In some embodiments, the solvent is methanol.

The L-(+)-tartaric acid salt of Compound 1 can be crystallized to provide a crystalline solid form. In some embodiments, the crystallization of the L-(+)-tartaric acid salt of Compound 1 comprises precipitating the L-(+)-tartaric acid salt of Compound 1 from a crystallizing solvent. In some embodiments, the crystallizing solvent is a polar solvent. In some embodiments, the crystallizing solvent is water.

In some embodiments, the L-(+)-tartaric acid salt of Compound 1 has at least one characteristic XRPD peak selected from about 4.9, about 7.9, and about 9.8 degrees 2-theta. In some embodiments, the L-(+)-tartaric acid salt of Compound 1 has at least two characteristic XRPD peaks selected from about 4.9, about 7.9, and about 9.8 degrees 2-theta. In some embodiments, the L-(+)-tartaric acid salt of Compound 1 has three characteristic XRPD peaks selected from about 4.9, about 7.9, and about 9.8 degrees 2-theta. In some embodiments, the L-(+)-tartaric acid salt of Compound 1 has a characteristic XRPD peak at about 4.9 degrees 2-theta. In some embodiments, the L-(+)-tartaric acid salt of Compound 1 has a characteristic XRPD peak at about 7.9 degrees 2-theta. In some embodiments, the L-(+)-tartaric acid salt of Compound 1 has a characteristic XRPD peak at about 9.8 degrees 2-theta.

In some embodiments, the L-(+)-tartaric acid salt of Compound 1 has at least one characteristic XRPD peak selected from about 4.9, about 7.9, about 9.8, about 15.9, about 16.9, about 19.6, and about 23.0 degrees 2-theta. In some embodiments, the L-(+)-tartaric acid salt of Compound 1 has at least two characteristic XRPD peaks selected from about 4.9, about 7.9, about 9.8, about 15.9, about 16.9, about 19.6, and about 23.0 degrees 2-theta. In some embodiments, the L-(+)-tartaric acid salt of Compound 1 has at least three characteristic XRPD peaks selected from about 4.9, about 7.9, about 9.8, about 15.9, about 16.9, about 19.6, and about 23.0 degrees 2-theta.

In some embodiments, the L-(+)-tartaric acid salt of Compound 1 has at least one characteristic XRPD peak selected from about 4.9, about 7.5, about 7.9, about 9.8, about 10.5, about 13.7, about 14.7, about 15.9, about 16.0, about 16.9, about 18.1, about 19.6, about 20.8, about 23.0, and about 24.7 degrees 2-theta. In some embodiments, the L-(+)-tartaric acid salt of Compound 1 has at least two characteristic XRPD peaks selected from about 4.9, about 7.5, about 7.9, about 9.8, about 10.5, about 13.7, about 14.7, about 15.9, about 16.0, about 16.9, about 18.1, about 19.6, about 20.8, about 23.0, and about 24.7 degrees 2-theta. In some embodiments, the L-(+)-tartaric acid salt of Compound 1 has at least three characteristic XRPD peaks selected from about 4.9, about 7.5, about 7.9, about 9.8, about 10.5, about 13.7, about 14.7, about 15.9, about 16.0, about 16.9, about 18.1, about 19.6, about 20.8, about 23.0, and about 24.7 degrees 2-theta.

Figure 10:
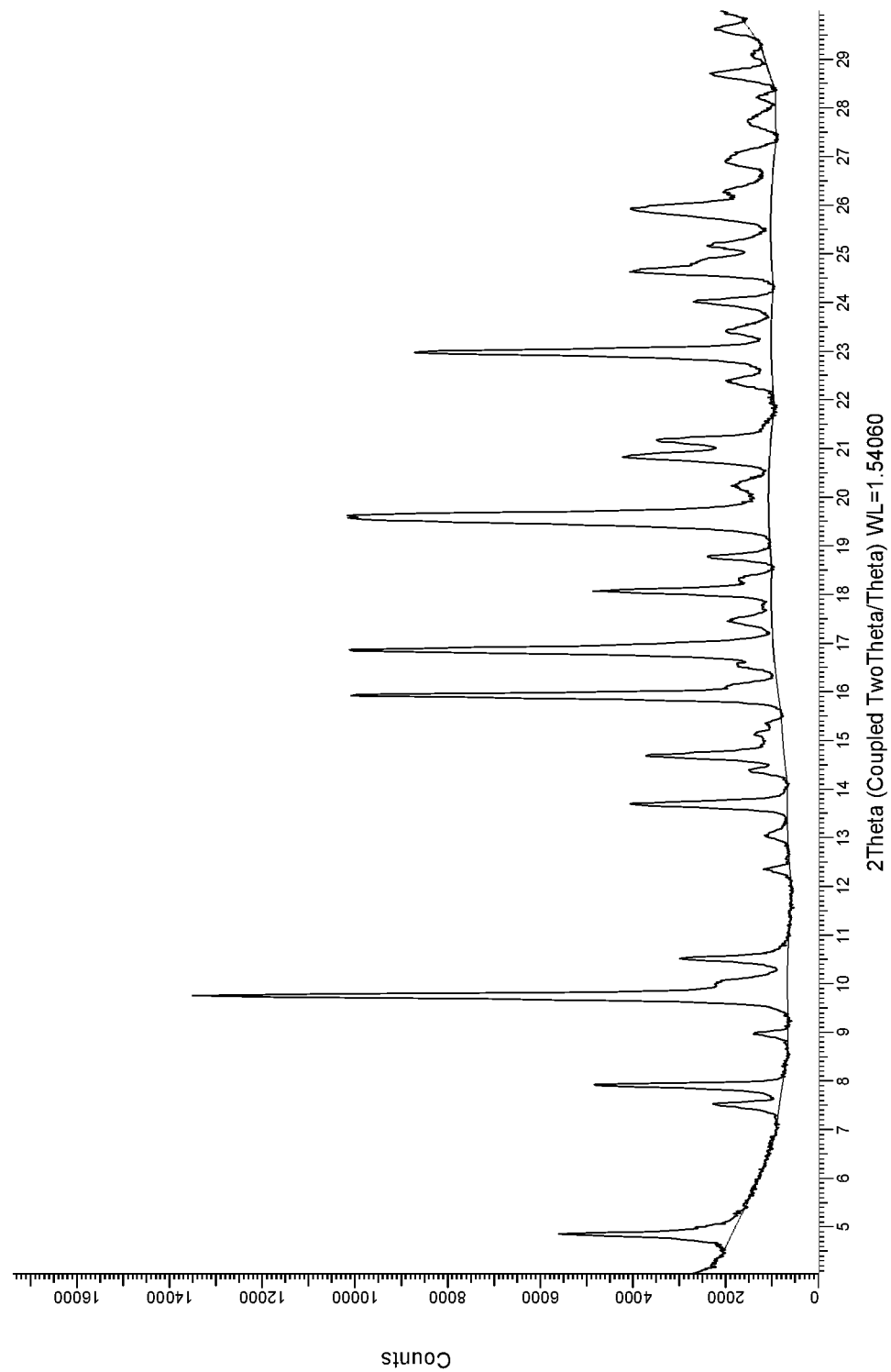
FIG. 10 shows an XRPD pattern of Compound 1 L-tartrate.

In some embodiments, the L-(+)-tartaric acid salt of Compound 1 has an XRPD pattern with characteristic peaks as substantially shown in FIG. 10.

Figure 11:
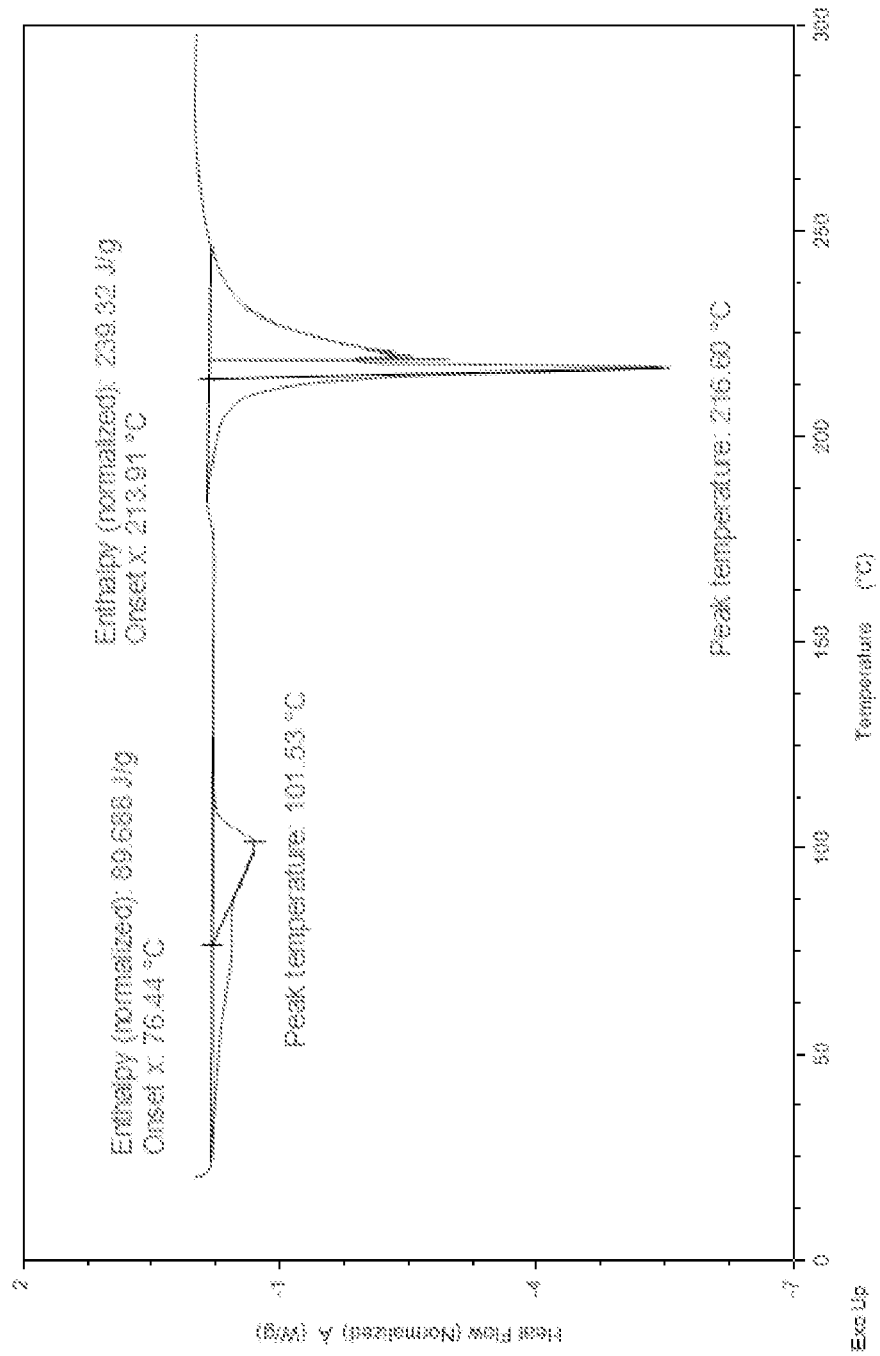
FIG. 11 shows a DSC thermogram of Compound 1 L-tartrate.
Figure 12:
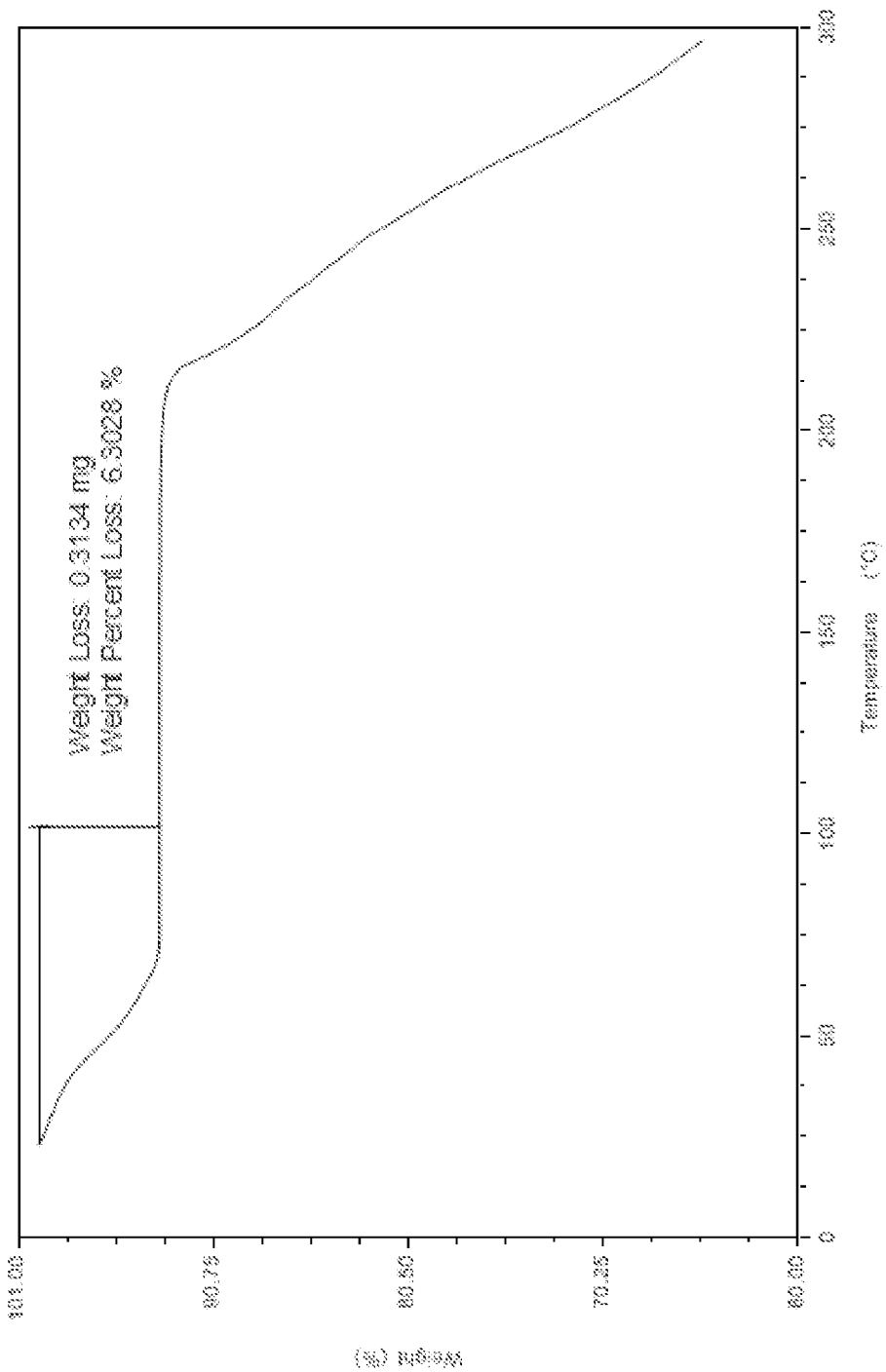
FIG. 12 shows a TGA thermogram of Compound 1 L-tartrate.

In some embodiments, the L-(+)-tartaric acid salt of Compound 1 exhibits a DSC thermogram having endothermic peaks at temperatures of about 102° C. and about 217° C. In some embodiments, the endothermic peak is at a temperature of about 102° C. In some embodiments, the endothermic peak is at a temperature of about 217° C. In some embodiments, the L-(+)-tartaric acid salt of Compound 1 has a DSC thermogram substantially as depicted in FIG. 11. In some embodiments, the L-(+)-tartaric acid salt of Compound 1 has a TGA thermogram substantially as depicted in FIG. 12.

In some embodiments, the L-(+)-tartaric acid salt of Compound 1 has at least one characteristic XRPD peak selected from about 4.9, about 7.9, and about 9.8 degrees 2-theta; and the L-(+)-tartaric acid salt exhibits a DSC thermogram having endothermic peaks at temperatures of about 102° C. and about 217° C. In some embodiments, the L-(+)-tartaric acid salt of Compound 1 has at least one characteristic XRPD peak selected from about 4.9, about 7.9, and about 9.8 degrees 2-theta; and the L-(+)-tartaric acid salt exhibits a DSC thermogram having an endothermic peak at a temperature of about 102° C. In some embodiments, the L-(+)-tartaric acid salt of Compound 1 has at least one characteristic XRPD peak selected from about 4.9, about 7.9, and about 9.8 degrees 2-theta; and the L-(+)-tartaric acid salt exhibits a DSC thermogram having an endothermic peak at a temperature of about 217° C.

In some embodiments, the L-(+)-tartaric acid salt of Compound 1 is substantially crystalline. In some embodiments, the salt is crystalline.

Malic Acid Salts

The malic acid salt of Compound 1 can be prepared by any suitable method for preparation of malic acid addition salts. For example, Compound 1 can be combined with L-(−)-malic acid (e.g., about 1.0 molar eq or more) in a solvent and the resulting salt can be isolated by filtering the salt from solution. In certain embodiments, Compound 1 is combined with about 1 to about 2 molar equivalents of L-(−)-malic acid. In certain embodiments, Compound 1 is combined with about 1 to about 1.5 molar equivalents of L-(−)-malic acid. In certain embodiments, Compound 1 is combined with about 1.2 molar equivalents of L-(−)-malic acid. In some embodiments, the solvent is a polar solvent. In some embodiments, the solvent is a $C_{1-6}$ alkyl alcohol. In some embodiments, the solvent is methanol.

The malic acid salt of Compound 1 can be crystallized to provide a crystalline solid form. In some embodiments, the crystallization of the malic acid salt of Compound 1 comprises precipitating the malic acid salt of Compound 1 from a crystallizing solvent. In some embodiments, the crystallizing solvent is a polar solvent. In some embodiments, the solvent is a $C_{1-6}$ alkyl alcohol. In some embodiments, the solvent is methanol.

In some embodiments, the malic acid salt of Compound 1 has at least one characteristic XRPD peak selected from about 5.2, about 10.4, and about 21.0 degrees 2-theta. In some embodiments, the malic acid salt of Compound 1 has at least two characteristic XRPD peaks selected from about 5.2, about 10.4, and about 21.0 degrees 2-theta. In some embodiments, the malic acid salt of Compound 1 has three characteristic XRPD peaks selected from about 5.2, about 10.4, and about 21.0 degrees 2-theta. In some embodiments, the malic acid salt of Compound 1 has a characteristic XRPD peak at about 5.2 degrees 2-theta. In some embodiments, the malic acid salt of Compound 1 has a characteristic XRPD peak at about 10.4 degrees 2-theta. In some embodiments, the malic acid salt of Compound 1 has a characteristic XRPD peak at about 21.0 degrees 2-theta.

In some embodiments, the malic acid salt of Compound 1 has at least one characteristic XRPD peak selected from about 5.2, about 7.9, about 10.4, about 14.3, about 15.8, about 16.6, about 18.0, about 21.0, and about 21.2 degrees 2-theta. In some embodiments, the malic acid salt of Compound 1 has at least two characteristic XRPD peaks selected from about 5.2, about 7.9, about 10.4, about 14.3, about 15.8, about 16.6, about 18.0, about 21.0, and about 21.2 degrees 2-theta. In some embodiments, the malic acid salt of Compound 1 has at least three characteristic XRPD peaks selected from about 5.2, about 7.9, about 10.4, about 14.3, about 15.8, about 16.6, about 18.0, about 21.0, and about 21.2 degrees 2-theta.

In some embodiments, the malic acid salt of Compound 1 has at least one characteristic XRPD peak selected from about 5.2, about 7.9, about 8.2, about 10.4, about 14.3, about 15.8, about 16.6, about 18.0, about 19.2, about 21.0, about 21.2, about 25.9 degrees 2-theta. In some embodiments, the malic acid salt of Compound 1 has at least two characteristic XRPD peaks selected from about 5.2, about 7.9, about 8.2, about 10.4, about 14.3, about 15.8, about 16.6, about 18.0, about 19.2, about 21.0, about 21.2, about 25.9 degrees 2-theta. In some embodiments, the malic acid salt of Compound 1 has at least three characteristic XRPD peaks selected from about 5.2, about 7.9, about 8.2, about 10.4, about 14.3, about 15.8, about 16.6, about 18.0, about 19.2, about 21.0, about 21.2, about 25.9 degrees 2-theta.

Figure 13:
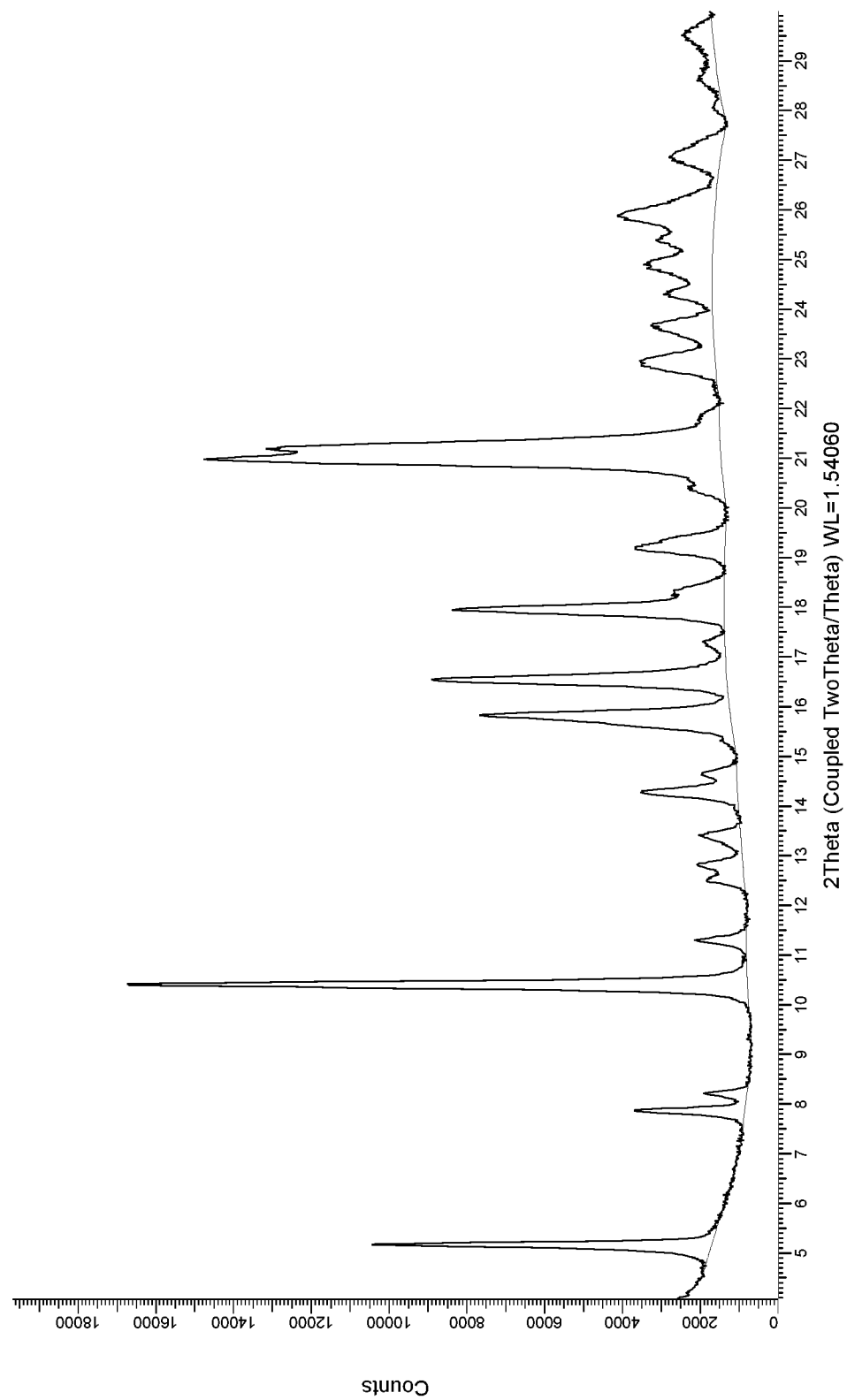
FIG. 13 shows an XRPD pattern of Compound 1 malate.

In some embodiments, the malic acid salt of Compound 1 has an XRPD pattern with characteristic peaks as substantially shown in FIG. 13.

Figure 14:
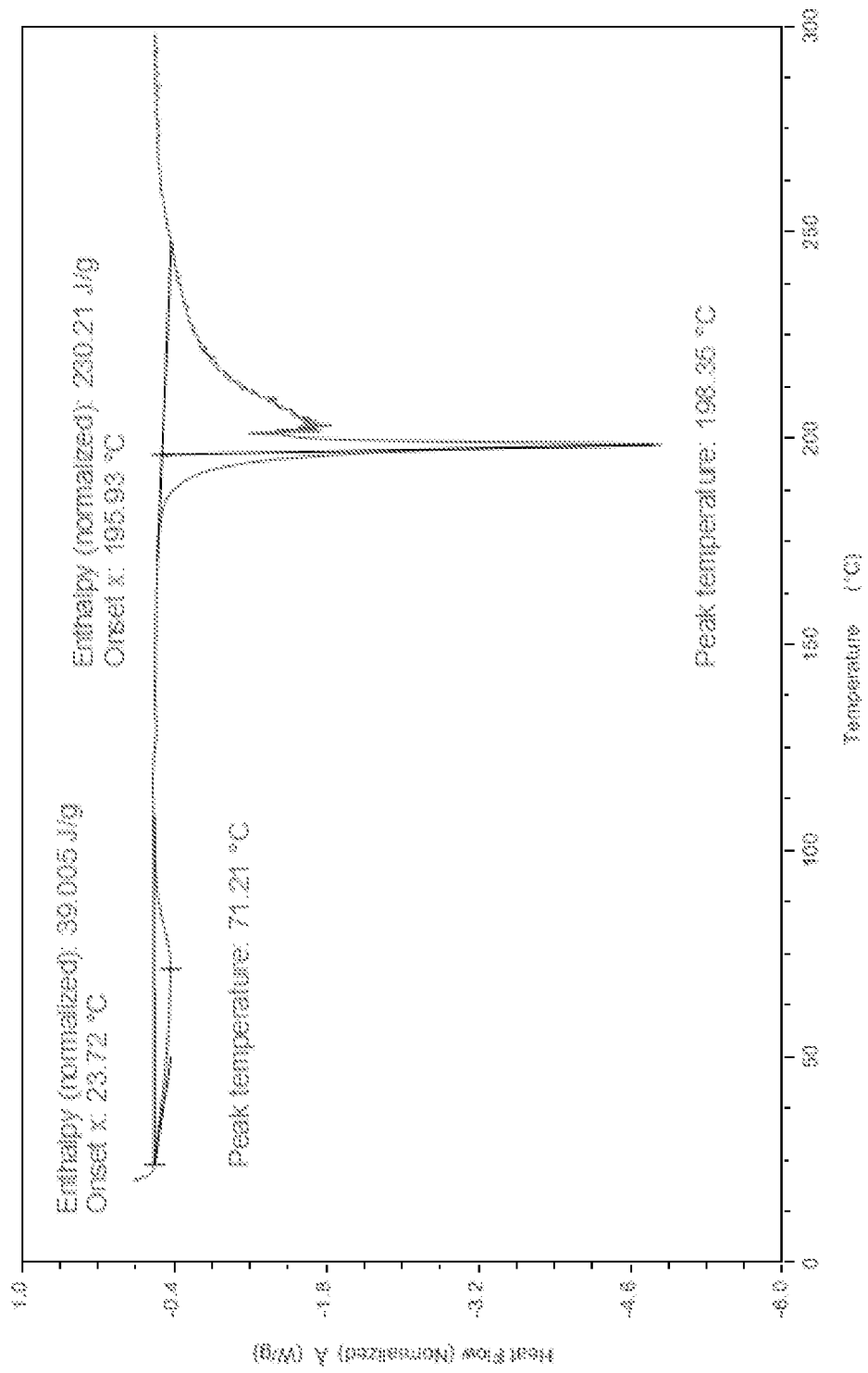
FIG. 14 shows a DSC thermogram of Compound 1 malate.
Figure 15:
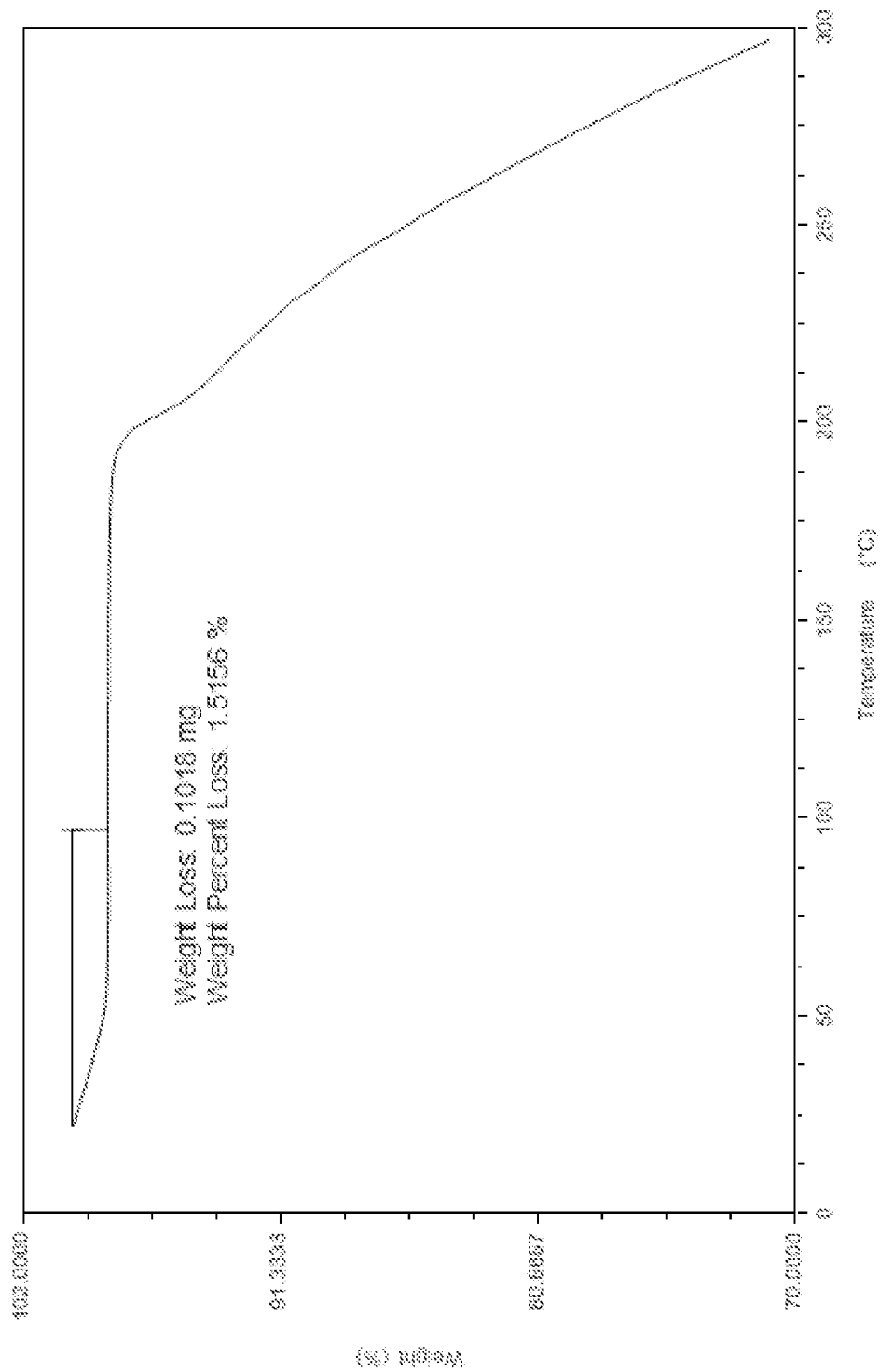
FIG. 15 shows a TGA thermogram of Compound 1 malate.

In some embodiments, the malic acid salt of Compound 1 exhibits a DSC thermogram having endothermic peaks at temperatures of about 71° C. and about 198° C. In some embodiments, the malic acid salt of Compound 1 exhibits a DSC thermogram having an endothermic peak at a temperature of about 71° C. In some embodiments, the malic acid salt of Compound 1 exhibits a DSC thermogram having an endothermic peak at a temperature of about 198° C. In some embodiments, the malic acid salt of Compound 1 has a DSC thermogram substantially as depicted in FIG. 14. In some embodiments, the malic acid salt of Compound 1 has a TGA thermogram substantially as depicted in FIG. 15.

In some embodiments, the malic acid salt of Compound 1 has at least one characteristic XRPD peak selected from about 5.2, about 10.4, and about 21.0 degrees 2-theta; and the malic acid salt exhibits a DSC thermogram having endothermic peaks at temperatures of about 71° C. and about 198° C. In some embodiments, the malic acid salt of Compound 1 has at least one characteristic XRPD peak selected from about 5.2, about 10.4, and about 21.0 degrees 2-theta; and the malic acid salt exhibits a DSC thermogram having an endothermic peak at a temperature of about 71° C. In some embodiments, the malic acid salt of Compound 1 has at least one characteristic XRPD peak selected from about 5.2, about 10.4, and about 21.0 degrees 2-theta;

and the malic acid salt exhibits a DSC thermogram having an endothermic peak at a temperature of about 198° C.

In some embodiments, the malic acid salt of Compound 1 is substantially crystalline. In some embodiments, the salt is crystalline.

Camphorsulfonic Acid Salts

The camphorsulfonic acid salt of Compound 1 can be prepared by any suitable method for preparation of camphorsulfonic acid addition salts. For example, Compound 1 can be combined with (1S)-(+)-camphorsulfonic acid (e.g., about 1.0 molar eq or more) in a solvent and the resulting salt can be isolated by filtering the salt from solution. In certain embodiments, Compound 1 is combined with about 1 to about 2 molar equivalents of (1S)-(+)-camphorsulfonic acid. In certain embodiments, Compound 1 is combined with about 1 to about 1.5 molar equivalents of (1S)-(+)-camphorsulfonic acid. In certain embodiments, Compound 1 is combined with about 1.1 molar equivalents of (1S)-(+)-camphorsulfonic acid. In some embodiments, the solvent is a polar solvent. In some embodiments, the solvent is a $C_{1-6}$ alkyl alcohol. In some embodiments, the solvent is methanol.

The camphorsulfonic acid salt of Compound 1 can be crystallized to provide a crystalline solid form. In some embodiments, the crystallization of the camphorsulfonic acid salt of Compound 1 comprises precipitating the camphorsulfonic acid salt of Compound 1 from a crystallizing solvent. In some embodiments, the crystallizing solvent is a polar solvent. In some embodiments, the solvent is water.

In some embodiments, the camphorsulfonic acid salt of Compound 1 has at least one characteristic XRPD peak selected from about 4.9, about 5.9, and about 15.1 degrees 2-theta. In some embodiments, the camphorsulfonic acid salt of Compound 1 has at least two characteristic XRPD peaks selected from about 4.9, about 5.9, and about 15.1 degrees 2-theta. In some embodiments, the camphorsulfonic acid salt of Compound 1 has three characteristic XRPD peaks selected from about 4.9, about 5.9, and about 15.1 degrees 2-theta. In some embodiments, the camphorsulfonic acid salt of Compound 1 has a characteristic XRPD peak at about 4.9 degrees 2-theta. In some embodiments, the camphorsulfonic acid salt of Compound 1 has a characteristic XRPD peak at about 5.9 degrees 2-theta. In some embodiments, the camphorsulfonic acid salt of Compound 1 has a characteristic XRPD peak at about 15.1 degrees 2-theta.

In some embodiments, the camphorsulfonic acid salt of Compound 1 has at least one characteristic XRPD peak selected from about 4.9, about 5.9, about 10.9, about 14.4, about 15.0, about 15.1, about 19.8, about 20.1, and about 25.8 degrees 2-theta. In some embodiments, the camphorsulfonic acid salt of Compound 1 has at least two characteristic XRPD peaks selected from about 4.9, about 5.9, about 10.9, about 14.4, about 15.0, about 15.1, about 19.8, about 20.1, and about 25.8 degrees 2-theta. In some embodiments, the camphorsulfonic acid salt of Compound 1 has at least three characteristic XRPD peaks selected from about 4.9, about 5.9, about 10.9, about 14.4, about 15.0, about 15.1, about 19.8, about 20.1, and about 25.8 degrees 2-theta.

In some embodiments, the camphorsulfonic acid salt of Compound 1 has at least one characteristic XRPD peak selected about 4.9, about 5.9, about 9.8, about 10.9, about 12.2, about 14.4, about 15.0, about 15.1, about 16.5, about 19.8, about 20.1, about 20.9, and about 25.8 degrees 2-theta. In some embodiments, the camphorsulfonic acid salt of Compound 1 has at least two characteristic XRPD peaks selected from about 4.9, about 5.9, about 9.8, about 10.9, about 12.2, about 14.4, about 15.0, about 15.1, about 16.5, about 19.8, about 20.1, about 20.9, and about 25.8 degrees 2-theta. In some embodiments, the camphorsulfonic acid salt of Compound 1 has at least three characteristic XRPD peaks selected from about 4.9, about 5.9, about 9.8, about 10.9, about 12.2, about 14.4, about 15.0, about 15.1, about 16.5, about 19.8, about 20.1, about 20.9, and about 25.8 degrees 2-theta.

Figure 16:
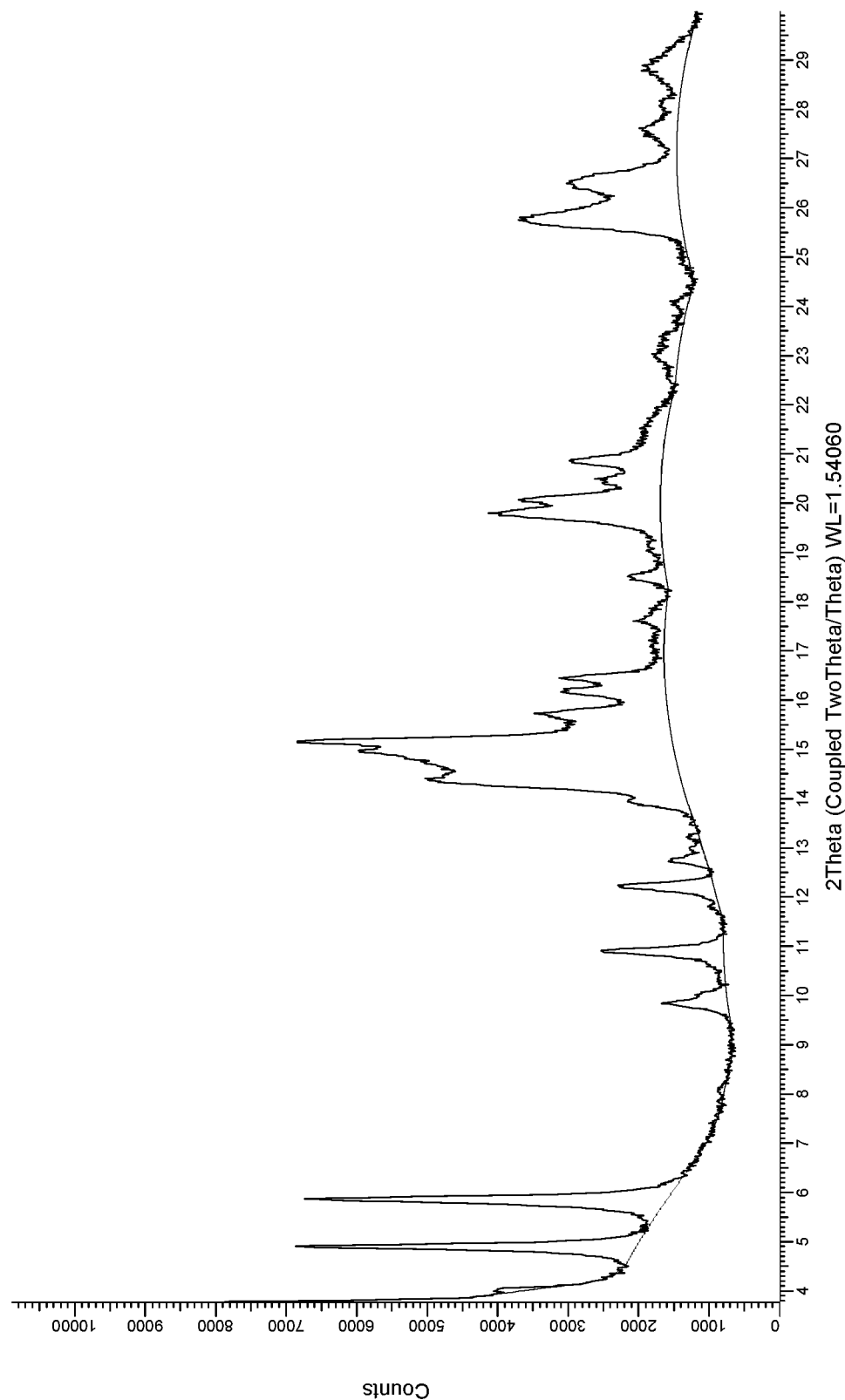
FIG. 16 shows an XRPD pattern of Compound 1 camsylate.

In some embodiments, the camphorsulfonic acid salt of Compound 1 has an XRPD pattern with characteristic peaks as substantially shown in FIG. 16.

Figure 17:
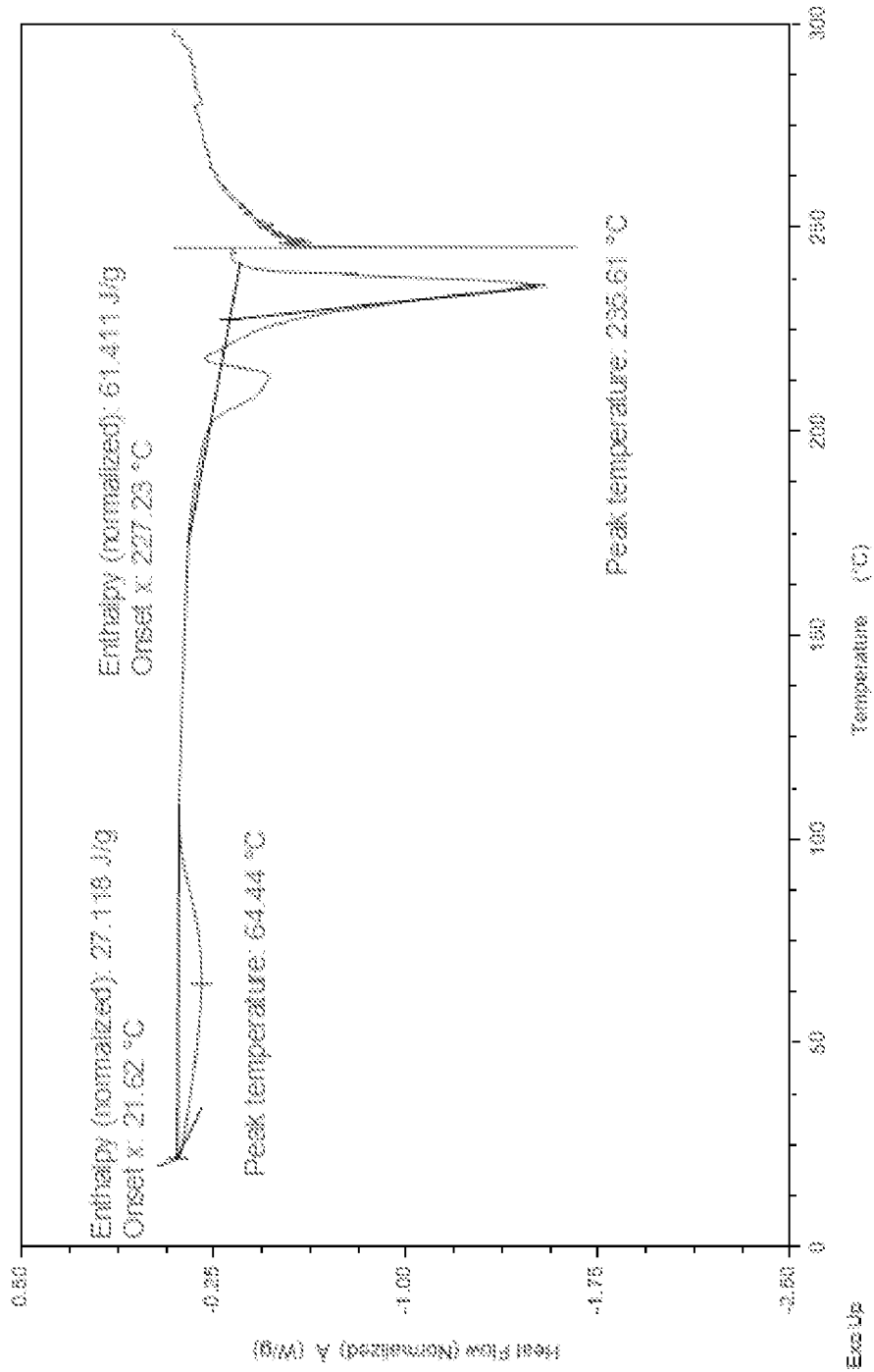
FIG. 17 shows a DSC thermogram of Compound 1 camsylate.
Figure 18:
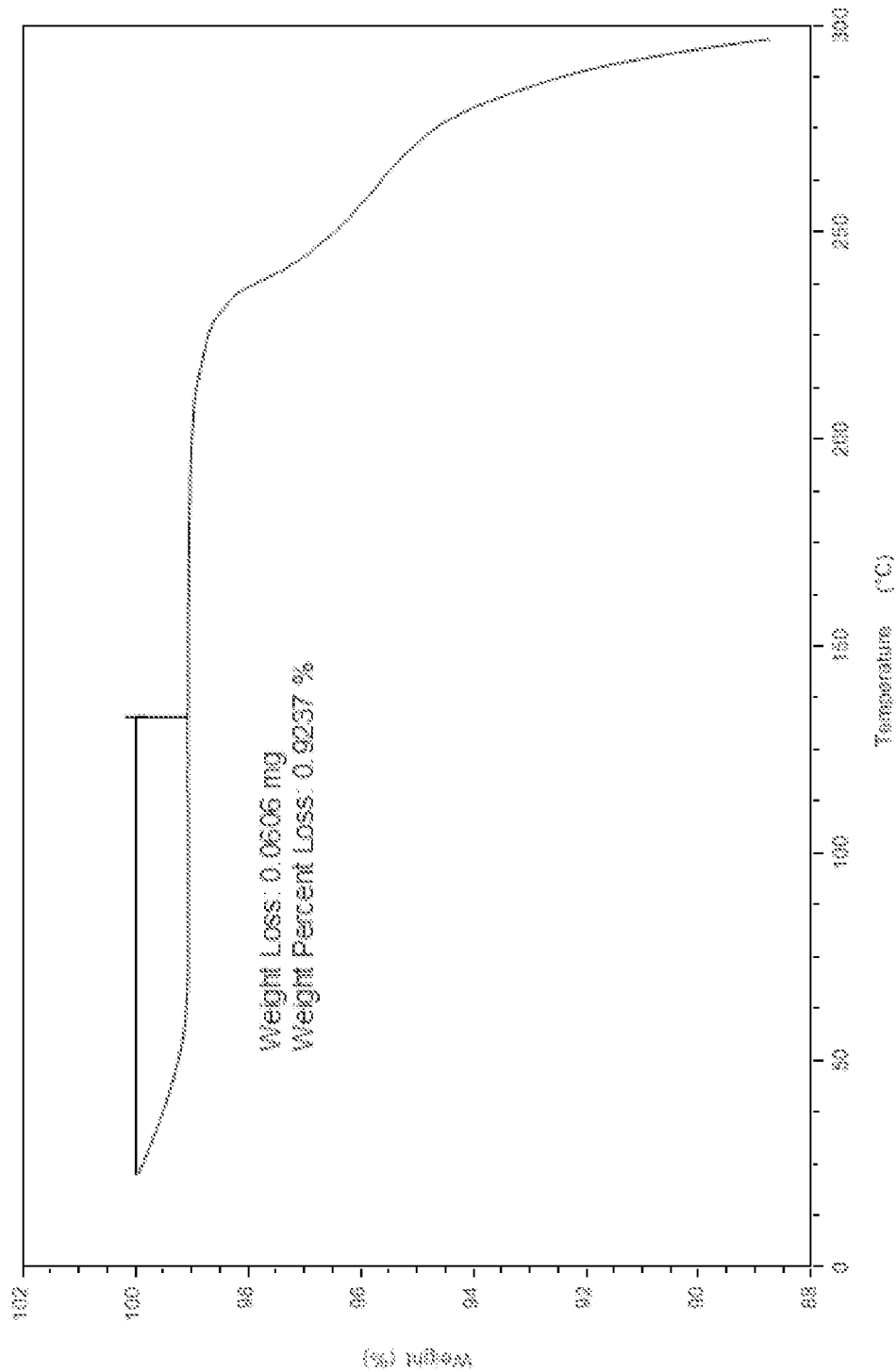
FIG. 18 shows a TGA thermogram of Compound 1 camsylate.

In some embodiments, the camphorsulfonic acid salt of Compound 1 exhibits a DSC thermogram having endothermic peaks at temperatures of about 64° C. and about 236° C. In some embodiments, the camphorsulfonic acid salt of Compound 1 exhibits a DSC thermogram having an endothermic peak at a temperature of about 64° C. In some embodiments, the camphorsulfonic acid salt of Compound 1 exhibits a DSC thermogram having an endothermic peak at a temperature of about 236° C. In some embodiments, the camphorsulfonic acid salt of Compound 1 has a DSC thermogram substantially as depicted in FIG. 17. In some embodiments, the camphorsulfonic acid salt of Compound 1 has a TGA thermogram substantially as depicted in FIG. 18.

In some embodiments, the camphorsulfonic acid salt of Compound 1 has at least one characteristic XRPD peak selected from about 4.9, about 5.9, and about 15.1 degrees 2-theta; and the camphorsulfonic acid salt exhibits a DSC thermogram having endothermic peaks at temperatures of about 64° C. and about 236° C. In some embodiments, the camphorsulfonic acid salt of Compound 1 has at least one characteristic XRPD peak selected from about 4.9, about 5.9, and about 15.1 degrees 2-theta; and the camphorsulfonic acid salt exhibits a DSC thermogram having an endothermic peak at a temperature of about 64° C. In some embodiments, the camphorsulfonic acid salt of Compound 1 has at least one characteristic XRPD peak selected from about 4.9, about 5.9, and about 15.1 degrees 2-theta; and the camphorsulfonic acid salt exhibits a DSC thermogram having an endothermic peak at a temperature of about 236° C.

In some embodiments, the camphorsulfonic acid salt of Compound 1 is substantially crystalline. In some embodiments, the salt is crystalline.

Mandelic Acid Salts

The mandelic acid salt of Compound 1 can be prepared by any suitable method for preparation of mandelic acid addition salts. For example, Compound 1 can be combined with (S)-(+)-mandelic acid (e.g., about 1.0 molar eq or more) in a solvent and the resulting salt can be isolated by filtering the salt from solution. In certain embodiments, Compound 1 is combined with about 1 to about 2 molar equivalents of (S)-(+)-mandelic acid. In certain embodiments, Compound 1 is combined with about 1 to about 1.5 molar equivalents of (S)-(+)-mandelic acid. In certain embodiments, Compound 1 is combined with about 1.2 molar equivalents of (S)-(+)-mandelic acid. In some embodiments, the solvent is a polar solvent. In some embodiments, the solvent is a $C_{1-6}$ alkyl alcohol. In some embodiments, the solvent is methanol.

The mandelic acid salt of Compound 1 can be crystallized to provide a crystalline solid form. In some embodiments, the crystallization of the mandelic acid salt of Compound 1 comprises precipitating the mandelic acid salt of Compound 1 from a crystallizing solvent. In some embodiments, the crystallizing solvent is a polar solvent. In some embodiments, the solvent is water.

In some embodiments, the mandelic acid salt of Compound 1 has at least one characteristic XRPD peak selected from about 4.2, about 5.0, about 5.8, and about 6.9 degrees 2-theta. In some embodiments, the mandelic acid salt of Compound 1 has at least two characteristic XRPD peaks selected from about 4.2, about 5.0, about 5.8, and about 6.9 degrees 2-theta. In some embodiments, the mandelic acid salt of Compound 1 has at least three characteristic XRPD peaks selected from about 4.2, about 5.0, about 5.8, and about 6.9 degrees 2-theta. In some embodiments, the mandelic acid salt of Compound 1 has a characteristic XRPD peak at about 4.2 degrees 2-theta. In some embodiments, the mandelic acid salt of Compound 1 has a characteristic XRPD peak at about 5.0 degrees 2-theta. In some embodiments, the mandelic acid salt of Compound 1 has a characteristic XRPD peak at about 5.8 degrees 2-theta. In some embodiments, the mandelic acid salt of Compound 1 has a characteristic XRPD peak at about 6.9 degrees 2-theta.

In some embodiments, the mandelic acid salt of Compound 1 has at least one characteristic XRPD peak selected from about 4.2, about 5.0, about 5.4, about 5.8, about 6.9, about 14.2, about 15.3, about 19.0, and about 19.6 degrees 2-theta. In some embodiments, the mandelic acid salt of Compound 1 has at least two characteristic XRPD peaks selected from about 4.2, about 5.0, about 5.4, about 5.8, about 6.9, about 14.2, about 15.3, about 19.0, and about 19.6 degrees 2-theta. In some embodiments, the mandelic acid salt of Compound 1 has at least three characteristic XRPD peaks selected from about 4.2, about 5.0, about 5.4, about 5.8, about 6.9, about 14.2, about 15.3, about 19.0, and about 19.6 degrees 2-theta.

In some embodiments, the mandelic acid salt of Compound 1 has at least one characteristic XRPD peak selected about 4.2, about 5.0, about 5.4, about 5.8, about 6.9, about 10.1, about 12.6, about 14.2, about 15.0, about 15.3, about 17.1, about 18.7, about 19.0, and about 19.6 degrees 2-theta. In some embodiments, the mandelic acid salt of Compound 1 has at least two characteristic XRPD peaks selected from about 4.2, about 5.0, about 5.4, about 5.8, about 6.9, about 10.1, about 12.6, about 14.2, about 15.0, about 15.3, about 17.1, about 18.7, about 19.0, and about 19.6 degrees 2-theta. In some embodiments, the mandelic acid salt of Compound 1 has at least three characteristic XRPD peaks selected from about 4.2, about 5.0, about 5.4, about 5.8, about 6.9, about 10.1, about 12.6, about 14.2, about 15.0, about 15.3, about 17.1, about 18.7, about 19.0, and about 19.6 degrees 2-theta.

Figure 19:
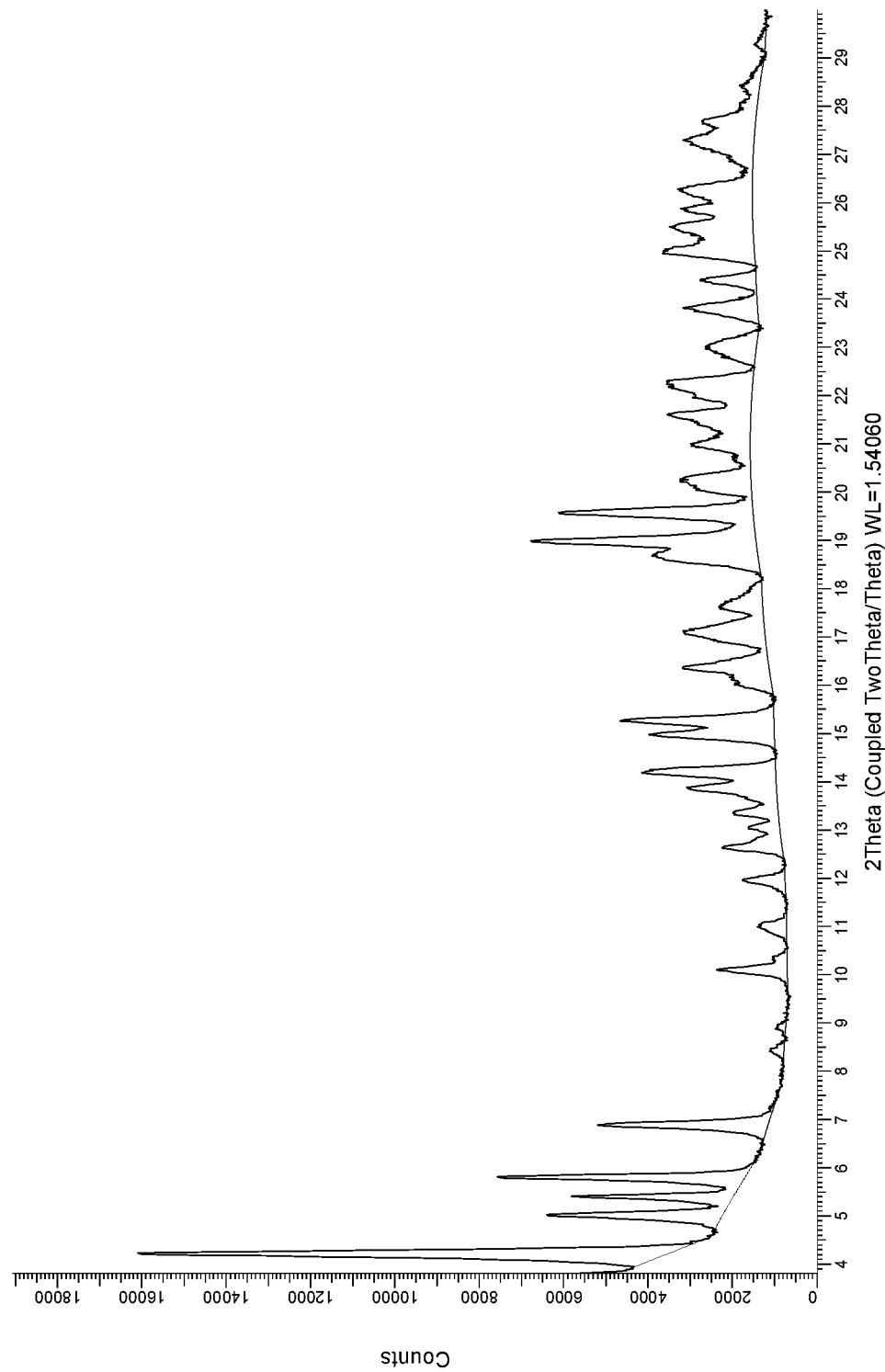
FIG. 19 shows an XRPD pattern of Compound 1 mandelate.

In some embodiments, the mandelic acid salt of Compound 1 has an XRPD pattern with characteristic peaks as substantially shown in FIG. 19.

Figure 20:
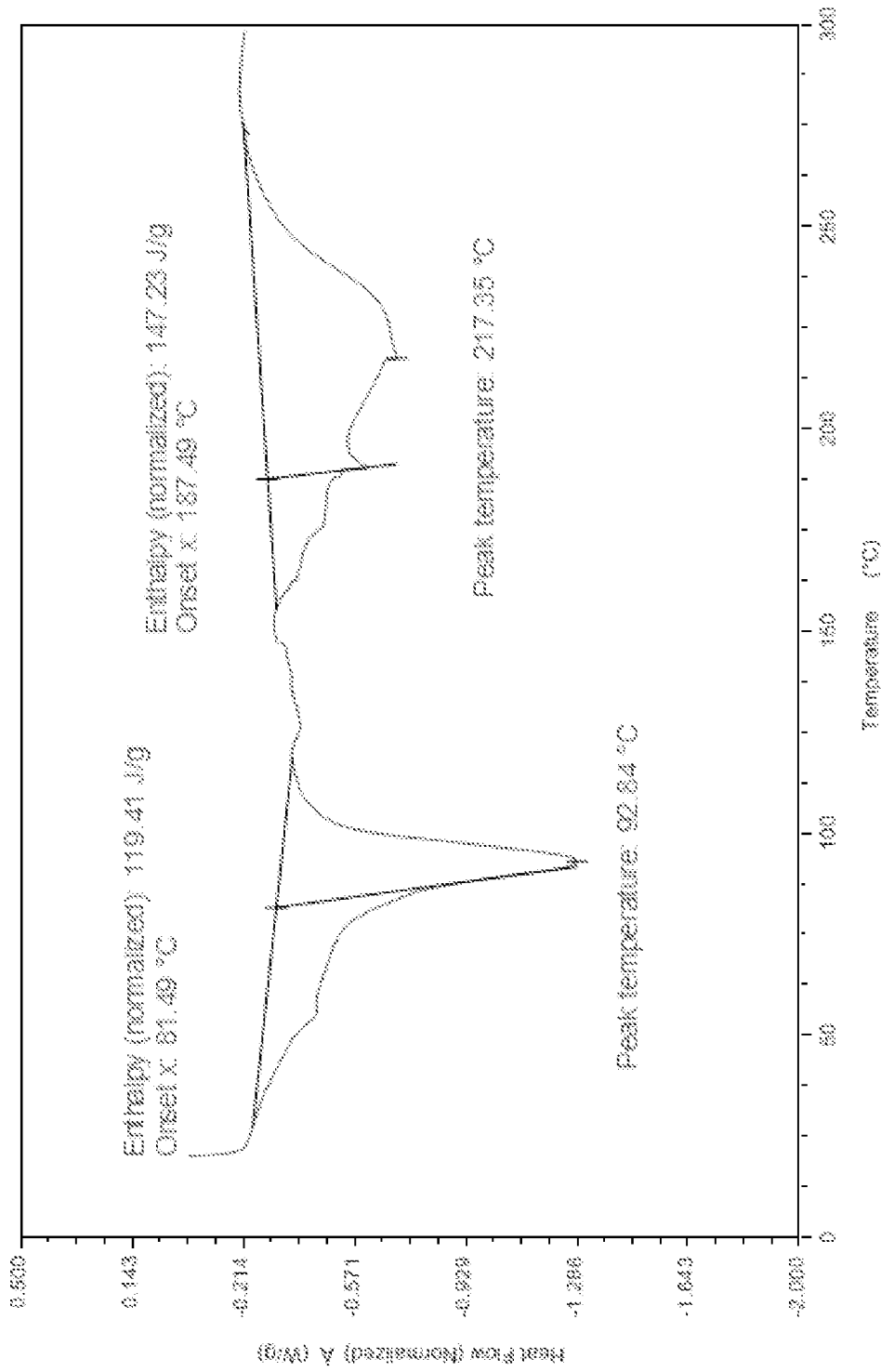
FIG. 20 shows a DSC thermogram of Compound 1 mandelate.
Figure 21:
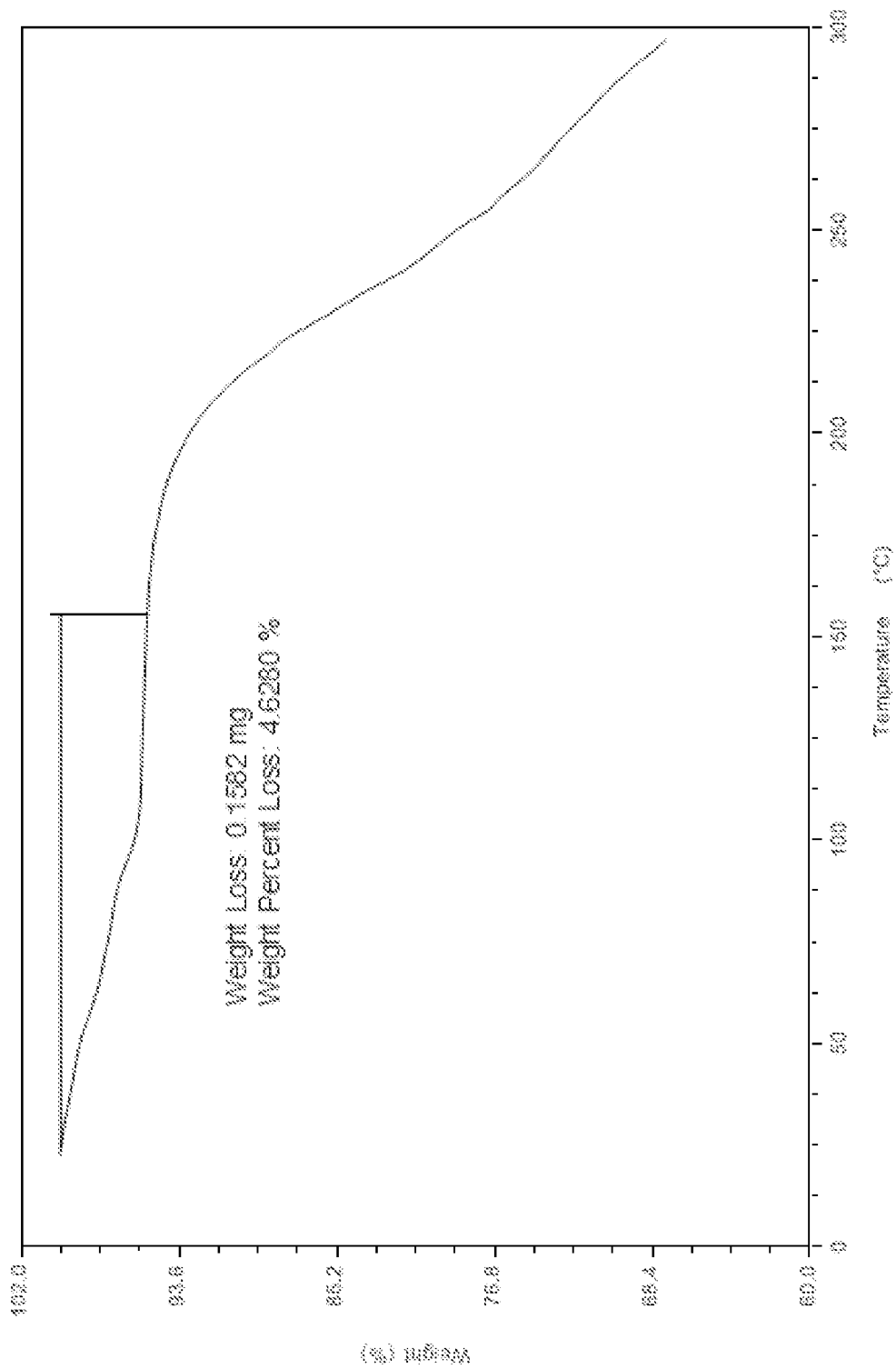
FIG. 21 shows a TGA thermogram of Compound 1 mandelate.

In some embodiments, the mandelic acid salt of Compound 1 exhibits a DSC thermogram having endothermic peaks at temperatures of about 93° C. and about 217° C. In some embodiments, the mandelic acid salt of Compound 1 exhibits a DSC thermogram having an endothermic peak at a temperature of about 93° C. In some embodiments, the mandelic acid salt of Compound 1 exhibits a DSC thermogram having an endothermic peak at a temperature of about 217° C. In some embodiments, the mandelic acid salt of Compound 1 has a DSC thermogram substantially as depicted in FIG. 20. In some embodiments, the mandelic acid salt of Compound 1 has a TGA thermogram substantially as depicted in FIG. 21.

In some embodiments, the mandelic acid salt of Compound 1 has at least one characteristic XRPD peak selected from about 4.2, about 5.0, about 5.8, and about 6.9 degrees 2-theta; and the mandelic acid salt exhibits a DSC thermogram having endothermic peaks at temperatures of about 93° C. and about 217° C. In some embodiments, the mandelic acid salt of Compound 1 has at least one characteristic XRPD peak selected from about 4.2, about 5.0, about 5.8, and about 6.9 degrees 2-theta; and the mandelic acid salt exhibits a DSC thermogram having an endothermic peak at a temperature of about 93° C. In some embodiments, the mandelic acid salt of Compound 1 has at least one characteristic XRPD peak selected from about 4.2, about 5.0, about 5.8, and about 6.9 degrees 2-theta; and the mandelic acid salt exhibits a DSC thermogram having an endothermic peak at a temperature of about 217° C.

In some embodiments, the mandelic acid salt of Compound 1 is substantially crystalline. In some embodiments, the salt is crystalline.

Citric Acid Salts

The citric acid salt of Compound 1 can be prepared by any suitable method for preparation of citric acid addition salts. For example, Compound 1 can be combined with citric acid (e.g., about 1.0 molar eq or more) in a solvent and the resulting salt can be isolated by filtering the salt from solution. In certain embodiments, Compound 1 is combined with about 1 to about 2 molar equivalents of citric acid. In certain embodiments, Compound 1 is combined with about 1 to about 1.5 molar equivalents of citric acid. In certain embodiments, Compound 1 is combined with about 1.05 molar equivalents of citric acid. In some embodiments, the solvent is a polar solvent. In some embodiments, the solvent is a $C_{1-6}$ alkyl alcohol. In some embodiments, the solvent is acetone. In some embodiments, the solvent is a mixture of acetone and water.

The citric acid salt of Compound 1 can be crystallized to provide a crystalline solid form. In some embodiments, the crystallization of the citric acid salt of Compound 1 comprises precipitating the citric acid salt of Compound 1 from a crystallizing solvent. In some embodiments, the crystallizing solvent is acetone. In some embodiments, the crystallizing solvent is a mixture of acetone and water.

In some embodiments, the citric acid salt of Compound 1 has at least one characteristic XRPD peak selected from about 7.3, about 9.0, about 13.6, and about 18.3 degrees 2-theta. In some embodiments, the citric acid salt of Compound 1 has at least two characteristic XRPD peaks selected from about 7.3, about 9.0, about 13.6, and about 18.3 degrees 2-theta. In some embodiments, the citric acid salt of Compound 1 has at least three characteristic XRPD peaks selected from about 7.3, about 9.0, about 13.6, and about 18.3 degrees 2-theta. In some embodiments, the citric acid salt of Compound 1 has a characteristic XRPD peak at about 7.3 degrees 2-theta. In some embodiments, the citric acid salt of Compound 1 has a characteristic XRPD peak at about 9.0 degrees 2-theta. In some embodiments, the citric acid salt of Compound 1 has a characteristic XRPD peak at about 13.6 degrees 2-theta. In some embodiments, the citric acid salt of Compound 1 has a characteristic XRPD peak at about 18.3 degrees 2-theta.

In some embodiments, the citric acid salt of Compound 1 has at least one characteristic XRPD peak selected from about 7.3, about 9.0, about 13.6, about 16.6, about 18.1, about 18.3, about 19.5, about 20.1, and about 20.9 degrees 2-theta. In some embodiments, the citric acid salt of Compound 1 has at least two characteristic XRPD peaks selected from about 7.3, about 9.0, about 13.6, about 16.6, about 18.1, about 18.3, about 19.5, about 20.1, and about 20.9 degrees 2-theta. In some embodiments, the citric acid salt of Compound 1 has at least three characteristic XRPD peaks selected from about 7.3, about 9.0, about 13.6, about 16.6, about 18.1, about 18.3, about 19.5, about 20.1, and about 20.9 degrees 2-theta.

In some embodiments, the citric acid salt of Compound 1 has at least one characteristic XRPD peak selected about 7.3, about 9.0, about 13.6, about 13.9, about 14.9, about 16.6, about 18.1, about 18.3, about 18.8, about 19.5, about 20.1, about 20.9, about 21.6, about 22.4, and about 24.5 degrees 2-theta. In some embodiments, the citric acid salt of Compound 1 has at least two characteristic XRPD peaks selected from about 7.3, about 9.0, about 13.6, about 13.9, about 14.9, about 16.6, about 18.1, about 18.3, about 18.8, about 19.5, about 20.1, about 20.9, about 21.6, about 22.4, and about 24.5 degrees 2-theta. In some embodiments, the citric acid salt of Compound 1 has at least three characteristic XRPD peaks selected from about 7.3, about 9.0, about 13.6, about 13.9, about 14.9, about 16.6, about 18.1, about 18.3, about 18.8, about 19.5, about 20.1, about 20.9, about 21.6, about 22.4, and about 24.5 degrees 2-theta.

Figure 22:
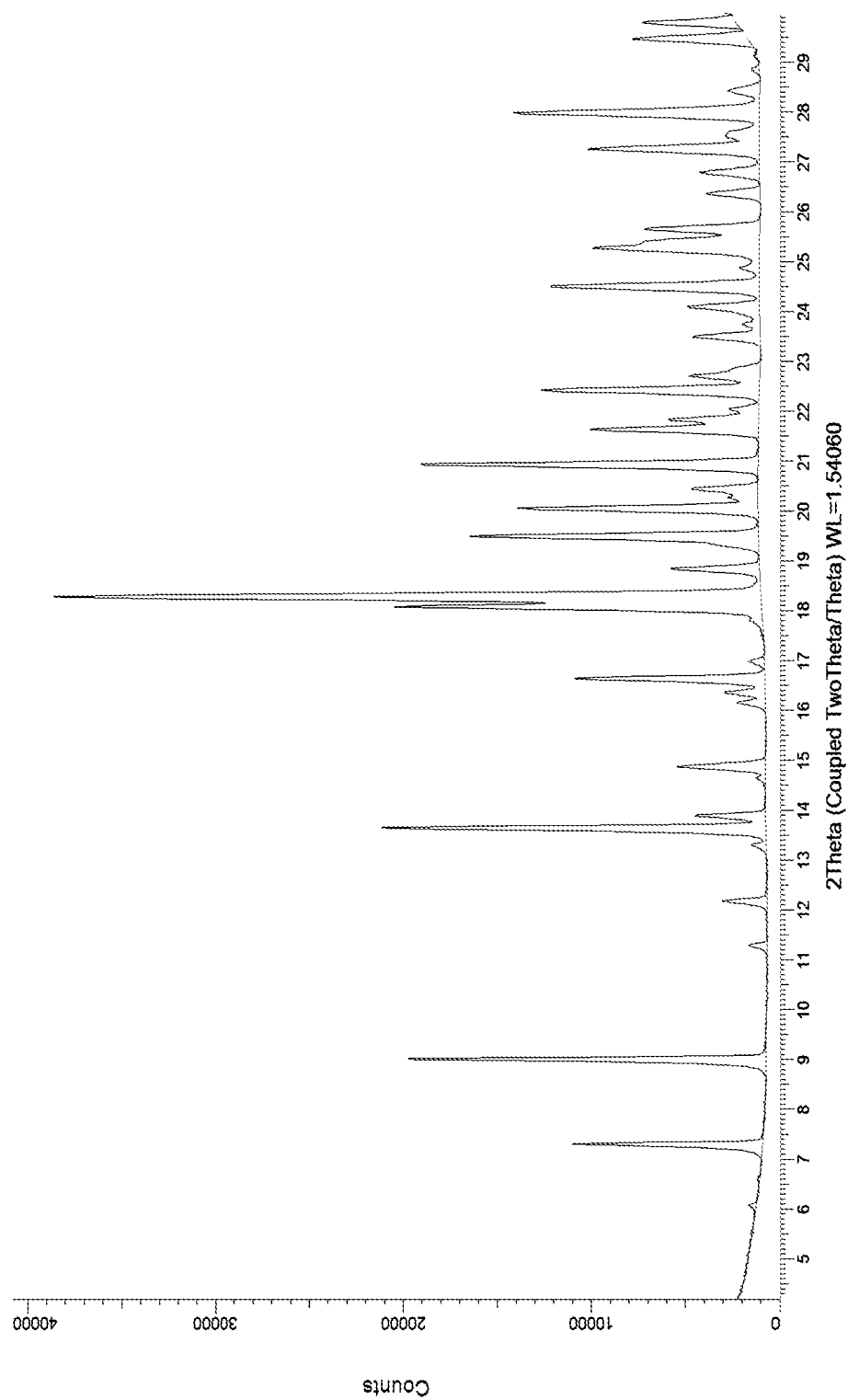
FIG. 22 shows an XRPD pattern of Compound 1 citrate.

In some embodiments, the citric acid salt of Compound 1 has an XRPD pattern with characteristic peaks as substantially shown in FIG. 22.

Figure 23:
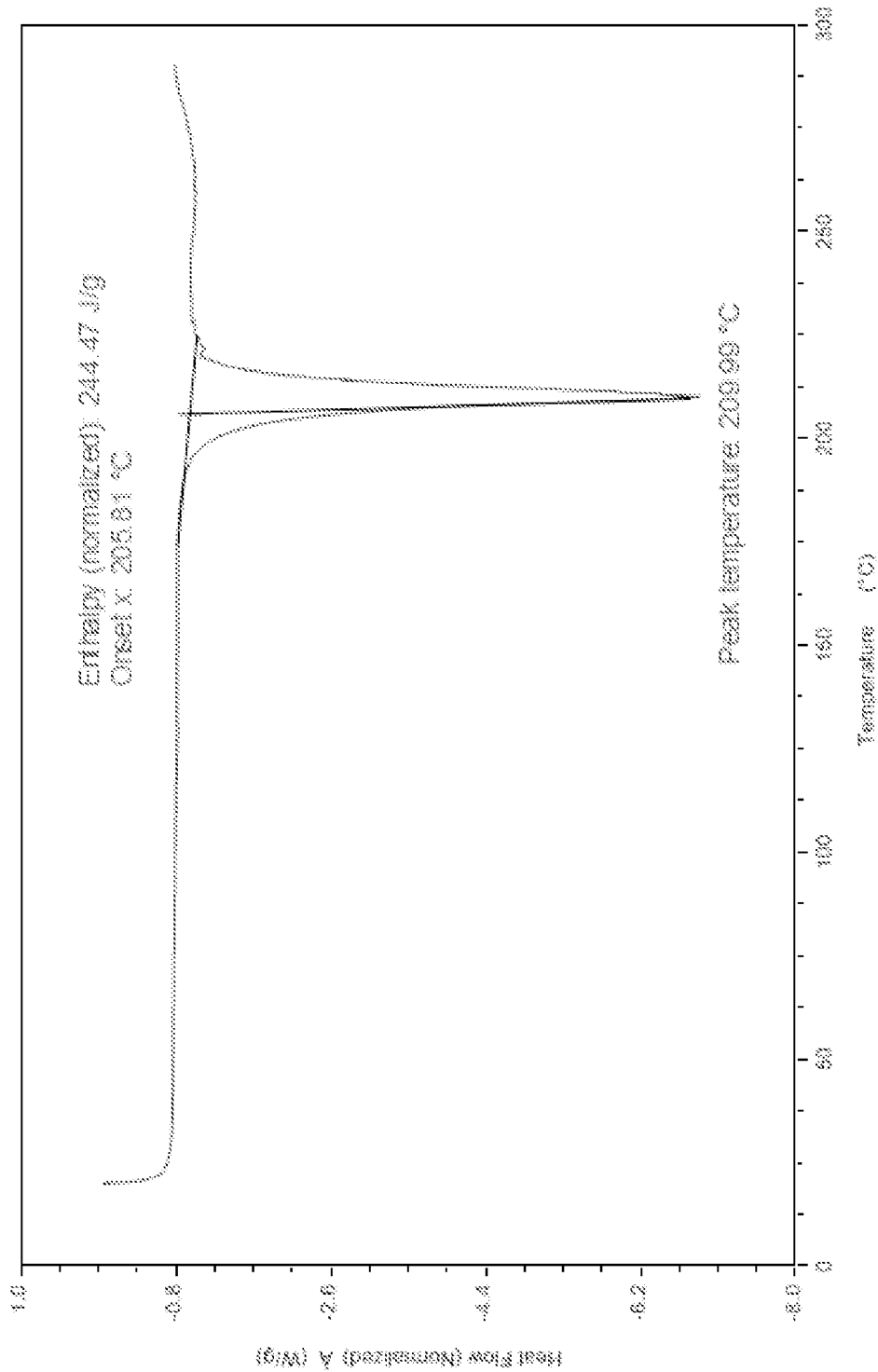
FIG. 23 shows a DSC thermogram of Compound 1 citrate.
Figure 24:
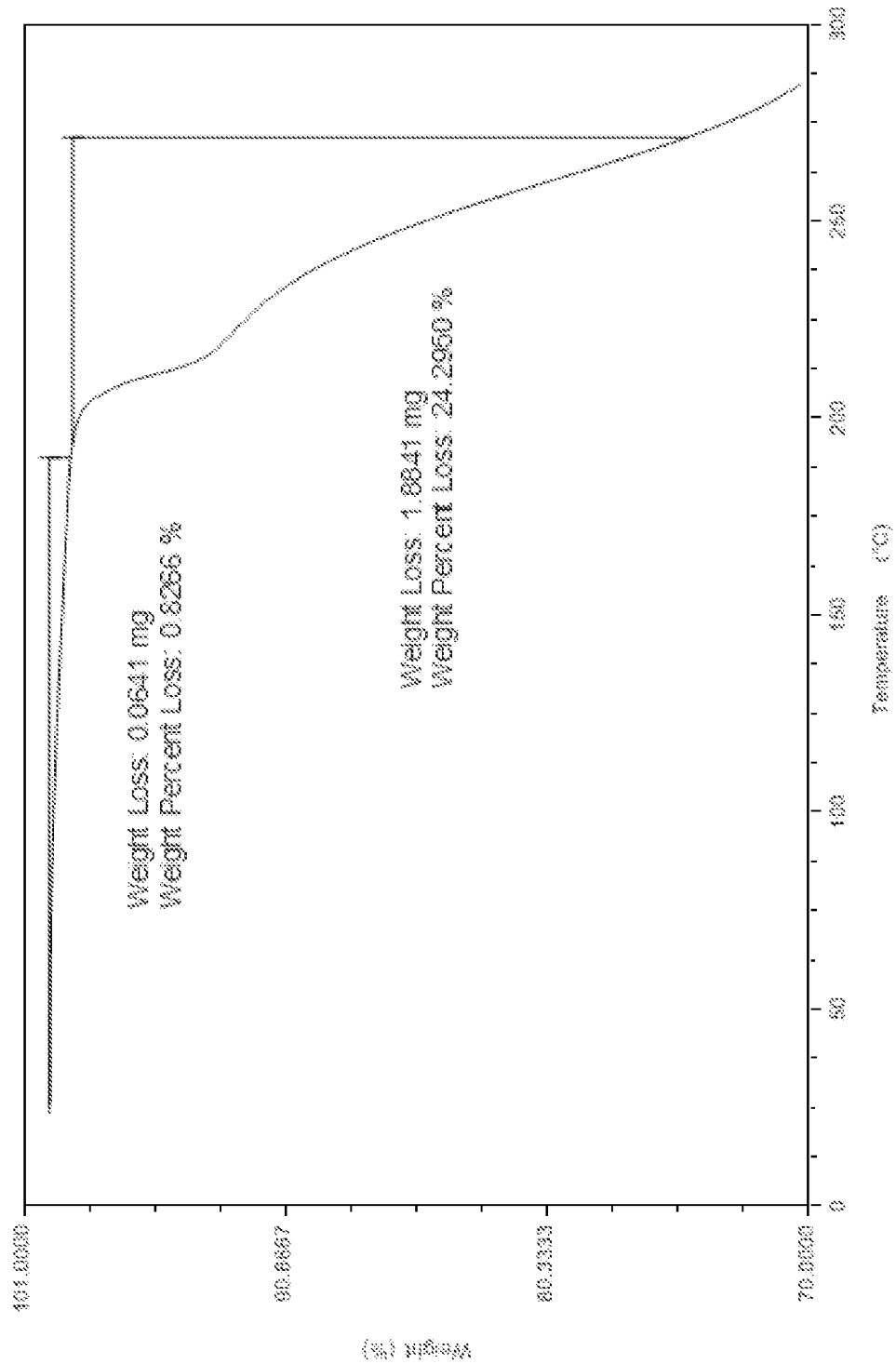
FIG. 24 shows a TGA thermogram of Compound 1 citrate.

In some embodiments, the citric acid salt of Compound 1 exhibits a DSC thermogram having an endothermic peak at temperatures of about 210° C. In some embodiments, the citric acid salt of Compound 1 has a DSC thermogram substantially as depicted in FIG. 23. In some embodiments, the citric acid salt of Compound 1 has a TGA thermogram substantially as depicted in FIG. 24.

In some embodiments, the citric acid salt of Compound 1 has at least one characteristic XRPD peak selected from about 7.3, about 9.0, about 13.6, and about 18.3 degrees 2-theta; and the citric acid salt exhibits a DSC thermogram having an endothermic peak at a temperature of about 210° C.

In some embodiments, the citric acid salt of Compound 1 is substantially crystalline. In some embodiments, the salt is crystalline.

Solid Forms of Compound 2
Phosphoric Acid Salts

The phosphoric acid salt of Compound 2 can be prepared by any suitable method for preparation of phosphoric acid addition salts. For example, Compound 2 can be combined with phosphoric acid (e.g., about 1.0 molar eq or more) in a solvent and the resulting salt can be isolated by filtering the salt from solution. In certain embodiments, Compound 2 is combined with about 1 to about 2 molar equivalents of phosphoric acid. In certain embodiments, Compound 2 is combined with about 1 to about 1.5 molar equivalents of phosphoric acid. In certain embodiments, Compound 2 is combined with about 1.05 molar equivalents of phosphoric acid. In some embodiments, the solvent is a polar solvent. In some embodiments, the solvent is acetone.

The phosphoric acid salt of Compound 2 can be crystallized to provide a crystalline solid form. In some embodiments, the crystallization of the phosphoric acid salt of Compound 2 comprises precipitating the phosphoric acid salt of Compound 2 from a crystallizing solvent. In some embodiments, the crystallizing solvent is acetone.

In some embodiments, the phosphoric acid salt of Compound 2 has at least one characteristic XRPD peak selected from about 6.7, about 10.2, about 14.5, and about 18.0 degrees 2-theta. In some embodiments, the phosphoric acid salt of Compound 2 has at least two characteristic XRPD peaks selected from about 6.7, about 10.2, about 14.5, and about 18.0 degrees 2-theta. In some embodiments, the phosphoric acid salt of Compound 2 has at least three characteristic XRPD peaks selected from about 6.7, about 10.2, about 14.5, and about 18.0 degrees 2-theta. In some embodiments, the phosphoric acid salt of Compound 2 has a characteristic XRPD peak at about 6.7 degrees 2-theta. In some embodiments, the phosphoric acid salt of Compound 2 has a characteristic XRPD peak at about 10.2 degrees 2-theta. In some embodiments, the phosphoric acid salt of Compound 2 has a characteristic XRPD peak at about 14.5 degrees 2-theta. In some embodiments, the phosphoric acid salt of Compound 2 has a characteristic XRPD peak at about 18.0 degrees 2-theta.

In some embodiments, the phosphoric acid salt of Compound 2 has at least one characteristic XRPD peak selected from about 5.9, about 6.7, about 10.2, about 13.4, about 14.5, about 15.5, about 16.5, about 17.4, and about 18.0 degrees 2-theta. In some embodiments, the phosphoric acid salt of Compound 2 has at least two characteristic XRPD peaks selected from about 5.9, about 6.7, about 10.2, about 13.4, about 14.5, about 15.5, about 16.5, about 17.4, and about 18.0 degrees 2-theta. In some embodiments, the phosphoric acid salt of Compound 2 has at least three characteristic XRPD peaks selected from about 5.9, about 6.7, about 10.2, about 13.4, about 14.5, about 15.5, about 16.5, about 17.4, and about 18.0 degrees 2-theta.

In some embodiments, the phosphoric acid salt of Compound 2 has at least one characteristic XRPD peak selected from about 5.9, about 6.3, about 6.7, about 10.2, about 11.0, about 11.9, about 13.4, about 14.5, about 15.5, about 15.9, about 16.5, about 17.4, about 18.0, about 19.2, about 20.4, and about 23.3 degrees 2-theta. In some embodiments, the phosphoric acid salt of Compound 2 has at least two characteristic XRPD peaks selected from about 5.9, about 6.3, about 6.7, about 10.2, about 11.0, about 11.9, about 13.4, about 14.5, about 15.5, about 15.9, about 16.5, about 17.4, about 18.0, about 19.2, about 20.4, and about 23.3 degrees 2-theta. In some embodiments, the phosphoric acid salt of Compound 2 has at least three characteristic XRPD peaks selected from about 5.9, about 6.3, about 6.7, about 10.2, about 11.0, about 11.9, about 13.4, about 14.5, about 15.5, about 15.9, about 16.5, about 17.4, about 18.0, about 19.2, about 20.4, and about 23.3 degrees 2-theta.

Figure 25:
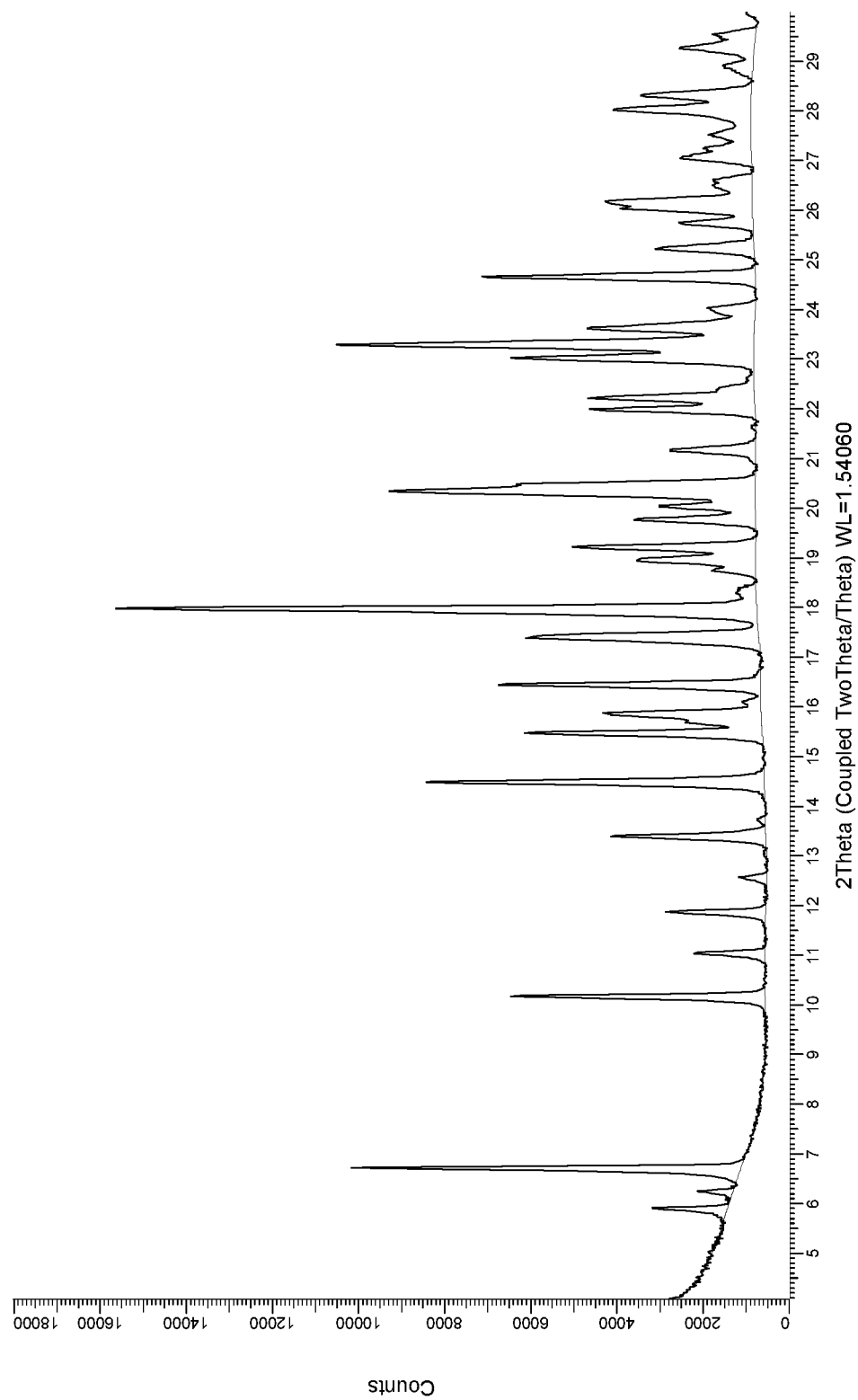
FIG. 25 shows an XRPD pattern of Compound 2 phosphate.

In some embodiments, phosphoric acid salt of Compound 2 has an XRPD pattern with characteristic peaks as substantially shown in FIG. 25.

Figure 26:
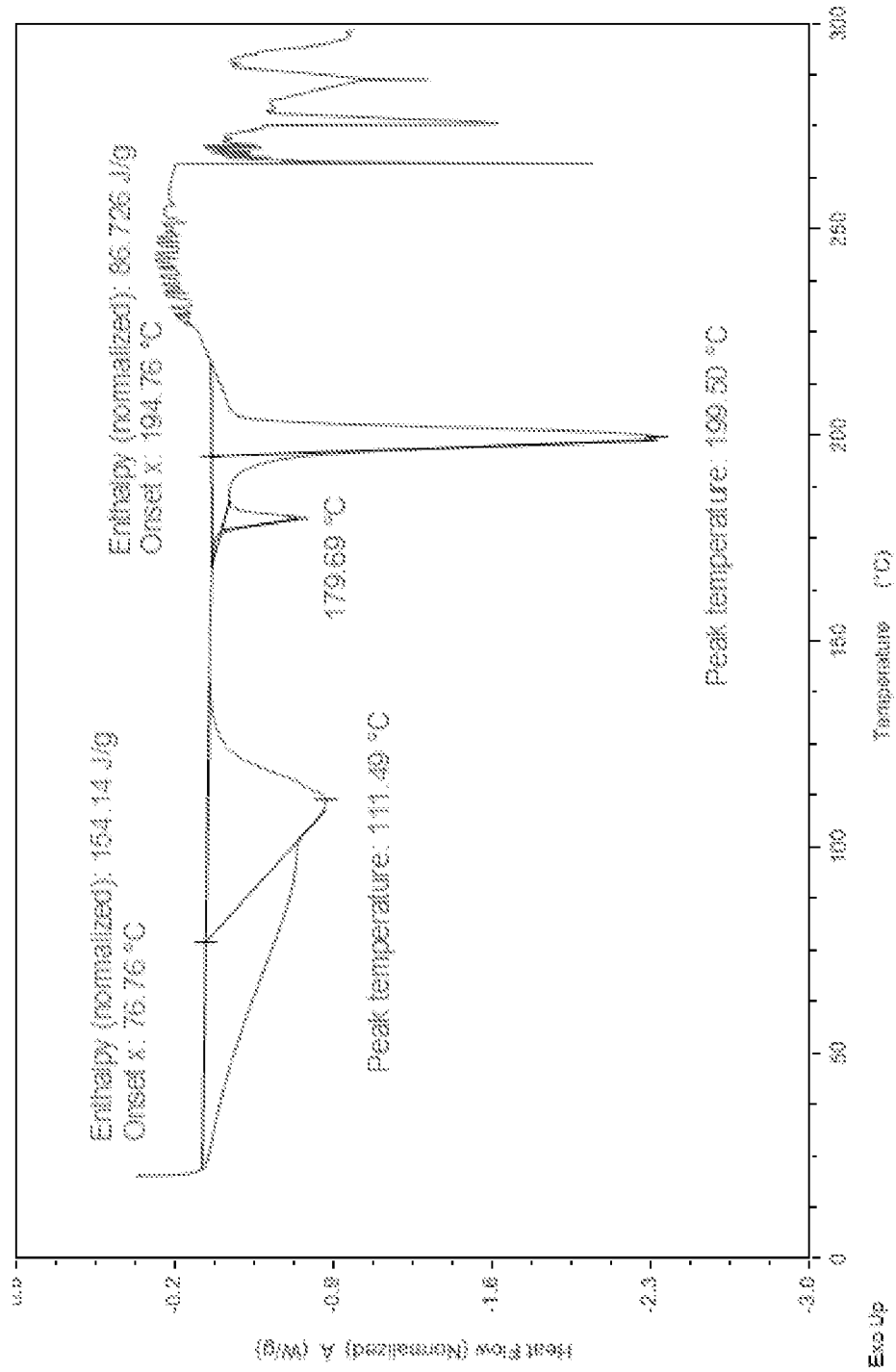
FIG. 26 shows a DSC thermogram of Compound 2 phosphate.
Figure 27:
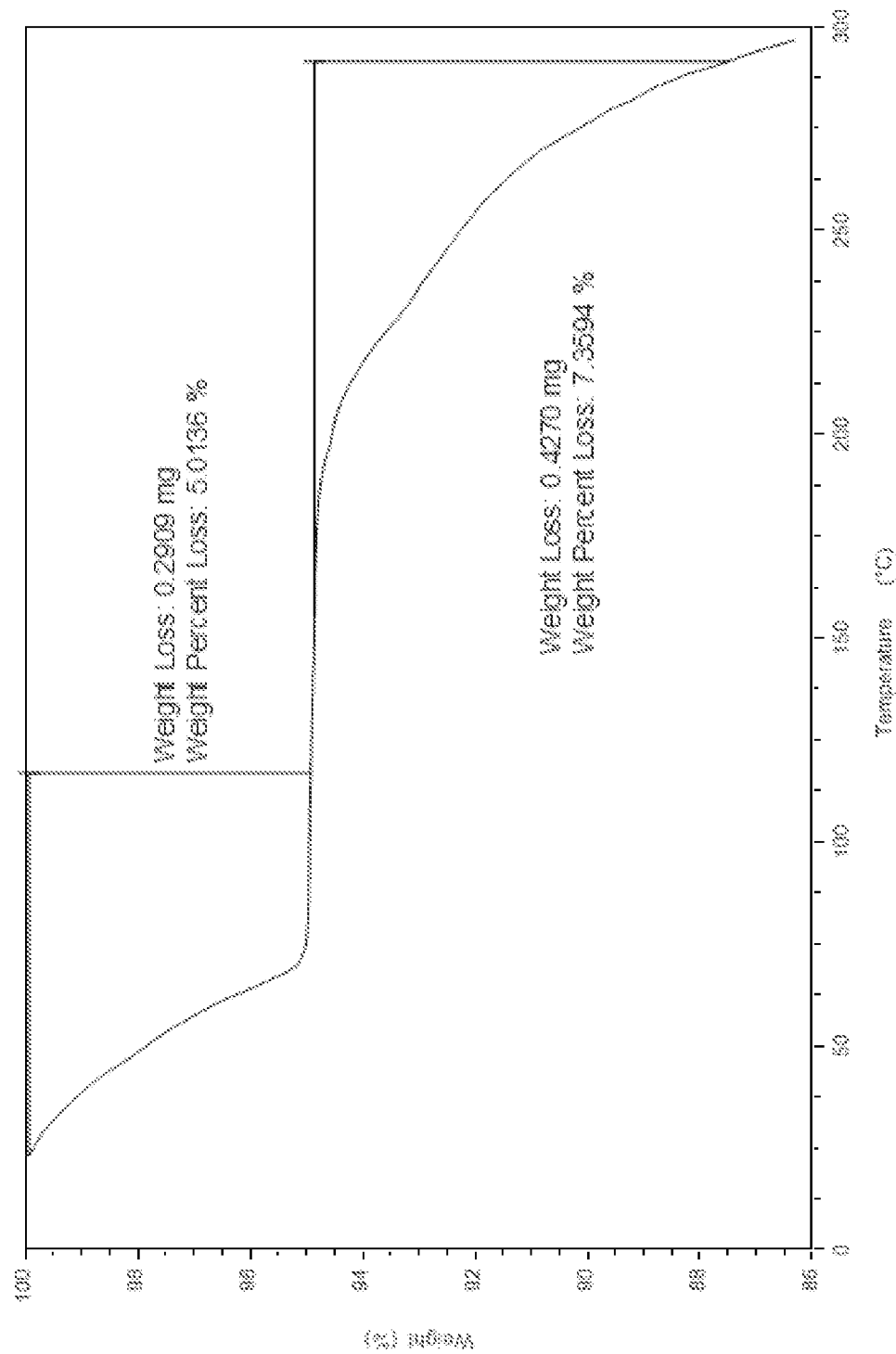
FIG. 27 shows a TGA thermogram of Compound 2 phosphate.

In some embodiments, the phosphoric acid salt of Compound 2 exhibits a DSC thermogram having endothermic peaks at temperatures of about 116° C. and about 200° C. In some embodiments, the phosphoric acid salt of Compound 2 exhibits a DSC thermogram having an endothermic peak at a temperature of about 116° C. In some embodiments, the phosphoric acid salt of Compound 2 exhibits a DSC thermogram having an endothermic peak at a temperature of about 200° C. In some embodiments, the phosphoric acid salt of Compound 2 has a DSC thermogram substantially as depicted in FIG. 26. In some embodiments, the phosphoric acid salt of Compound 2 has a TGA thermogram substantially as depicted in FIG. 27.

In some embodiments, the phosphoric acid salt of Compound 2 has at least one characteristic XRPD peak selected from about 6.7, about 10.2, about 14.5, and about 18.0 degrees 2-theta; and the phosphoric acid salt of Compound 2 exhibits a DSC thermogram having endothermic peaks at temperatures of about 116° C. and about 200° C. In some embodiments, the phosphoric acid salt of Compound 2 has at least one characteristic XRPD peak selected from about 6.7, about 10.2, about 14.5, and about 18.0 degrees 2-theta; and the phosphoric acid salt of Compound 2 exhibits a DSC thermogram having an endothermic peak at a temperature of about 116° C. In some embodiments, the phosphoric acid salt of Compound 2 has at least one characteristic XRPD peak selected from about 6.7, about 10.2, about 14.5, and about 18.0 degrees 2-theta; and the phosphoric acid salt of Compound 2 exhibits a DSC thermogram having an endothermic peak at a temperature of about 200° C.

In some embodiments, the phosphoric acid salt of Compound 2 is substantially crystalline. In some embodiments, the salt is crystalline. In some embodiments, the salt is a hydrate. In certain embodiments, the salt is a dihydrate.

Hydrochloric Acid Salts

The hydrochloric acid salt of Compound 2 can be prepared by any suitable method for preparation of hydrochloric acid addition salts. For example, Compound 2 can be combined with hydrochloric acid (e.g., about 1.0 molar eq or more) in a solvent and the resulting salt can be isolated by filtering the salt from solution. In certain embodiments, Compound 2 is combined with about 1 to about 2 molar equivalents of hydrochloric acid. In certain embodiments, Compound 2 is combined with about 1 to about 1.5 molar equivalents of hydrochloric acid. In certain embodiments, Compound 2 is combined with about 1.05 molar equivalents of hydrochloric acid. In some embodiments, the solvent is a polar solvent. In some embodiments, the solvent is a $C_{1-6}$ alkyl alcohol. In some embodiments, the solvent is methanol.

The hydrochloric acid salt of Compound 2 can be crystallized to provide a crystalline solid form. In some embodiments, the crystallization of the hydrochloric acid salt of Compound 2 comprises precipitating the hydrochloric acid salt of Compound 1 from a crystallizing solvent. In some embodiments, the crystallizing solvent is a polar solvent. In some embodiments, the crystallizing solvent is a $C_{1-6}$ alkyl alcohol. In some embodiments, the crystallizing solvent is methanol.

In some embodiments, the hydrochloric acid salt of Compound 2 has at least one characteristic XRPD peak selected from about 6.2, about 6.8, about 11.2, and about 17.3 degrees 2-theta. In some embodiments, the hydrochloric acid salt of Compound 2 has at least two characteristic XRPD peaks selected from about 6.2, about 6.8, about 11.2, and about 17.3 degrees 2-theta. In some embodiments, the hydrochloric acid salt of Compound 2 has at least three characteristic XRPD peaks selected from about 6.2, about 6.8, about 11.2, and about 17.3 degrees 2-theta. In some embodiments, the hydrochloric acid salt of Compound 2 has a characteristic XRPD peak at about 6.2 degrees 2-theta. In some embodiments, the hydrochloric acid salt of Compound 2 has a characteristic XRPD peak at about 6.8 degrees 2-theta. In some embodiments, the hydrochloric acid salt of Compound 2 has a characteristic XRPD peak at about 11.2 degrees 2-theta. In some embodiments, the hydrochloric acid salt of Compound 2 has a characteristic XRPD peak at about 17.3 degrees 2-theta.

In some embodiments, the hydrochloric acid salt of Compound 2 has at least one characteristic XRPD peak selected from about 6.2, about 6.8, about 11.2, about 12.5, about 13.6, about 17.3, about 18.4, about 21.6, and about 22.3 degrees 2-theta. In some embodiments, the hydrochloric acid salt of Compound 2 has at least two characteristic XRPD peaks selected from about 6.2, about 6.8, about 11.2, about 12.5, about 13.6, about 17.3, about 18.4, about 21.6, and about 22.3 degrees 2-theta. In some embodiments, the hydrochloric acid salt of Compound 2 has at least three characteristic XRPD peaks selected from about 6.2, about 6.8, about 11.2, about 12.5, about 13.6, about 17.3, about 18.4, about 21.6, and about 22.3 degrees 2-theta.

In some embodiments, the hydrochloric acid salt of Compound 2 has at least one characteristic XRPD peak selected from about 6.2, about 6.8, about 11.2, about 12.5, about 13.6, about 13.8, about 16.8, about 17.3, about 18.4, about 21.6, about 22.3, and about 24.1 degrees 2-theta. In some embodiments, the hydrochloric acid salt of Compound 2 has at least two characteristic XRPD peaks selected from about 6.2, about 6.8, about 11.2, about 12.5, about 13.6, about 13.8, about 16.8, about 17.3, about 18.4, about 21.6, about 22.3, and about 24.1 degrees 2-theta. In some embodiments, the hydrochloric acid salt of Compound 2 has at least three characteristic XRPD peaks selected from about 6.2, about 6.8, about 11.2, about 12.5, about 13.6, about 13.8, about 16.8, about 17.3, about 18.4, about 21.6, about 22.3, and about 24.1 degrees 2-theta.

Figure 28:
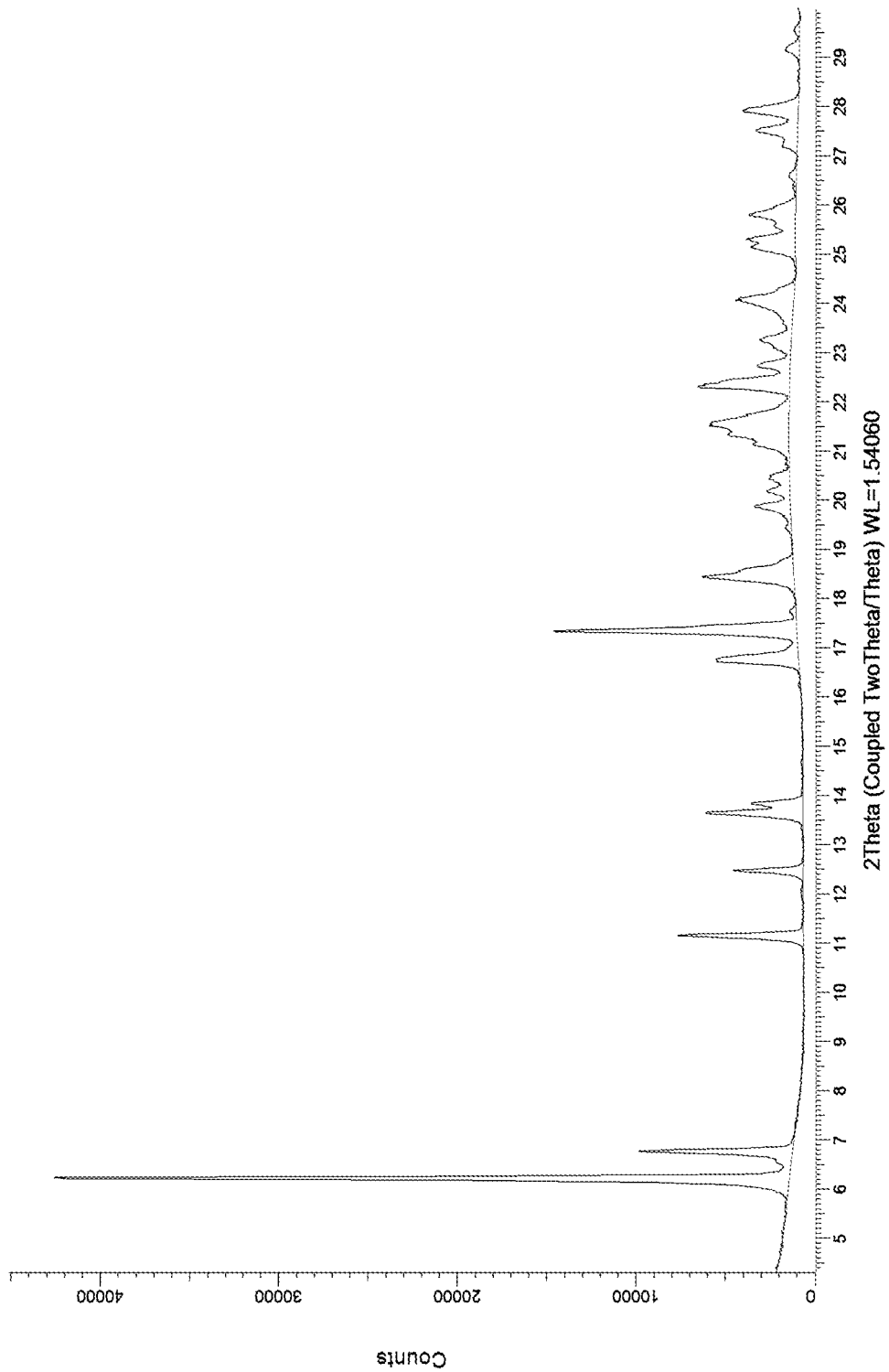
FIG. 28 shows an XRPD pattern of Compound 2 hydrochloride.

In some embodiments, the hydrochloric salt of Compound 2 has an XRPD pattern with characteristic peaks as substantially shown in FIG. 28.

Figure 29:
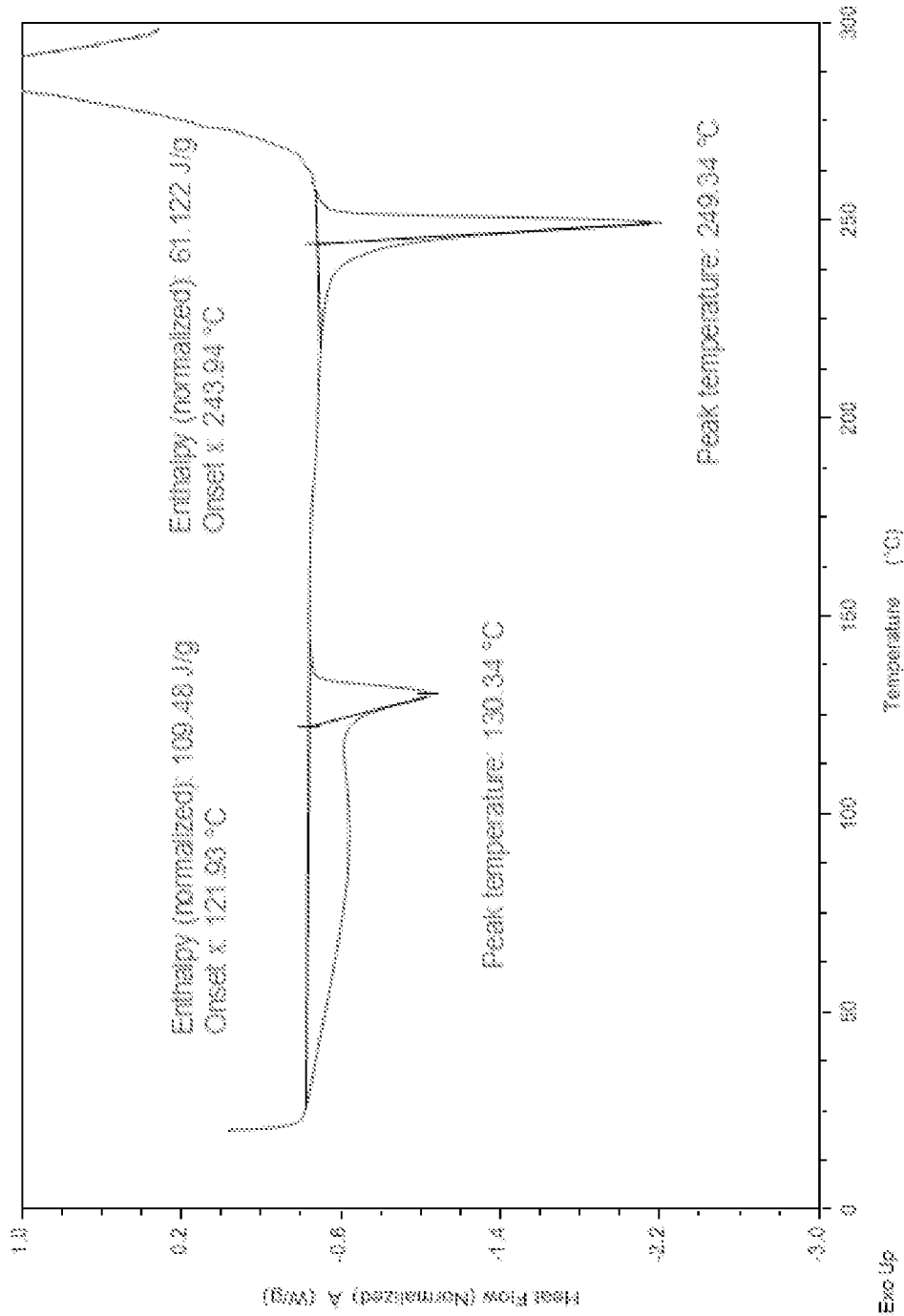
FIG. 29 shows a DSC thermogram of Compound 2 hydrochloride.
Figure 30:
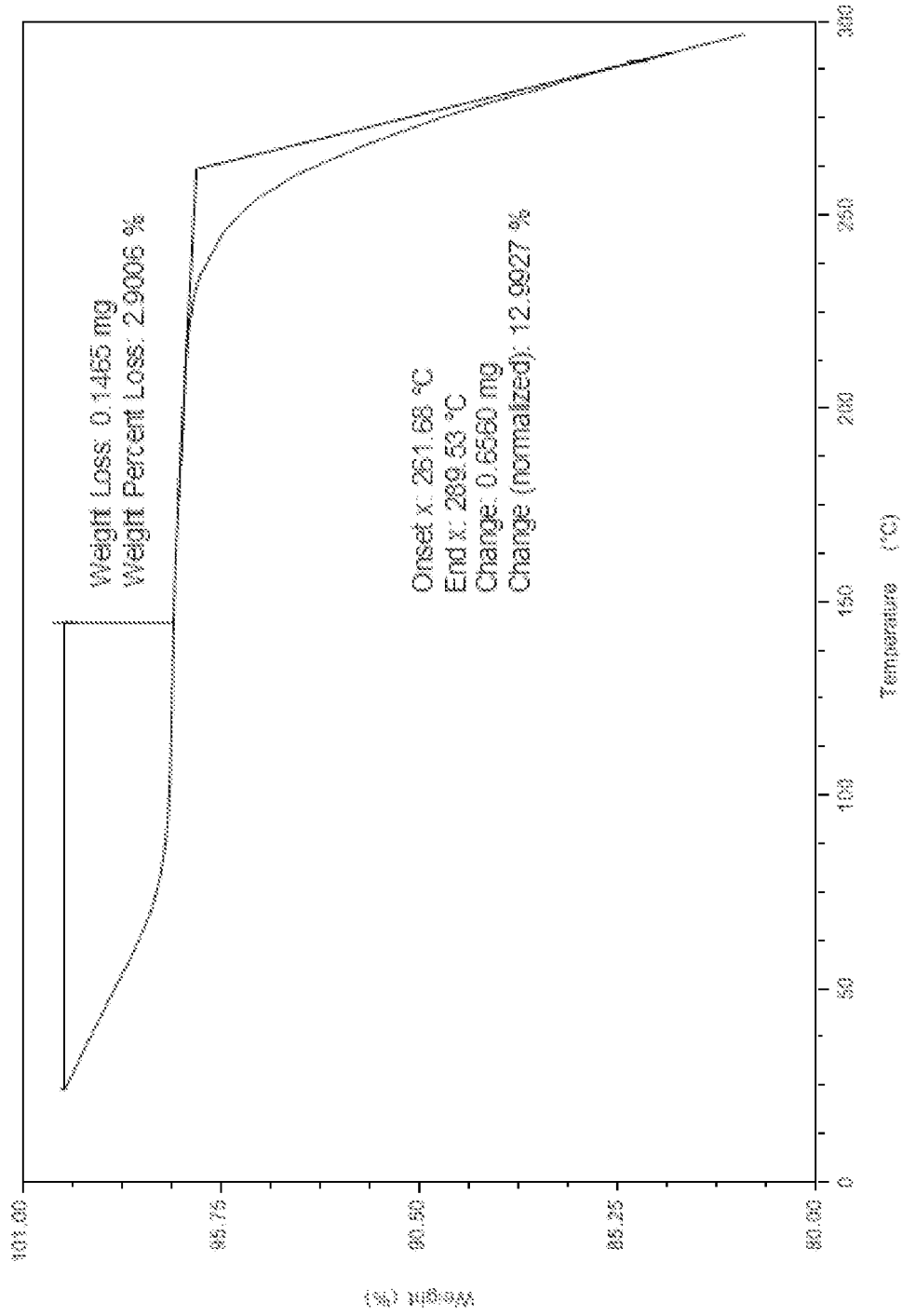
FIG. 30 shows a TGA thermogram of Compound 2 hydrochloride.

In some embodiments, the hydrochloric acid salt of Compound 2 exhibits a DSC thermogram having endothermic peaks at temperatures of about 130° C. and about 249° C. In some embodiments, the hydrochloric acid salt of Compound 2 exhibits a DSC thermogram having an endothermic peak at a temperature of about 130° C. In some embodiments, the hydrochloric acid salt of Compound 2 exhibits a DSC thermogram having an endothermic peak at a temperature of about 249° C. In some embodiments, the hydrochloric acid salt of Compound 2 has a DSC thermogram substantially as depicted in FIG. 29. In some embodiments, the hydrochloric acid salt of Compound 2 has a TGA thermogram substantially as depicted in FIG. 30.

In some embodiments, the hydrochloric acid salt of Compound 2 has at least one characteristic XRPD peak selected from about 6.2, about 6.8, about 11.2, and about 17.3 degrees 2-theta; and the hydrochloric acid salt of Compound 2 exhibits a DSC thermogram having endothermic peaks at temperatures of about 130° C. and about 249° C. In some embodiments, the hydrochloric acid salt of Compound 2 has at least one characteristic XRPD peak selected from about 6.2, about 6.8, about 11.2, and about 17.3 degrees 2-theta; and the hydrochloric acid salt of Compound 2 exhibits a DSC thermogram having an endothermic peak at a temperature of about 130° C. In some embodiments, the hydrochloric acid salt of Compound 2 has at least one characteristic XRPD peak selected from about 6.2, about 6.8, about 11.2, and about 17.3 degrees 2-theta; and the hydrochloric acid salt of Compound 2 exhibits a DSC thermogram having an endothermic peak at a temperature of about 249° C.

In some embodiments, the hydrochloric acid salt of Compound 2 is substantially crystalline. In some embodiments, the salt is crystalline.

Methods of Use

Studies have established that HPK1 is a negative regulator of T cell and B cell activation (Hu, M. C., et al., Genes Dev, 1996. 10(18): p. 2251-64; Kiefer, F., et al., EMBO J, 1996. 15(24): p. 7013-25). HPK1-deficient mouse T cells showed dramatically increased activation of TCR proximal signaling, enhanced IL-2 production, and hyper-proliferation in vitro upon anti-CD3 stimulation (Shui, J. W., et al., Nat Immunol, 2007. 8(1): p. 84-91). Similar to T cells, HPK1 knockout B cells produced much higher levels of IgM and IgG isoforms after KLH immunization and displayed hyper-proliferation potentially as a result of enhanced BCR signaling. Wang, X., et al., J Biol Chem, 2012. 287(14): p. 11037-48. Mechanistically, during TCR or BCR signaling, HPK1 is activated by LCK/ZAP70 (T cells) or SYK/LYN (B cells) mediated-Tyr379 phosphorylation and its subsequent binding to adaptor protein SLP-76 (T cells) or BLNK (B cells) (Wang, X., et al., J Biol Chem, 2012. 287(14): p. 11037-48). Activated HPK1 phosphorylates SLP-76 on Ser376 or BLNK on Thr152, leading to the recruitment of signaling molecule 14-3-3 and ultimate ubiquitination-mediated degradation of SLP-76 or BLNK (Liou, J., et al., Immunity, 2000. 12(4): p. 399-408; Di Bartolo, V., et al., J Exp Med, 2007. 204(3): p. 681-91). As SLP-76 and BLNK are essential for TCR/BCR-mediated signaling activation (e.g. ERK, phospholipase Cγ1, calcium flux, and NFAT activation), HPK1-mediated downregulation of these adaptor proteins provide a negative feedback mechanism to attenuate signaling intensity during T cell or B cell activation (Wang, X., et al., J Biol Chem, 2012. 287(14): p. 11037-48).

The bone marrow-derived dendritic cells (BDMCs) from HPK1 knockout mice showed higher expression of co-stimulatory molecules (e.g. CD80/CD86) and enhanced production of proinflammatory cytokines (IL-12, TNF-α etc), and demonstrated superior ability to stimulate T cell proliferation in vitro and in vivo as compared to wild-type DCs (Alzabin, S., et al., J Immunol, 2009. 182(10): p. 6187-94). These data suggest that HPK1 is also an important negative regulator of dendritic cell activation (Alzabin, S., et al., J Immunol, 2009. 182(10): p. 6187-94). However, the signaling mechanisms underlying HPK-1 mediated negative regulation of DC activation remains to be elucidated.

In contrast, HPK1 appears to be a positive regulator of suppressive functions of regulatory T cells (Treg) (Sawasdikosol, S. et al., The journal of immunology, 2012. 188(supplement 1): p. 163). HPK1 deficient mouse Foxp3+ Tregs were defective in suppressing TCR-induced effector T cell proliferation, and paradoxically gained the ability to produce IL-2 following TCR engagement (Sawasdikosol, S. et al., The Journal of Immunology, 2012. 188(supplement 1): p. 163). These data suggest that HPK1 is an important regulator of Treg functions and peripheral self-tolerance.

HPK1 was also involved in PGE2-mediated inhibition of CD4+ T cell activation (Ikegami, R., et al., J Immunol, 2001. 166(7): p. 4689-96). Studies published in US 2007/0087988 indicated that HPK1 kinase activity was increased by exposure to physiological concentrations of PGE2 in CD4+ T cells and this effect was mediated by PEG2-induced PKA activation. The proliferation of HPK1 deficient T cells was resistant to the suppressive effects of PGE2 (see US 2007/0087988). Therefore, PGE2-mediated activation of HPK1 may represent a novel regulatory pathway of modulating immune response.

The present disclosure provides methods of modulating (e.g., inhibiting) HPK1 activity, by contacting HPK1 with a compound of the invention, or a solid form or salt thereof. In some embodiments, the contacting can be administering to a patient a compound provided herein, or a or a solid form or salt thereof. In certain embodiments, the compounds of the present disclosure, or a solid form or salt thereof, are useful for therapeutic administration to enhance, stimulate and/or increase immunity in cancer. For example, a method of treating a disease or disorder associated with inhibition of HPK1 interaction can include administering to a patient in need thereof a therapeutically effective amount of a compound provided herein, or a solid form or salt thereof. The compounds of the present disclosure, or a solid form or salt thereof, can be used alone, in combination with other agents or therapies or as an adjuvant or neoadjuvant for the treatment of diseases or disorders, including cancers. For the uses described herein, any of the compounds of the disclosure, or a solid form or salt thereof, including any of the embodiments thereof, may be used.

Examples of cancers that are treatable using the compounds of the present disclosure, or solid forms or salts thereof include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure, or solid forms or salts thereof, include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure, or solid forms or salts thereof.

In some embodiments, cancers that are treatable using the compounds of the present disclosure, or solid forms or salts thereof, include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure, or solid forms or salts thereof, include but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention, or solid forms or salts thereof, are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the compounds provided herein, or solid forms or salts thereof, can be used in combination with one or more immune checkpoint inhibitors for the treatment of cancer as described herein. Compounds of the present disclosure, or solid forms or salts thereof, can be used in combination with one or more immune checkpoint inhibitors. Exemplary immune checkpoint inhibitors include inhibitors against immune checkpoint molecules such as CD20, CD28, CD39, CD40, CD122, CD96, CD73, CD47, GITR, CSF1R, JAK, PI3K delta, PI3K gamma, TAM, arginase, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein, or solid forms or salts thereof, can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein, or solid forms or salts thereof, can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321, GSK2831781, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is INCAGN01949, MEDI0562, MEDI6469, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure, or solid forms or salts thereof, can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure, or solid forms or salts thereof, can be used in combination with one or more metabolic enzyme inhibitors. In some embodiments, the metabolic enzyme inhibitor is an inhibitor of IDO1, TDO, or arginase. Examples of IDOL inhibitors include epacadostat, NLG919, BMS-986205, PF-06840003, IOM2983, RG-70099 and LY338196. An example of an arginase inhibitor is CB-1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure, or solid forms or salts thereof, include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure, or solid forms or salts thereof, can be used in combination with one or more other enzyme/protein/receptor inhibitors for the treatment of diseases, such as cancer. Examples of cancers include solid tumors and liquid tumors, such as blood cancers. For example, the compounds of the present disclosure, or solid forms or salts thereof, can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure, or solid forms or salts thereof, can be combined with one or more of the following inhibitors for the treatment of cancer. Non-limiting examples of inhibitors that can be combined with the compounds of the present disclosure, or solid forms or salts thereof, for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973.

Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure, or solid forms or salts thereof, can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure, or solid forms or salts thereof, can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure, or solid forms or salts thereof, can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure, or solid forms or salts thereof, can also be used in combination with lonafarnib (SCH6636), tipifarnib (R115777), L778123, BMS 214662, tezacitabine (MDL 101731), Sml1, triapine, didox, trimidox and amidox.

The compounds of the disclosure, or salts or solid forms thereof, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure, or solid forms or salts thereof, can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure, or solid forms or salts thereof, can be used in combination with tumor specific antigen such as heat shock proteins isolated from tumor tissue itself. In some embodiments, the compounds of the present disclosure, or solid forms or salts thereof, can be combined with dendritic cells immunization to activate potent anti-tumor responses.

The compounds of the present disclosure, or solid forms or salts thereof, can be used in combination with bispecific macrocyclic peptides that target Fc alpha or Fc gamma receptor-expressing effectors cells to tumor cells. The compounds of the present disclosure, or solid forms or salts thereof, can also be combined with macrocyclic peptides that activate host immune responsiveness.

The compounds of the present disclosure, or solid forms or salts thereof, can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(-)-FTC]; beta-L-FD4 (also called beta-L-D4C and named beta-L-2',3'-dicleoxy-5-fluoro-cytidene); DAPD, ((-)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

In some embodiments, the compounds of the present disclosure, or solid forms or salts thereof, can be used in combination with INCB086550.

Formulation, Dosage Forms and Administration

When employed as pharmaceuticals, the compounds of the present disclosure, or solid forms or salts thereof, can be administered in the form of pharmaceutical compositions. Thus the present disclosure provides a composition comprising the compounds of the present disclosure, or solid forms or salts thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient the compounds of the present disclosure, or solid forms or salts thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the present disclosure, or solid forms or salts thereof, may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising a compound of the present disclosure, or a solid form or salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention, or a solid form or salt thereof, can vary according to, e.g., the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the invention or a salt or solid form thereof, can be provided in an aqueous physiological buffer solution containing about 0.1 to about 10% w/v of the compound for parenteral administration. Some typical dose ranges are from about 1 □g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention, or a solid form or salt thereof, can vary according to, e.g., the particular use for which the treatment is made, the manner of administration of the compound, the health and condition of the patient, and the judgment of the prescribing physician. The proportion or concentration of a compound of the invention, or a solid form or salt thereof, in a pharmaceutical composition can vary depending upon a number of factors including dosage, chemical characteristics (e.g., hydrophobicity), and the route of administration. For example, the compounds of the invention, or solid forms or salts thereof, can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

Experimental Methods

In the below examples, X-Ray Powder Diffraction analysis was carried out on a Bruker D8 Advance ECO X-ray Powder Diffractometer (XRPD) instrument. The general experimental procedures for XRPD were: (1) X-ray radiation from copper at 1.5418 Å and LYNXEYE™ detector; (2) X-ray power at 40 kV, 25 mA; and (3) the sample powder was dispersed on a zero-background sample holder. The general measurement conditions for XRPD were: Start Angle 3 degrees; Stop Angle 30 degrees; Sampling 0.015 degrees; and Scan speed 2 degree/min.

Differential Scanning calorimetry (DSC) was carried out on a TA Instruments Differential Scanning calorimetry, Discovery DSC2500 with autosampler. The DSC instrument conditions were as follows: 20-300° C. at 10° C./min; Tzero aluminum sample pan and lid; and nitrogen gas flow at 50 mL/min.

Thermogravimetric analysis (TGA) was carried out on a TA Instruments Thermogravimetric Analyzer, Discovery TGA5500 with autosampler. The general experimental conditions for TGA were: ramp from 25° C. to 300° C. at 10° C./min; nitrogen purge gas flow at 25 mL/min; platinum sample holder.

Example 1: Preparation of Compound 1

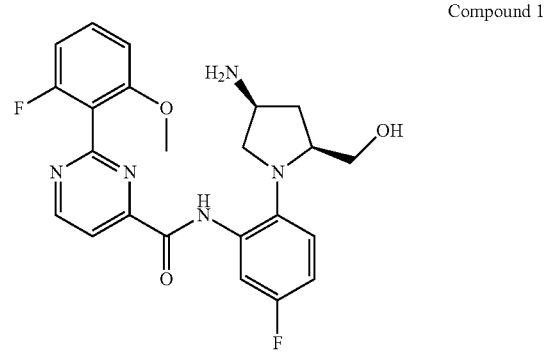 [SMILES: COc1cccc(F)c1-c1nccc(C(=O)Nc2cc(F)ccc2N2C[C@@H](N)C[C@H]2CO)n1]

Compound 1

Step 1. tert-Butyl ((3S,5S)-1-(4-fluoro-2-nitrophenyl)-5-(hydroxymethyl)pyrrolidin-3-yl)carbamate

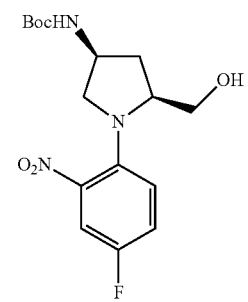

A solution of 1,4-difluoro-2-nitrobenzene (68.2 µL, 0.629 mmol) and tert-butyl ((3S,5S)-5-(hydroxymethyl)pyrrolidin-3-yl)carbamate (136 mg, 0.629 mmol) in DMSO (2.5 mL) was treated with triethylamine (131 µL, 0.943 mmol) and the reaction mixture was heated to 80° C. for 3 hrs. After cooling to r.t., the reaction mixture was diluted with DCM, washed with brine, dried over sodium sulfate and the solvent was evaporated under vacuum. The obtained crude product was used in the next step without further purification. LCMS calculated for $C_{12}H_{15}FN_3O_5$ $(M+H-C_4H_8)^+$: m/z=300.1; found 300.1.

Step 2. tert-Butyl ((3S,5S)-1-(2-amino-4-fluorophenyl)-5-(hydroxymethyl)pyrrolidin-3-yl)carbamate

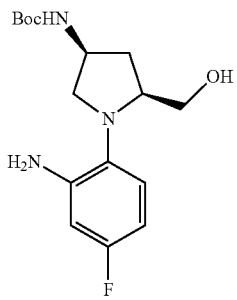 [SMILES: CC(C)(C)OC(=O)N[C@H]1C[C@@H](CO)N(c2ccc(F)cc2[N+](=O)[O-])C1]

A mixture of tert-butyl ((3S,5S)-1-(4-fluoro-2-nitrophenyl)-5-(hydroxymethyl)pyrrolidin-3-yl)carbamate (100 mg, 0.281 mmol), iron (79 mg, 1.407 mmol) and ammonium chloride (90 mg, 1.7 mmol) in THF (2 mL), water (2 mL) and methanol (2 mL) was stirred at 60° C. for 3 hrs. After cooling to r.t., the mixture was filtered through a plug of Celite and diluted with DCM. The organic phase was separated, washed with brine, dried over sodium sulfate and the solvents were evaporated under vacuum. The obtained crude product was used in the next step without further purification. LCMS calculated for $C_{16}H_{25}FN_3O_3$ (M+H)$^+$: m/z=326.2; Found: 326.2.

Step 3. N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide (Compound 1)

HATU (175 mg, 0.461 mmol) was added to a solution of tert-butyl ((3S,5S)-1-(2-amino-4-fluorophenyl)-5-(hydroxymethyl)pyrrolidin-3-yl)carbamate (100 mg, 0.307 mmol), 2-(2-fluoro-6-methoxyphenyl)pyrimidine-4-carboxylic acid (the product of Example 1, step 1, 76 mg, 0.307 mmol) and DIPEA (107 µL, 0.615 mmol) in DMF (2 mL). The reaction mixture was stirred at r.t. for 30 mins, then water was added and the precipitated product was collected by filtration, washed with water and air dried. The solid was dissolved in TFA and the resulting solution was stirred at r.t. for 10 mins. The solution was then diluted with acetonitrile and purified with prep-LCMS. LCMS calculated for $C_{23}H_{24}F_2N_5O_3$ (M+H)$^+$: m/z=456.2; Found: 456.3. Prep-LCMS (XBridge C18 column, eluting with a gradient of acetonitrile/water containing 0.1% NH$_4$OH, at flow rate of 60 mL/min). Free base: 1H NMR (600 MHz, DMSO-d$_6$) δ 9.34-9.18 (m, 1H), 8.25-8.19 (m, 1H), 8.18-8.14 (m, 1H), 7.60-7.49 (q, J=7.7 Hz, 1H), 7.49-7.43 (m, 1H), 7.08-7.02 (d, J=8.4 Hz, 1H), 7.02-6.94 (m, 2H), 3.78-3.71 (s, 3H), 3.38-3.30 (t, J=6.4 Hz, 1H), 3.30-3.23 (m, 1H), 3.23-3.17 (m, 1H), 3.17-3.10 (dd, J=11.1, 6.1 Hz, 1H), 2.95-2.88 (t, J=7.4 Hz, 1H), 2.88-2.80 (m, 1H), 2.35-2.25 (dt, J=14.1, 8.0 Hz, 1H), 1.25-1.12 (m, 1H) ppm. Prep-LCMS (XBridge C18 column, eluting with a gradient of acetonitrile/water containing 0.1% TFA, at flow rate of 60 mL/min) TFA salt: 1H NMR (600 MHz, DMSO-d6) δ10.78-10.58 (s, 1H), 9.32-9.20 (d, J=5.0 Hz, 1H), 8.24-8.08 (m, 2H), 7.93-7.77 (br, J=5.7 Hz, 2H), 7.62-7.53 (td, J=8.4, 6.8 Hz, 1H), 7.53-7.46 (dd, J=8.8, 5.7 Hz, 1H), 7.10-7.02 (m, 2H), 7.02-6.93 (t, J=8.8 Hz, 1H), 3.82-3.73 (s, 3H), 3.75-3.67 (m, 1H), 3.59-3.51 (m, 1H), 3.30-3.15 (m, 4H), 2.44-2.35 (ddd, J=13.6, 9.1, 7.2 Hz, 1H), 1.81-1.71 (dt, J=13.5, 4.3 Hz, 1H) ppm.

Example 2: Preparation of Compound 2

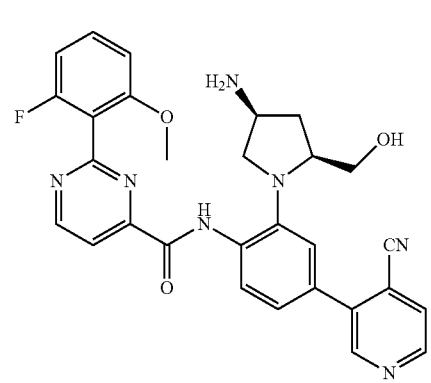

Compound 2

Step 1. tert-Butyl ((3S,5S)-1-(5-bromo-2-nitrophenyl)-5-(hydroxymethyl)pyrrolidin-3-yl)carbamate

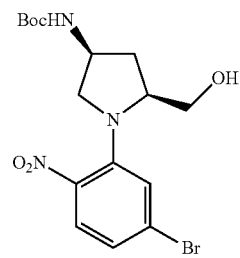 [SMILES: CC(C)(C)OC(=O)N[C@H]1C[C@@H](CO)N(c2cc(Br)ccc2[N+](=O)[O-])C1]

A solution of 4-bromo-2-fluoro-1-nitrobenzene (532 mg, 2.42 mmol) and tert-butyl ((3S,5S)-5-(hydroxymethyl)pyrrolidin-3-yl)carbamate (523 mg, 2.42 mmol) in DMSO (8 mL) was treated with triethylamine (506 3.63 mmol) and the reaction mixture was heated to 80° C. for 2 hr. After cooling to r.t., water was added and the precipitated product was collected by filtration, washed with water and air dried. It was used in the next step without further purification. LCMS calculated for $C_{12}H_{15}BrN_3O_5$ (M+H–C$_4$H$_8$)$^+$: m/z=360.0/362.0; found 360.0/362.0.

Step 2. tert-Butyl ((3S,5S)-1-(2-amino-5-bromophenyl)-5-(hydroxymethyl)pyrrolidin-3-yl)carbamate

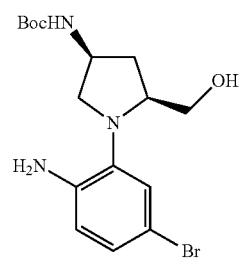

A mixture of tert-butyl ((3S,5S)-1-(5-bromo-2-nitrophenyl)-5-(hydroxymethyl)pyrrolidin-3-yl)carbamate (1 g, 2.45 mmol), iron (684 mg, 12.25 mmol) and ammonium chloride (786 mg, 14.70 mmol) in THF (5 mL), water (5 mL) and methanol (5 mL) was stirred at 60° C. for 3 hrs. After cooling to r.t., it was filtered through a plug of Celite and diluted with DCM. The organic phase was separated, washed with saturated aqueous sodium chloride, dried over sodium sulfate and the solvents were evaporated in vacuo. The obtained crude product was used in the next step without further purification. LCMS calculated for $C_{16}H_{25}BrN_3O_3$ (M+H)$^+$: m/z=386.1/388.1; Found: 386.1/388.1.

Step 3. tert-Butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate

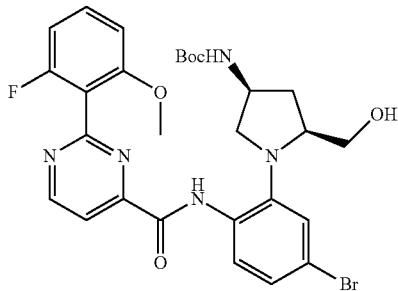 [SMILES: COc1cccc(F)c1-c1nccc(C(=O)Nc2ccc(Br)cc2N2C[C@@H](NC(=O)OC(C)(C)C)C[C@H]2CO)n1]

HATU (1196 mg, 3.15 mmol) was added to a solution of tert-butyl ((3 S,5S)-1-(2-amino-5-bromophenyl)-5-(hydroxymethyl)pyrrolidin-3-yl)carbamate (810 mg, 2.097 mmol), 2-(2-fluoro-6-methoxyphenyl)pyrimidine-4-carboxylic acid (the product of Example 1, step 1, 520 mg, 2.097 mmol) and DIPEA (732 μl, 4.19 mmol) in DMF (5 mL). The reaction mixture was stirred at r.t. for 30 mins, then water was added and the precipitated product was collected by filtration, washed with water and air dried. The solid was used in the next step without further purification. LCMS calculated for $C_{28}H_{32}BrFN_5O_5$ (M+H)$^+$: m/z=616.2/618.2; Found: 616.2/618.2.

Step 4. N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide (Compound 2)

A mixture of tert-butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate (10 mg, 0.016 mmol), 3-(4,4,5,5-tetramethyl-1,3,2-dioxaborolan-2-yl)isonicotinonitrile (9.8 mg, 0.043 mmol), Xphos Pd G2 (1.3 mg, 1.6 μmop and potassium phosphate, tribasic (6.7 mg, 0.032 mmol) was combined with 1,4-dioxane (1 mL) and water (0.1 mL) and the reaction flask was evacuated, back filled with nitrogen, then stirred at 80° C. for 1 hr. The reaction mixture was cooled to r.t., the solvents were evaporated in vacuo and TFA (1 mL) was added. The reaction mixture was stirred at r.t. for 10 min, then diluted with CH$_3$CN and water and purified with prep-LCMS. LCMS calculated for $C_{29}H_{27}FN_7O_3$ (M+H)$^+$: m/z=540.2; Found: 540.1. Prep-LCMS (XBridge C18 column, eluting with a gradient of acetonitrile/water containing 0.1% NH$_4$OH, at flow rate of 60 mL/min). Free base: $^1$H NMR (500 MHz, DMSO-d$_6$) δ9.33-9.25 (d, J=5.0 Hz, 1H), 8.98-8.93 (s, 1H), 8.84-8.78 (d, J=5.0 Hz, 1H), 8.46-8.39 (d, J=8.4 Hz, 1H), 8.22-8.18 (d, J=5.0 Hz, 1H), 8.00-7.92 (dd, J=5.1, 0.7 Hz, 1H), 7.67-7.64 (m, 1H), 7.59-7.52 (td, J=8.4, 6.8 Hz, 1H), 7.48-7.43 (dd, J=8.3, 2.1 Hz, 1H), 7.11-7.04 (d, J=8.5 Hz, 1H), 7.03-6.90 (t, J=8.8 Hz, 1H), 3.85-3.73 (s, 3H), 3.68-3.56 (m, 1H), 3.39-3.29 (m, 3H), 3.28-3.22 (d, J=4.8 Hz, 1H), 3.06-2.97 (d, J=5.4 Hz, 1H), 2.31-2.18 (dt, J=12.6, 7.5 Hz, 1H), 1.40-1.29 (dt, J=12.7, 6.2 Hz, 1H) ppm. Prep-LCMS (XBridge C18 column, eluting with a gradient of acetonitrile/water containing 0.1% TFA, at flow rate of 60 mL/min). TFA salt: $^1$H NMR (500 MHz, DMSO-d$_6$) δ10.66-10.59 (s, 1H), 9.31-9.24 (d, J=5.0 Hz, 1H), 9.03-8.94 (d, J=0.8 Hz, 1H), 8.88-8.78 (d, J=5.0 Hz, 1H), 8.34-8.24 (d, J=8.4 Hz, 1H), 8.24-8.17 (d, J=5.0 Hz, 1H), 8.04-7.95 (dd, J=5.1, 0.8 Hz, 1H), 7.92-7.82 (br, J=5.5 Hz, 2H), 7.73-7.65 (d, J=2.0 Hz, 1H), 7.61-7.54 (td, J=8.5, 6.9 Hz, 1H), 7.50-7.45 (dd, J=8.4, 2.0 Hz, 1H), 7.11-7.05 (d, J=8.5 Hz, 1H), 7.05-6.98 (t, J=8.8 Hz, 1H), 3.89-3.82 (m, 1H), 3.81-3.77 (s, 3H), 3.76-3.69 (m, 1H), 3.42-3.21 (m, 4H), 2.43-2.31 (m, 1H), 1.90-1.77 (dt, J=13.2, 5.3 Hz, 1H) ppm.

Example 3: Synthesis of Crystalline Form I of Compound 1

Form I of Compound 1 was obtained by stirring 52.63 mg of the amorphous free base in 1 mL of isopropyl alcohol (IPA) in a 4 mL clear glass vial at room temperature overnight. The crystalline solid was collected by filtration and air dried.

Form I was confirmed as a crystalline solid according to XRPD analysis. The XRPD pattern of Form I is shown in FIG. 1 and the peak data is given below in Table 1.

TABLE 1

| XRPD Peak Data for Free Base Form I. | |
|---|---|
| 2-Theta (°) | Relative Intensity (%) |
| 6.7 | 100 |
| 9.1 | 2.1 |
| 9.9 | 19.9 |
| 10.4 | 5.0 |
| 10.9 | 2.6 |
| 13.4 | 19.7 |
| 14.1 | 14.2 |
| 14.6 | 12.4 |
| 15.5 | 23.1 |
| 15.9 | 2.4 |
| 16.2 | 5.5 |
| 16.5 | 8.0 |
| 16.9 | 4.4 |
| 17.5 | 6.3 |
| 18.3 | 20.5 |
| 19.2 | 7.2 |
| 19.9 | 31.5 |
| 20.4 | 36.8 |
| 20.9 | 13.8 |
| 21.0 | 14.3 |
| 21.5 | 3.0 |
| 21.9 | 9.6 |
| 22.2 | 11.3 |
| 22.8 | 13.3 |
| 23.5 | 9.7 |
| 24.4 | 10.2 |
| 25.1 | 3.5 |
| 26.0 | 2.5 |
| 25.5 | 27.2 |
| 26.0 | 2.9 |
| 26.2 | 4.5 |

TABLE 1-continued

XRPD Peak Data for Free Base Form I.

| 2-Theta (°) | Relative Intensity (%) |
|---|---|
| 26.6 | 5.5 |
| 27.4 | 18.8 |
| 28.1 | 3.5 |
| 28.6 | 4.8 |
| 29.5 | 3.8 |

DSC analysis of the free base Form I revealed a first endothermic peak with an onset temperature of 57.3° C. and a maximum at 86.2° C. and a second endothermic peak with an onset temperature of 182.8° C. and a maximum at 183.4° C. The DSC thermogram is provided in FIG. 2.

TGA analysis of the free base Form I revealed 10.4% weight loss below 100° C. and significant weight loss above 200° C. due to decomposition of the sample. The TGA thermogram is provided in FIG. 3.

Example 4: Preparation and Characterization of Compound 1 Phosphate Salt 104.5 mg of Compound 1 was added in 1 mL of methanol in a 4 mL clear glass vial with stirring. To the solution/suspension, 60.2 μL of 4M aqueous phosphoric acid (1.05 eq) was added and mixed well. The solution was evaporated at room temperature to dryness. The resultant solid was treated with 1 mL of water and stirred for 2 hours at room temperature. The solid phosphate salt was collected by filtration and air dried. The salt ratio between free base and phosphoric acid was determined to be 1.05 by NMR analysis.

The phosphate salt was confirmed as a crystalline solid according to XRPD analysis. The XRPD pattern of the phosphate salt is shown in FIG. 4 and the peak data is given below in Table 2.

TABLE 2

XRPD Peak Data for Phosphate Salt.

| 2-Theta (°) | Relative Intensity (%) |
|---|---|
| 6.3 | 63.3 |
| 6.4 | 100 |
| 7.0 | 65.3 |
| 8.9 | 22.2 |
| 10.7 | 2.3 |
| 11.2 | 47.8 |
| 11.4 | 5.4 |
| 12.5 | 60.8 |
| 12.8 | 10.0 |
| 14.1 | 19.1 |
| 14.4 | 13.1 |
| 15.4 | 8.0 |
| 15.8 | 33.0 |
| 16.8 | 10.8 |
| 17.0 | 33.5 |
| 17.2 | 1.5 |
| 18.0 | 37.1 |
| 18.8 | 11.8 |
| 19.2 | 8.3 |
| 19.4 | 17.3 |
| 19.9 | 64.7 |
| 20.3 | 17.6 |
| 20.7 | 4.8 |
| 20.9 | 1.1 |
| 21.2 | 21.8 |
| 21.6 | 21.6 |
| 21.9 | 7.3 |
| 22.1 | 4.8 |
| 22.6 | 32.4 |
| 22.9 | 90.0 |
| 23.1 | 13.6 |
| 23.4 | 6.4 |
| 23.7 | 3.1 |
| 23.9 | 1.9 |
| 24.5 | 48.3 |
| 25.2 | 55.7 |
| 26.2 | 15.0 |
| 26.6 | 22.1 |
| 27.0 | 19.4 |
| 27.5 | 13.5 |
| 28.2 | 2.3 |
| 28.4 | 15.5 |
| 28.9 | 6.1 |
| 29.1 | 2.1 |
| 29.5 | 3.0 |

DSC analysis of phosphate salt revealed a first endothermic peak with an onset temperature of 56.6° C. and a maximum at 92.5° C. and a second endothermic peak with an onset temperature of 220.3° C. and a maximum at 228.9° C. The DSC thermogram is provided in FIG. 5. TGA analysis of the phosphate salt revealed 18.7% weight loss below 100° C. and significant weight loss above 200° C. due to decomposition of the sample. The TGA thermogram is provided in FIG. 6.

Example 5: Preparation and Characterization of Compound 1 Hydrochloride Salt 112.4 mg of Compound 1 was combined with 1 mL of methanol in a 4 mL clear glass vial with stirring. To the solution/suspension, 86.4 μL of 3M aqueous HCl (1.05 eq) was added and mixed well. The solution was evaporated at room temperature to dryness. The resultant solid was treated with 1 mL of water and stirred for 2 hours at room temperature. The solid hydrochloride salt was collected by filtration and air dried.

The hydrochloride salt was confirmed as a crystalline solid according to XRPD analysis. The XRPD pattern of hydrochloride salt is shown in FIG. 7 and the peak data is given below in Table 3.

TABLE 3

XRPD Peak Data for Hydrochloride Salt.

| 2-Theta (°) | Relative Intensity (%) |
|---|---|
| 4.5 | 73 |
| 6.0 | 5.0 |
| 6.7 | 100 |
| 9.1 | 25.3 |
| 9.7 | 6.1 |
| 10.6 | 12.1 |
| 11.0 | 15.0 |
| 11.5 | 0.6 |
| 12.1 | 1.8 |
| 12.7 | 13.8 |
| 12.9 | 3.6 |
| 13.5 | 18.5 |
| 13.9 | 7.1 |
| 14.4 | 1.0 |
| 14.8 | 2.4 |
| 15.5 | 30.6 |
| 16.5 | 14.0 |
| 17.1 | 22.7 |

TABLE 3-continued

XRPD Peak Data for Hydrochloride Salt.

| 2-Theta (°) | Relative Intensity (%) |
|---|---|
| 17.2 | 7.9 |
| 18.2 | 17.2 |
| 18.5 | 1.3 |
| 19.2 | 10.7 |
| 19.5 | 3.6 |
| 20.0 | 4.1 |
| 20.3 | 3.6 |
| 20.9 | 8.1 |
| 21.2 | 15.4 |
| 21.4 | 11.1 |
| 21.8 | 5.1 |
| 22.2 | 3.1 |
| 22.5 | 3.0 |
| 22.7 | 20.8 |
| 23.2 | 21.8 |
| 23.4 | 36.3 |
| 23.8 | 4.9 |
| 24.2 | 1.6 |
| 24.6 | 6.8 |
| 25.3 | 11.3 |
| 26.0 | 7.8 |
| 26.8 | 5.3 |
| 27.4 | 4.3 |
| 28.2 | 6.4 |
| 28.6 | 3.8 |
| 28.9 | 4.9 |
| 29.3 | 4.8 |

DSC analysis of the hydrochloride salt revealed a first endothermic peak with an onset temperature of 106.3° C. and a maximum at 107.2° C. and a second endothermic peak with an onset temperature of 230.9° C. and a maximum at 232.7° C. An exothermic peak was also observed around 160-175° C. The DSC thermogram is provided in FIG. 8.

TGA analysis of the hydrochloride salt revealed 11.2% weight loss below 125° C. and significant weight loss above 225° C. due to decomposition of the sample. The TGA thermogram is provided in FIG. 9.

Example 6: Preparation and Characterization of Compound 1 L-Tartrate Salt 98.9 mg of Compound 1 was combined with 2 mL of methanol in a 4 mL clear glass vial with stirring. To the solution/suspension, 37.53 mg of L-tartaric acid (1.15 eq) was added and mixed well. Solid precipitated quickly. The resultant suspension was stirred for 1 h at room temperature. The solid L-tartrate salt was collected by filtration and air dried. The dried solid was treated with 2 mL of water in a 4 mL clear glass vial and stirred overnight at room temperature. The recrystallized solid of the L-tartrate salt was collected by filtration and dried at 30° C. under vacuum overnight. The salt ratio between the free base and L-tartaric acid was determined to be 1.0 by NMR analysis.

The L-tartrate salt was confirmed as a crystalline solid according to XRPD analysis. The XRPD pattern of the L-tartrate salt is shown in FIG. 10 and the peak data is given below in Table 4.

TABLE 4

XRPD Peak Data for L-Tartrate Salt.

| 2-Theta (°) | Relative Intensity (%) |
|---|---|
| 4.9 | 29.1 |
| 7.5 | 10.9 |
| 7.9 | 31.7 |
| 9.0 | 5.7 |
| 9.8 | 100 |
| 10.0 | 12.0 |
| 10.5 | 18.2 |
| 12.4 | 4.4 |
| 13.0 | 3.4 |
| 13.7 | 26.4 |
| 14.4 | 6.3 |
| 14.7 | 23.3 |
| 15.1 | 4.7 |
| 15.4 | 2.7 |
| 15.9 | 72.1 |
| 16.0 | 63.5 |
| 16.5 | 6.1 |
| 16.9 | 71.6 |
| 17.5 | 7.3 |
| 18.1 | 30.1 |
| 18.3 | 5.4 |
| 18.8 | 10.7 |
| 19.6 | 71.2 |
| 20.2 | 6.1 |
| 20.8 | 24.8 |
| 21.2 | 19.3 |
| 22.4 | 7.5 |
| 23.0 | 60.2 |
| 23.4 | 7.7 |
| 24.0 | 13.0 |
| 24.7 | 23.3 |
| 24.8 | 13.9 |
| 25.2 | 10.6 |
| 25.9 | 23.8 |
| 26.3 | 8.0 |
| 26.9 | 8.0 |
| 27.7 | 4.8 |
| 28.2 | 3.1 |
| 28.7 | 9.9 |
| 29.1 | 1.8 |
| 29.6 | 5.7 |

DSC analysis of the L-tartrate salt revealed a first endothermic peak with an onset temperature of 76.4° C. and a maximum at 101.5° C. and a second endothermic peak with an onset temperature of 213.9° C. and a maximum at 216.6° C. The DSC thermogram is provided in FIG. 11. TGA analysis of the L-Tartrate salt revealed 6.3% weight loss below 100° C. and significant weight loss above 200° C. due to decomposition of the sample. The TGA thermogram is provided in FIG. 12.

Example 7: Preparation and Characterization of Compound 1 Malate Salt 64.4 mg of Compound 1 was treated with 1 mL of methanol in a 4 mL clear glass vial with stirring. To the solution/suspension, 23.0 mg of (−)-L-malic acid (1.2 eq) was added and mixed well. The resultant solution was evaporated at room temperature to dryness. The resultant solid was treated with 1 mL of methanol and stirred for 2 hours at room temperature. The solid of the malate salt was collected by filtration and air dried. The salt ratio between the free base and malic acid was determined to be 1.0 by NMR analysis.

The malate salt was confirmed as a crystalline solid according to XRPD analysis. The XRPD pattern of the malate salt is shown in FIG. 13 and the peak data is given below in Table 5.

TABLE 5

XRPD Peak Data for Malate Salt.

| 2-Theta (°) | Relative Intensity (%) |
|---|---|
| 5.2 | 54.6 |
| 7.9 | 17.8 |
| 8.2 | 6.9 |
| 9.3 | 0.6 |
| 10.4 | 100 |
| 11.3 | 8.0 |
| 12.5 | 5.5 |
| 12.8 | 7.3 |
| 13.4 | 6.7 |
| 14.3 | 15.7 |
| 14.7 | 5.6 |
| 15.8 | 40.3 |
| 16.6 | 47.6 |
| 17.3 | 3.2 |
| 18.0 | 43.8 |
| 18.3 | 8.1 |
| 19.2 | 14.5 |
| 20.4 | 5.5 |
| 21.0 | 80.1 |
| 21.2 | 73.2 |
| 21.8 | 3.5 |
| 22.9 | 12.0 |
| 23.7 | 10.0 |
| 24.3 | 7.6 |
| 24.9 | 11.0 |
| 25.4 | 9.1 |
| 25.9 | 15.7 |
| 27.1 | 8.3 |
| 28.1 | 1.3 |
| 28.7 | 3.1 |
| 29.5 | 4.8 |

DSC analysis of the malate salt revealed a first endothermic peak with an onset temperature of 23.7° C. and a maximum at 71.2° C. and a second endothermic peak with an onset temperature of 195.9° C. and a maximum at 198.4° C. The DSC thermogram is provided in FIG. 14.

TGA analysis of the malate salt revealed 1.5% weight loss below 100° C. and significant weight loss above 200° C. due to decomposition of the sample. The TGA thermogram is provided in FIG. 15.

Example 8: Preparation and Characterization of Compound 1 Camsylate Salt 62.17 mg of Compound 1 was treated with 1 mL of methanol in a 4 mL clear glass vial with stirring. To the solution/suspension, 35.4 mg of (1S)-(+)-10-camphorsulfonic acid (1.1 eq) was added and mixed well. The resultant solution was evaporated at room temperature to dryness. The resultant solid was treated with 1 mL of water and stirred for 2 hours at room temperature. The solid of the camsylate salt was collected by filtration and air dried. The salt ratio between the free base and (1S)-(+)-10-camphorsulfonic acid was determined to be 1.0 by NMR analysis.

The camsylate salt was confirmed as a crystalline solid according to XRPD analysis. The XRPD pattern of the camsylate salt is shown in FIG. 16 and the peak data is given below in Table 6.

TABLE 6

XRPD Peak Data for Camsylate Salt.

| 2-Theta (°) | Relative Intensity (%) |
|---|---|
| 4.9 | 90.7 |
| 5.9 | 96.6 |
| 8.1 | 1.8 |
| 9.8 | 17.5 |
| 10.1 | 6.5 |
| 10.9 | 32.4 |
| 11.8 | 2.7 |
| 12.2 | 25.4 |
| 12.8 | 9.1 |
| 13.2 | 3.1 |
| 14.0 | 15.7 |
| 14.4 | 67.9 |
| 15.0 | 84.0 |
| 15.1 | 100 |
| 15.7 | 35.5 |
| 16.2 | 27.9 |
| 16.5 | 28.2 |
| 17.6 | 7.7 |
| 18.5 | 10.1 |
| 19.2 | 4.0 |
| 19.8 | 45.9 |
| 20.1 | 37.9 |
| 20.5 | 15.8 |
| 20.9 | 24.7 |
| 23.0 | 6.5 |
| 23.4 | 5.7 |
| 24.1 | 3.5 |
| 25.8 | 43.3 |
| 26.5 | 29.6 |
| 27.6 | 9.2 |
| 28.1 | 4.5 |
| 28.8 | 9.8 |

DSC analysis of the camsylate salt revealed a first endothermic peak with an onset temperature of 21.6° C. and a maximum at 64.4° C. and a second major endothermic peak with an onset temperature of 227.2° C. and a maximum at 235.6° C. The DSC thermogram is provided in FIG. 17.

TGA analysis of the camsylate salt revealed 0.9% weight loss below 150° C. and significant weight loss above 200° C. due to decomposition of the sample. The TGA thermogram is provided in FIG. 18.

Example 9: Preparation and Characterization of Compound 1 Mandelate Salt 65.18 mg of Compound 1 was dissolved in 1 mL of methanol in a 4 mL clear glass vial with stirring. To the solution, 26.58 mg of (S)-(+)-mandelic acid (1.2 eq) was added and mixed well. The resultant solution was evaporated at room temperature to dryness. The resultant oil was treated with 1 mL of water and stirred for 2 hours at room temperature. The solid of the mandelate salt was collected by filtration and air dried. The salt ratio between the free base and (S)-(+)-mandelic acid was determined to be 1.1 by NMR analysis.

The mandelate salt was confirmed as a crystalline solid according to XRPD analysis. The XRPD pattern of the mandelate salt is shown in FIG. 19 and the peak data is given below in Table 7.

TABLE 7

XRPD Peak Data for Mandelate Salt.

| 2-Theta (°) | Relative Intensity (%) |
|---|---|
| 4.2 | 100 |
| 5.0 | 33.2 |
| 5.4 | 30.4 |

TABLE 7-continued

XRPD Peak Data for Mandelate Salt.

| 2-Theta (°) | Relative Intensity (%) |
|---|---|
| 5.8 | 46.6 |
| 6.9 | 32.1 |
| 8.4 | 2.6 |
| 8.9 | 1.6 |
| 10.1 | 13.3 |
| 10.4 | 2.6 |
| 11.0 | 5.4 |
| 12.0 | 8.1 |
| 12.6 | 11.2 |
| 13.0 | 5.8 |
| 13.4 | 8.4 |
| 13.9 | 16.8 |
| 14.2 | 25.1 |
| 15.0 | 23.6 |
| 15.3 | 28.9 |
| 16.1 | 7.2 |
| 16.4 | 16.3 |
| 17.1 | 15.3 |
| 17.6 | 8.0 |
| 18.0 | 2.4 |
| 18.7 | 20.0 |
| 19.0 | 42.4 |
| 19.6 | 36.7 |
| 20.1 | 10.1 |
| 20.2 | 13.2 |
| 20.7 | 3.2 |
| 21.0 | 10.8 |
| 21.6 | 15.7 |
| 22.0 | 10.8 |
| 22.3 | 16.2 |
| 23.0 | 9.6 |
| 23.8 | 13.9 |
| 24.4 | 10.5 |
| 25.0 | 17.2 |
| 25.5 | 15.7 |
| 25.9 | 13.4 |
| 26.3 | 13.7 |
| 26.9 | 4.1 |
| 27.3 | 13.3 |
| 27.7 | 10.0 |
| 28.1 | 3.4 |
| 28.4 | 3.8 |
| 29.3 | 1.9 |

DSC analysis of the mandelate salt revealed a first endothermic peak with an onset temperature of 81.5° C. and a maximum at 92.8° C. and a second endothermic peak with an onset temperature of 187.5° C. and a maximum at 217.4° C. The DSC thermogram is provided in FIG. 20.

TGA analysis of the mandelate salt revealed 4.6% weight loss below 150° C. and significant weight loss above 170° C. due to decomposition of the sample. The TGA thermogram is provided in FIG. 21.

Example 10: Preparation and Characterization of Compound 1 Citrate Salt

A 2 L round bottom flask was charged with Compound 1 (59.7 g, 131 mmol) and acetone (600 mL). The mixture was stirred at ambient temperature for 30 min until a solution was obtained. Citric acid, monohydrate (28.9 g, 138 mmol) was charged as a solution in 60 mL water. The mixture was stirred at room temperature for 16 h. The precipitate was collected by vacuum filtration and the wet cake was washed with 3×50 mL acetone (also used to rinse the vessel), then dried by pulling vacuum through the wet cake for 5 h. The solids were then dissolved in water at 80° C. (about 20 volumes needed to dissolve most of the sample). The mixture was polish filtered, then slowly cooled. After 15 h, the precipitate was collected by filtration. The wet cake was washed with 20 mL of cold water, then with 100 mL of heptane and dried by pulling vacuum through the wet cake for 5 h. The pale yellow sample was dried in a 50° C. vacuum oven for 48 h to yield 66.2 g of the citrate salt (78% yield). MUD conforms. HPLC purity=99.1% at 254 nm. KF=<0.1%. MS: 456.2 (M+H)$^+$. $^1$H NMR (600 MHz, DMSO-$d_6$) d 10.72 (s, 1H), 9.28 (d, J=5.0 Hz, 1H), 8.20-8.13 (m, 2H), 7.60-7.48 (m, 2H), 7.09-6.95 (m, 3H), 3.77 (s, 3H), 3.71-3.68 (br m, 1H), 3.55-3.51 (br m, 1H), 3.27-3.15 (m, 4H), 2.59-2.55 and 2.52-2.48 (citrate peaks, 4H), 2.45-2.36 (m, 1H), 1.77-1.71 (m, 1H).

The citrate salt was confirmed as a crystalline solid according to XRPD analysis. The salt ratio between the free base and citric acid was determined to be 1.0 by NMR analysis. The XRPD pattern of the citrate salt is shown in FIG. 22 and the peak data is given below in Table 8.

TABLE 8

XRPD Peak Data for Citrate Salt.

| 2-Theta (°) | Relative Intensity (%) |
|---|---|
| 6.1 | 1.1 |
| 6.6 | 0.3 |
| 7.3 | 26.9 |
| 9.0 | 50.4 |
| 11.3 | 2.6 |
| 12.2 | 6.4 |
| 13.3 | 2.1 |
| 13.6 | 54.2 |
| 13.9 | 9.9 |
| 14.6 | 1.3 |
| 14.9 | 12.6 |
| 16.2 | 4.0 |
| 16.4 | 5.7 |
| 16.6 | 26.8 |
| 17.0 | 2.3 |
| 17.8 | 1.3 |
| 18.1 | 51.7 |
| 18.3 | 100 |
| 18.8 | 12.6 |
| 19.5 | 40.9 |
| 20.1 | 33.9 |
| 20.4 | 9.4 |
| 20.9 | 47.6 |
| 21.6 | 23.8 |
| 21.8 | 12.8 |
| 22.0 | 4.2 |
| 22.4 | 30.8 |
| 22.7 | 10.0 |
| 23.5 | 9.5 |
| 23.8 | 2.4 |
| 24.1 | 10.2 |
| 24.5 | 29.4 |
| 24.9 | 2.8 |
| 25.3 | 23.6 |
| 25.7 | 16.3 |
| 26.4 | 7.6 |
| 26.8 | 8.4 |
| 27.3 | 24.2 |
| 27.5 | 4.7 |
| 28.0 | 34.7 |
| 28.4 | 4.5 |
| 28.9 | 1.0 |
| 29.1 | 0.4 |
| 29.5 | 16.3 |
| 29.8 | 13.2 |

DSC analysis of the citrate salt revealed one major endothermic peak with an onset temperature of 205.8° C. and a maximum at 210.0° C. The DSC thermogram is provided in FIG. 23.

TGA analysis of the citrate salt revealed 0.8% weight loss below 200° C. and significant weight loss above 200° C. due to decomposition of the sample. The TGA thermogram is provided in FIG. 24.

Example 11: Compound 2 Phosphate Salt

A 3 L round bottom flask was charged with Compound 2 (21.5 g, 39.8 mmol) and acetone (1000 mL). The resulting solution was stirred at room temperature for 15 min. A solution of 1 M aqueous phosphoric acid (41.8 mL, 41.8 mmol) was added over 5 min. The resulting thick slurry was stirred at room temperature for 16 h then vacuum filtered. The wet cake was washed with 3×50 mL acetone (also used to rinse the vessel), then washed with 100 mL heptane and dried by pulling vacuum through the wet cake for 5 h. The pale yellow sample was dried in a 50° C. vacuum oven for 48 h to yield 25.1 g of the monophosphate dihydrate salt (94% yield). XRPD conforms. HPLC purity=98.7% at 254 nm. KF=5.2%. MS: 540.2 (M+H)$^+$. $^1$H NMR (500 MHz, DMSO-d$_6$) d 10.78 (br s, 1H), 9.29 (d, J=5.0 Hz, 1H), 8.96 (d, J=0.9 Hz, 114), 8.81 (d, J=5.0 Hz, 1H), 8.36 (d, J=8.4 Hz, 1H), 8.19 (d, J=5.0 Hz, 1H), 7.97 (dd, J=5.1, 0.8 Hz, 1H), 7.64 (d, J=2.1 Hz, 1H), 7.60-7.50 (td, J=8.5, 6.9 Hz, 1H), 7.49-7.43 (dd, J=8.3, 2.0 Hz, 1H), 7.11-6.96 (m, 2H), 3.79 (s, 3H), 3.75 (br m, 1H), 3.57-3.48 (br m, 1H), 3.33-3.26 (m, 2H), 3.24-3.18 (m, 2H), 2.36-2.27 (dt, J=13.2, 7.8 Hz, 1H), 1.78-1.69 (dt, J=12.1, 5.2 Hz, 1H). Phosphate salt ratio was determined by $^{31}$P NMR using triphenyl phosphate as an internal standard.

The phosphate salt was confirmed as a crystalline solid according to XRPD analysis. The salt ratio between the free base and phosphoric acid was determined to be 1.0 by NMR analysis. The XRPD pattern of the phosphate salt is shown in FIG. 25 and the peak data is given below in Table 9.

TABLE 9

XRPD Peak Data for Phosphate Salt.

| 2-Theta (°) | Relative Intensity (%) |
|---|---|
| 5.9 | 11.8 |
| 6.3 | 5.5 |
| 6.7 | 60.6 |
| 10.2 | 39.5 |
| 11.0 | 11.0 |
| 11.9 | 15.6 |
| 12.6 | 4.2 |
| 13.4 | 24.1 |
| 13.7 | 1.1 |
| 14.5 | 52.7 |
| 15.5 | 37.1 |
| 15.9 | 24.7 |
| 16.1 | 2.9 |
| 16.5 | 40.8 |
| 17.4 | 36.3 |
| 18.0 | 100 |
| 18.3 | 3.2 |
| 18.8 | 6.8 |
| 19.0 | 18.6 |
| 19.2 | 28.8 |
| 19.8 | 19.0 |
| 20.0 | 15.1 |
| 20.4 | 57.3 |
| 21.2 | 13.3 |
| 21.6 | 0.7 |
| 22.0 | 25.7 |
| 22.2 | 26.0 |
| 23.0 | 37.9 |
| 23.3 | 65.2 |
| 23.6 | 26.2 |
| 24.0 | 6.9 |
| 24.7 | 42.6 |
| 25.2 | 15.5 |
| 25.7 | 11.5 |
| 26.2 | 23.0 |
| 26.5 | 6.2 |
| 27.1 | 10.7 |
| 27.3 | 7.4 |
| 27.5 | 6.6 |
| 28.0 | 21.5 |
| 28.3 | 17.3 |
| 28.9 | 4.6 |
| 29.3 | 11.6 |
| 29.5 | 6.6 |

The Compound 2 phosphate salt was characterized by DSC. DSC analysis of the phosphate salt revealed one major endothermic peak with an onset temperature of 76.8° C. and a maximum at 115.5° C. and a second major endothermic peak with an onset temperature of 194.8° C. and a maximum at 199.5° C. A small endothermic peak with a maximum at 179.7° C. was also observed. The DSC thermogram is provided in FIG. 26.

TGA analysis of the phosphate salt revealed 5.0% weight loss below 125° C. and significant weight loss above 175° C. due to decomposition of the sample. Water content was determined to be 5.2-5.3% by Karl Fischer, which suggests the phosphate salt is possibly a di-hydrate. The TGA thermogram is provided in FIG. 27.

Example 12: Compound 2 Hydrochloride Salt 53.83 mg of Compound 2 free base was dissolved in 1 mL of methanol in a 4 mL clear glass vial with stirring. To the solution, 35 μL of aqueous 3M HCl (1.05 eq) was added and mixed well. The solution was evaporated without cap at room temperature to dryness. To the resulted solid, 1 mL of MeOH was added and stirred for 2 hours at room temperature. The solid of the hydrochloride salt was collected by filtration and air dried.

The hydrochloride salt was confirmed as a crystalline solid according to XRPD analysis. The XRPD pattern of the hydrochloride salt is shown in FIG. 28 and the peak data is given below in Table 10.

TABLE 10

XRPD Peak Data for Hydrochloride Salt.

| 2-Theta (°) | Relative Intensity (%) |
|---|---|
| 6.2 | 100 |
| 6.8 | 21.1 |
| 11.2 | 17.1 |
| 12.0 | 0.2 |
| 12.5 | 9.5 |
| 13.6 | 13.2 |
| 13.8 | 7.0 |
| 14.7 | 0.3 |
| 16.3 | 0.3 |
| 16.8 | 11.3 |
| 17.3 | 33.2 |
| 17.7 | 0.8 |
| 18.4 | 12.6 |
| 18.3 | 3.5 |
| 19.5 | 0.7 |
| 19.9 | 4.9 |
| 20.2 | 3.1 |

TABLE 10-continued

XRPD Peak Data for Hydrochloride Salt.

| 2-Theta (°) | Relative Intensity (%) |
|---|---|
| 20.4 | 2.6 |
| 21.1 | 4.9 |
| 21.3 | 8.4 |
| 21.6 | 10.8 |
| 22.3 | 11.7 |
| 22.7 | 4.5 |
| 23.1 | 2.3 |
| 23.3 | 4.4 |
| 24.1 | 7.9 |
| 23.7 | 1.6 |
| 25.1 | 6.2 |
| 25.3 | 6.7 |
| 25.8 | 6.3 |
| 26.6 | 1.0 |
| 27.2 | 1.9 |
| 27.5 | 5.7 |
| 27.9 | 7.6 |
| 29.2 | 1.8 |
| 29.6 | 0.7 |

DSC analysis of the hydrochloride salt revealed first endothermic peak with an onset temperature of 121.9° C. and a maximum at 130.3° C. and a second endothermic peak with an onset temperature of 243.9° C. and a maximum at 249.3° C. The DSC thermogram is provided in FIG. 29.

TGA analysis of the hydrochloride salt revealed 2.9% weight loss below 150° C. and significant weight loss above 225° C. due to decomposition of the sample. The TGA thermogram is provided in FIG. 30.

Example A. HPK1 Kinase Binding Assay

A stock solution of 1 mM test compound was prepared in DMSO. The compound plate was prepared by 3-fold and 11-point serial dilutions. 0.1 µL of the compound in DMSO was transferred from the compound plate to the white 384 well polystyrene plates. The assay buffer contained 50 mM HEPES, pH 7.5, 0.01% Tween-20, 5 mM $MgCl_2$, 0.01% BSA, and 5 mM DTT. 5 µL of 4 nM active HPK1 (Signal-Chem M23-11G) prepared in the buffer was added to the plate. The enzyme concentration given was based on the given stock concentration reported by the vender. 5 µl of 18 nM tracer 222 (ThermoFisher PV6121) and 4 nM LanthaScreen Eu-Anti GST antibody (ThermoFisher PV5595) were added. After one hour incubation at 25° C., the plates were read on a PHERAstar FS plate reader (BMG Labtech). Ki values were determined.

Compounds of the present disclosure, as exemplified in Examples 6 and 42 of U.S. patent application Ser. No. 16/278,865 (published as US Patent Publication No. 2019/0382380), showed the $K_i$ values in the following ranges: +=Ki≤100 nM; ++=100 nM<Ki≤500 nM; +++=500 nM<Ki≤5000 nM.

TABLE 11

| Compound | Ki, nM |
|---|---|
| 1 | + |
| 2 | + |

Example B. p-SLP76S376 HTRF Assay

One or more compounds of the invention can be tested using the p-SLP76S376 HTRF assay described as follows. Jurkat cells (cultured in RPMI1640 media with 10% FBS) are collected and centrifuged, followed by resuspension in appropriate media at $3\times10^6$ cells/mL. The Jurkat cells (35 mL) are dispensed into each well in a 384 well plate. Test compounds are diluted with cell culture media for 40-fold dilution (adding 39 mL cell culture media into 1 mL compound). The Jurkat cells in the well plate are treated with the test compounds at various concentrations (adding 5 ul diluted compound into 35 mL Jurkat cells and starting from 3 uM with 1:3 dilution) for 1 hour at 37° C., 5% $CO_2$), followed by treatment with anti-CD3 (5 mg/mL, OKT3 clone) for 30 min. A 1:25 dilution of 100× blocking reagent (from p-SLP76 ser376HTRF kit) with 4×Lysis Buffer (LB) is prepared and 15 mL of the 4×LB buffer with blocking reagent is added into each well and incubated at room temperature for 45 min with gentle shaking. The cell lysate (16 mL) is added into a Greiner white plate, treated with p-SLP76 ser376HTRF reagents (2 mL donor, 2 ul acceptor) and incubated at 4° C. for overnight. The homogeneous time resolved fluorescence (HTRF) is measured on a PHERAstar plate reader the next day. $IC_{50}$ determination is performed by fitting the curve of percent inhibition versus the log of the inhibitor concentration using the GraphPad Prism 5.0 software.

Example C. Isolation of CD4+ or CD8+ T Cells and Cytokine Measurement

Blood samples are collected from healthy donors. CD4+ or CD8+ T cells are isolated by negative selection using CD4+ or CD8+ enrichment kits (lifetech, USA). The purity of the isolated CD4+ or CD8+ T cells is determined by flow cytometry and is routinely >80%. Cells are cultured in RPMI 1640 supplemented with 10% FCS, glutamine and antibiotics (Invitrogen Life Technologies, USA). For cytokine measurement, Jurkat cells or primary CD4+ or CD8+ T cells are plated at 200 k cells/well and are stimulated for 24 h with anti-CD3/anti-CD28 beads in the presence or absence of testing compounds at various concentrations. 16 µL of supernatants are then transferred to a white detection plate and analyzed using the human IL2 or IFNγ assay kits (Cisbio).

Example D. Treg Assay

One or more compounds can be tested using the Regulatory T-cell proliferation assay described as following. Primary CD4+/CD25− T-cells and CD4+/CD25+ regulatory T-cells are isolated from human donated Peripheral Blood Mononuclear Cells, using an isolated kit from Thermo Fisher Scientific (11363D). CD4+/CD25− T-cells are labeled with CFSE (Thermo Fisher Scientific, C34554) following the protocol provided by the vendor. CFSE labeled T-cells and CD4+/CD25+ regulatory T-cells are re-suspended at the concentration of 1×106 cells/mL in RPMI-1640 medium. 100 mL of CFSE-labeled T-cells are mixed with or without 50 mL of CD4+/CD25+ regulatory T-cells, treated with 5 µl of anti-CD3/CD28 beads (Thermo Fisher Scientific, 11132D) and various concentrations of compounds diluted in 50 µl of RPMI-1640 medium. Mixed populations of cells are cultured for 5 days (37° C., 5% $CO_2$) and proliferation of CFSE-labeled T-cells is analyzed by BD LSRFortessa X-20 using FITC channel on the 5th day.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A unit dosage form comprising a solid form of Compound 1 having the formula:

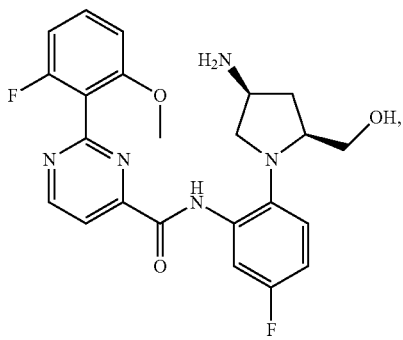

Compound 1 wherein the solid form has crystalline Form I, and wherein the solid form has at least one characteristic X-ray powder diffraction ("XRPD") peak selected from about 6.7, about 9.9, about 13.4, about 14.1, about 15.5, about 18.3, about 19.9, and about 20.4 degrees 2-theta.

2. The unit dosage form of claim 1, wherein the solid form has at least one characteristic XRPD peak selected from about 6.7, about 9.9, about 13.4, and about 15.5 degrees 2-theta.

3. The unit dosage form of claim 1, wherein the solid form has an XRPD pattern with characteristic peaks as substantially shown in FIG. 1.

4. The unit dosage form of claim 1, wherein the solid form exhibits a DSC thermogram having endotherm peaks at temperatures of about 86° C. and about 183° C.

5. The unit dosage form of claim 1, wherein the solid form has a DSC thermogram substantially as depicted in FIG. 2.

6. The unit dosage form of claim 1, wherein the solid form has a TGA thermogram substantially as depicted in FIG. 3.

7. A unit dosage form comprising a salt which is an acid salt of N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide, having the structure:

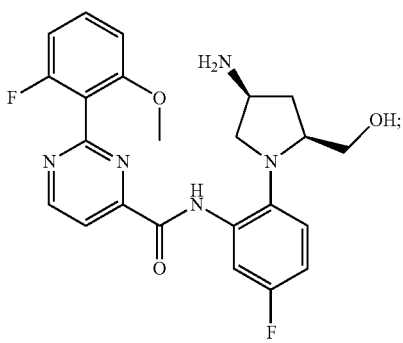

Compound 1 wherein the acid is selected from phosphoric acid, hydrochloric acid, L-(+)-tartaric acid, malic acid, camphorsulfonic acid, mandelic acid, and citric acid, wherein the salt is crystalline, and wherein:

the phosphoric acid salt of Compound 1 has at least one characteristic XRPD peak selected from about 6.3, about 6.4, about 7.0, about 8.9, about 11.2, about 12.5, about 19.9, and about 22.9 degrees 2-theta;

the hydrochloric acid salt of Compound 1 has at least one characteristic XRPD peak selected from about 6.7, about 9.1, about 11.0, about 12.7, about 13.5, about 15.5, about 17.1, and about 23.4 degrees 2-theta;

the L-(+)-tartaric acid salt of Compound 1 has at least one characteristic XRPD peak selected from about 4.9, about 7.9, about 9.8, about 15.9, about 16.9, about 19.6, and about 23.0 degrees 2-theta;

the malic acid salt of Compound 1 has at least one characteristic XRPD peak selected from about 5.2, about 7.9, about 10.4, about 14.3, about 15.8, about 16.6, about 18.0, about 21.0, and about 21.2 degrees 2-theta;

the camphorsulfonic acid salt of Compound 1 has at least one characteristic XRPD peak selected from about 4.9, about 5.9, about 10.9, about 14.4, about 15.0, about 15.1, about 19.8, about 20.1, and about 25.8 degrees 2-theta;

the mandelic acid salt of Compound 1 has at least one characteristic XRPD peak selected from about 4.2, about 5.0, about 5.4, about 5.8, about 6.9, about 14.2, about 15.3, about 19.0, and about 19.6 degrees 2-theta; and the citric acid salt of Compound 1 has at least one characteristic XRPD peak selected from about 7.3, about 9.0, about 13.6, about 16.6, about 18.1, about 18.3, about 19.5, about 20.1, and about 20.9 degrees 2-theta.

8. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide phosphate.

9. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide hydrochloride.

10. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide L-tartrate.

11. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide malate.

12. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide camsylate.

13. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide mandelate.

14. The unit dosage form of claim 7, wherein the salt is N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide citrate.

15. The unit dosage form of claim 8, wherein the salt has an X-ray powder diffraction pattern with characteristic peaks as substantially shown in FIG. 4.

16. The unit dosage form of claim 9, wherein the salt has an X-ray powder diffraction pattern with characteristic peaks as substantially shown in FIG. 7.

17. The unit dosage form of claim 10, wherein the salt has an X-ray powder diffraction pattern with characteristic peaks as substantially shown in FIG. 10.

18. The unit dosage form of claim 11, wherein the salt has an X-ray powder diffraction pattern with characteristic peaks as substantially shown in FIG. 13.

19. The unit dosage form of claim 12, wherein the salt has an X-ray powder diffraction pattern with characteristic peaks as substantially shown in FIG. 16.

20. The unit dosage form of claim 13, wherein the salt has an X-ray powder diffraction pattern with characteristic peaks as substantially shown in FIG. 19.

21. The unit dosage form of claim 14, wherein the salt has an X-ray powder diffraction pattern with characteristic peaks as substantially shown in FIG. 22.

22. A unit dosage form comprising a salt which is an acid salt of N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide, having the structure:

Compound 2

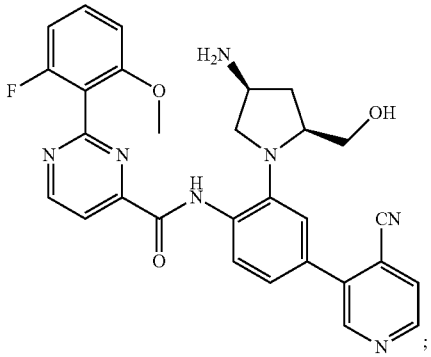

wherein the acid is selected from phosphoric acid and hydrochloric acid, wherein the salt is crystalline, and wherein:

the phosphoric acid salt of Compound 2 has at least one characteristic XRPD peak selected from about 5.9, about 6.7, about 10.2, about 13.4, about 14.5, about 15.5, about 16.5, about 17.4, and about 18.0 degrees 2-theta; and the hydrochloric acid salt of Compound 2 has at least one characteristic XRPD peak selected from about 6.2, about 6.8, about 11.2, about 12.5, about 13.6, about 17.3, about 18.4, about 21.6, and about 22.3 degrees 2-theta.

23. The unit dosage form of claim 22, wherein the salt is N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide phosphate.

24. The unit dosage form of claim 22, wherein the salt is N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide hydrochloride.

25. The unit dosage form of claim 23, wherein the salt has an X-ray powder diffraction pattern with characteristic peaks as substantially shown in FIG. 25.

26. The unit dosage form of claim 24, wherein the salt has an X-ray powder diffraction pattern with characteristic peaks as substantially shown in FIG. 28.

* * * * *